US006306622B1

(12) United States Patent
Rosenbaum et al.

(10) Patent No.: US 6,306,622 B1
(45) Date of Patent: Oct. 23, 2001

(54) CDNA ENCODING A BMP TYPE II RECEPTOR

(75) Inventors: Jan Susan Rosenbaum, Cincinnati, OH (US); Tsutomu Nohno, Okayama-ken (JP)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 08/334,179

(22) Filed: Nov. 4, 1994

(51) Int. Cl.$^7$ .............................. C07K 14/00; C12N 5/06; C12N 5/10; C12N 15/63
(52) U.S. Cl. ...................... 435/69.1; 435/320.1; 435/325; 435/365; 530/350; 536/23.1; 536/23.5
(58) Field of Search .......................... 530/350; 435/69.1, 435/320.1, 325, 365; 536/23.1, 23.5

(56) References Cited

U.S. PATENT DOCUMENTS

| 5,141,905 | 8/1992 | Rosen et al. | 435/69.1 |
| 5,216,126 | 6/1993 | Cox et al. | 530/350 |
| 5,547,854 | * 8/1996 | Donahoe et al. | 435/69.1 |

FOREIGN PATENT DOCUMENTS

| 0 369 861 | 5/1990 | (EP). |
| WO 92/20793 | 11/1992 | (WO). |
| WO 93/09228 | 5/1993 | (WO). |
| WO 93/19177 | 9/1993 | (WO). |
| 94/11502 | 5/1994 | (WO). |
| 95/14778 | 1/1995 | (WO). |
| 95/07982 | 3/1995 | (WO). |

OTHER PUBLICATIONS

Bergonzoni, L., Caccia, P., Cletini, O., Sarmientos, P., & Isacchi, A. (Nov. 15, 1992) "Characterization of a Biologically Active Extracellular Domain of Fibroblast Growth Factor Receptor 1 Expressed in *Escherichia coli*", Eur. J. Biochem., 210, 823–829.

Fernandez–Botran, R. (Aug. 1991) "Soluble Cytokine Receptors: Their Role in Immunoregulation", FASEB J., 5, 2567–2574.

Kawabata, M., Chytil, A. & Moses, H. (Mar. 10, 1995) "Cloning of a Novel Type II Serine/Threonine Kinase Receptor through Interaction with the Type I Transforming Growth Factor–β Receptor", J. Biol. Chem., 270, 5625–5630.

Lev, S., Yarden, Y. & Givol, D. (May 25, 1992) "A Recombinant Ectodomain of the Receptor for the Stem Cell Factor (SCF) Retains Ligand–induced Receptor Dimerization and Antagonizes SCF–simulated Cellular Responses", J. Biol. Chem. 267, 10866–10873.

Lin, H., Moustakas, A., Knaus, P., Wells, R., Henis, Y. & Lodish, H. (Feb. 10, 1995) "The Soluble Exoplasmic Domain of the Type II Transforming Growth Factor (TGF)–β Receptor", J. Biol. Chem. 270, 2747–2754.

Liu, F., Ventura, F., Doody, J., & Massagué, J. (Jul. 1995) "Human Type II Receptor for Bone Morphogenic Proteins (BMPs): Extension of the Two–Kinase Receptor Model to the BMPs", Mol. Cell. Biol. 15, 3479–3486.

Nohno, T., Ishikawa, T., Saito, T., Hosokawa, K., Noji, S., Wolsing, D., & Rosenbaum, J. (Sep. 22, 1995) "Identification of a Human Type II Receptor for Bone Morphogenetic Protein–4 That Forms Differential Heteromeric Complexes with Bone Morphogenetic Protein Type I Receptors", J. Biol. Chem. 270, 22522–22526.

Pennica, D., Kohr, W., Fendly, B., Shire,S., Raab, H., Borchardt, P., Lewis, M. & Goeddel, D. (Jan. 1992) "Characterization of a Recombinant Extracellular Domain of the Type 1 Tumor Necrosis Factor Receptor: Evidence for Tumor Necrosis Factor– Induced Receptor Aggregation", Biochemistry 31, 1134–1141.

Rosenzweig B. L., Imamura, T., Okadome, T., Cox, G., Yamashita, H., Ten Dijke, P., Heldin, C. & Miyazono, K. (Aug. 1995) "Cloning and Characterization of a Human Type II Receptor for Bone Morphogenetic Proteins", Proc. Natl. Acad. Sci. 92, 7632–7636.

Hoodless, P. A., Haerry, T. Abdollah, S., Stapleton, M., O'Connor, M.B., Attisano, L., and Wrana, J.L. (May 17, 1996). "MADR1, a MAD–related protein that functions in BMP–2 signalling pathways", Cell 85: 489–500.

Liu, F., Hata A., Baker, J.C., Doody, J., Cárcamo, J., Harland, R.M., and Massagué, J. (Jun. 13, 1996). "A human Mad protein acting as a BMP–regulated transcriptional activator", Nature 381:620–623.

Brummel, T.J., V. Twombly, G. Marqués, J.L. Wrana, S.J. Newfeld, L. Attisano, J. Massagué, M.B. O'Connor and W.M. Gelbart, "Characterization and Relationship of dpp Receptors Encoded by the Saxaphone and Thick Veins genes in Drosphilia", Cell, vol. 78, pp. 251–261 (Jul. 29, 1994).

Chen, R–H. and R. Derynck, "Homomeric Interactions Between Type II Transforming Growth Factor β Receptors", J. Biol. Chem., vol. 269, No. 36, pp. 22868–22874 (Sep. 9, 1994).

Ebner, R., R.–H. Chen, S. Lawler, T. Zioncheck and R. Derynck, "Determination of Type I Receptor Specificity by the Type II Receptors for TGF–β or Activin", Science, vol. 262, pp. 900–902 (Nov. 5, 1993).

Garrison, J.C., "Study of Protein Phosphorylation in Intact Cells", B:Protein Phosphorylation, A Practical Approach, Chapter 1, pp. 1–29, Hardie, D.G. (ed), (no month identified 1993).

(List continued on next page.)

*Primary Examiner*—Gary L. Kunz
*Assistant Examiner*—Steve Gucker
(74) *Attorney, Agent, or Firm*—Kelly L. McDow-Dunham; Carl J. Roof; Brahm J. Corstanje

(57) ABSTRACT

The present invention relates to an isolated BMP, (bone morphogonic protein) receptor kinase protein or soluble fragment thereof, a DNA sequence coding for the BMP receptor kinase protein or the soluble fragment thereof, a recombinant expression vector comprising the DNA sequence, a host cell comprising the recombinant expression vector, and a method of expressing the BMP receptor kinase protein or soluble fragment thereof.

31 Claims, 15 Drawing Sheets

OTHER PUBLICATIONS

Inagaki, M., A. Moustakas, H.Y. Lin, H.F. Lodish and B.I. Carr, "Growth Inhibition By Transforming Growth Factor β (TGF–β) Type I is Restored in TGF–β Resistant Hepatoma Cells After Expression of TGF–β Receptor Type II cDNA", Proc. Nat'l. Acad. Sci. USA, vol. 90, pp. 5359–5363 (Jun. 1993).

Nellen, D., M. Affolter and K. Basler, "Receptor Serine/Threonine Kinases Implicated in the Control of Drosophila Body Pattern by Decapentaplegic", Cell, vol. 78, pp. 225–237 (Jul. 29, 1994).

Okano, H., S. Yoshikawa, A. Suzuki, N. Ueno, M. Kaizu, O. Masataka, T. Takahashi, M. Matsumoto, K. Sawamoto and K. Mikoshiba, "Cloning of a Drosophila melanogaster Homologue of the Mouse Type I Bone Morphogenetic Proteins–2/–4 Receptor: A Potential Decapentaplegic Receptor", Gene, vol. 148, pp. 203–209 (no month identified 1994).

Suzuki, A., N. Shioda, T. Maeda, M. Tada and N. Ueno, "A Mouse TGF–β Type I Receptor or Ligand Binding", Biochem. Biophys. Res. Commun., vol. 198, No. 3, pp. 1063–1069 (Feb. 15, 1994).

Takeda, K., S. Oida, H. Ichiho, T. Iimura, Y. Maruoka, T. Amagasa and S. Sasaki, "Molecular Cloning of Rat Bone Morphogenetic Protein (BMP) Type IA Receptor and Its Expression During Ectopic Bone Formation Induced by MBP", Biochem. Biophys. Res. Commun., vol. 204, No. 1, pp. 203–209 (Oct. 14, 1994).

Wrana, J.L., L. Attisano, J. Cárcamo, A. Zentella, J. Doody, M. Laiho, X–F. Wang and J. Massagué, "TGF–β Signals Through a Heteromeric Protein Kinase Receptor Complex", Cell, vol. 71, pp. 1003–1014 (Dec. 11, 1992).

Wrana, J.L., L. Attisano, R. Wieser, F. Ventura and J. Massagué, "Mechanism of Activation of the TGF–β Receptor", Nature, vol. 370, pp. 341–347 (Aug. 4, 1994).

Yamashita, H., P. ten Dijke, P. Franzén, K. Miyazono and C–H. Heldin, "Formation of Hetero–oligomeric Complexes of Type I and Type II Receptors for Transforming Growth Factor–β", J. Biol. Chem., vol. 269, No. 31, p. 20172–20178 (Aug. 5, 1994).

Attisano, L., J. Cárcamo, F. Ventura, F. M. B. Weis, J. Massagué and J. L. Wrana, "Identification of Human Activin and TGFβ Type I Receptors That Form Heteromeric Kinase Complexes with Type II Receptors", Cell, vol. 75, pp. 671–680 (Nov. 19, 1993).

Attisano, L., J. L. Wrana, S. Cheifetz and J. Massagué, "Novel Activin Receptors: Distinct Genes and Alternative mRNA Splicing Generate a Repertoire of Serine/Threonine Kinase Receptors", Cell, vol. 68, pp. 97–108 (Jan. 10, 1992).

Attisano, L., J. L. Wrana, F. López–Casillas and J. Massagué, "TGF–β Receptors and Actions", Biochimica et Biophysica Acta, vol. 1222, No. 1, pp. 71–80 (May 26, 1994).

Baarends, W. M., M. J. L. van Helmond, M. Post, P. J. C. M. van der Schoot, J. W. Hoogerbrugge, J. P. de Winter, J. T. J. Uilenbroek, B. Karels, L. G. Wilming, J. H. C. Meijers, A. P. N. Themmen and J. A. Grootegoed, "A Novel Member of the Transmembrane Serine/threonine Kinase Receptor Family Is Specifically Expressed in the Gonads and in Mesenchymal Cells Adjacent to the Müllerian Duct", Development, vol. 120, pp. 189–197 (Jan. 1994).

Basler, K., T. Edlund, T. M. Jessell and T. Yamada, "Control of Cell Pattern in the Neural Tube: Regulation of Cell Differentiation by dorsalin–1, a Novel TGFβ Family Member", Cell, vol. 73, pp. 687–702 (May 1993).

Bassing, C. H., J. M. Yingling, D. J. Howe, T. Wang, W. W. He, M. L. Gustafson, F. Shah, P. K. Donahoe and X. P. Wang, "A Transforming Growth Factor β Type I Receptor That Signals to Activate Gene Expression", Science, vol. 263, pp. 87–89 (Jan. 7, 1994).

Blessing, M., L. B. Nanney, L. E. King, C. M. Jones and B. L. Hogan, "Transgenic Mice as a Model to Study the Role of TGF–β–related molecules in Hair Follicles", Genes Dev., vol. 7, No. 2, pp. 204–215 (Feb. 1993).

Cércamo, J., F. M. B. Weis, F. Ventura, R. Wieser, J. L. Wrana, L. Attisano and J. Massagué, "Type I Receptors Specify Growth–Inhibitory and Transcriptional Responses to Transforming Growth Factor β and Activin", Molecular and Cellular Biology, vol. 14, No. 6, pp. 3810–3821 (Jun. 1994).

Cunningham, N. S., V. Paralkar and A. H. Reddi, "Osteogenin and Recombinant Bone Morphogenetic Protein 2B Are Chemotactic for Human Monocytes and Stimulate Transforming Growth Factor $β_1$ mRNA Expression", Proc. Natl. Acad. Sci. USA, vol. 89, pp. 11740–11744 (Dec. 1992).

Drozdoff, V., N. A. Wall and W. J. Pledger, "Expression and Growth Inhibitory Effect of Decapentaplegic Vg–related protein 6: Evidence for a Regulatory Role in Keratinocyte Differentiation", Proc. Natl. Acad. Sci. USA, vol. 91, pp. 5528–5532 (Jun. 1994).

Estevez, M., L. Attisano, J. L. Wrana, P. S. Albert, J. Massagué and D. L. Riddle, "The daf–4 Gene Encodes A Bone Morphogenetic Protein Receptor Controlling C. elegans Dauer Larva Development", Nature, vol. 365, pp. 644–649 (Oct. 14, 1993).

Franzén, P., P. ten Dijke, H. Ichijo, H. Yamashita, P. Schulz, C. H. Heldin and K. Miyazono, Cloning of a TGFβ Type I Receptor That Forms a Heteromeric Complex with the TGFβ Type II Receptor, Cell, vol.75, pp. 681–692 (Nov. 19, 1993).

Georgi, L. L., P. S. Albert and D. L. Riddle, "daf–1, a C. elegans Gene Controlling Dauer Larva Development, Encodes a Novel Receptor Protein Kinase", Cell, vol. 61, pp. 635–645 (May 18, 1990).

He, W. W. , M. L. Gustafson, S. Hirobe and P. K. Donahoe, "Developmental Expression of Four Novel Serine Threonine Kinase Receptors Homologous to the Activin Transforming Growth Factor–β Type II Receptor Family", Developmental Dynamics, vol. 196, pp. 133–142 (Feb. 1993).

Koenig, B.B., J. S. Cook, D. H. Wolsing, J. Ting, J. P. Tiesman, P. E. Correa, C. A. Olson, A. L. Pecquet, F. Ventura, R. A. Grant, G. X. Chen, J. L. Wrana, J. Massagué, and J. S. Rosenbaum, "Characterization and Cloning Of A Receptor For BMP–2 and BMP–4 From NIH3T3 Cells," Molecular and Cellular Biology, vol. 14, No. 9, pp. 5961–5974 (Sep. 1994).

Lin, H. Y, X. F. Wang, E. Ng–Eaton, R. A. Weinberg and H. F. Lodish, "Expression Cloning of the TGF–β Type II Receptor, a Functional Transmembrane Serine/Threonine Kinase", Cell, vol. 68, pp. 775–785 (Feb. 21, 1992).

Lin, H.Y. and A. Moustakas, "TGF–β Receptors: Structure and Function", Cellular and Molecular Biology, vol. 40, No. 3, pp. 337–349 (Mar. 1994).

Lyons, K. M., C. M. Jones and B. L. M. Hogan, "The DVR Gene Family in Embryonic Development", Trends in Genetics, vol. 7, No. 11–12, pp. 408–412 (Nov./Dec. 1991).

Luyten, F. P., P. Chen, V. Paralkar and A. H. Reddi, "Recombinant Bone Morphogenetic Protein–4, Transforming Growth Factor–$\beta_1$, and Activin A Enhance the Cartilage Phenotype of Articular Chondrocytes in Vitro," Experimental Cell Research, vol. 210, pp. 224–229 (Feb. 1994).

Mathews, L. S., "Activin Receptors and Cellular Signaling by the Receptor Serine Kinase Family", Endocrine Reviews, vol. 15, No. 3, pp. 310–325 (Jun. 1994).

Mathews, L. S. and W. W. Vale, "Expression Cloning of an Activin Receptor, a Predicted Transmembrane Serine Kinase", Cell, vol. 65, pp. 973–982 (Jun. 14, 1991).

Mathews, L. S., W. W. Vale and C. R. Kintner, "Cloning of a Second Type of Activin Receptor and Functional Characterization in Xenopus Embryos", Science, vol. 255, pp. 1702–1705 (Mar. 27, 1992).

Nohno, T., S. Sumitomo, T. Ishikawa, C. Ando, S. Nishida, S. Noji and T. Saito, "Nucleotide Sequence of a cDNA Encoding the Chicken Receptor Protein Kinase of the TGF–$\beta$ Receptor Family", J. DNA Sequencing and Mapping, vol. 3, No. 6, pp. 393–396 (no month identified 1993).

Özjkaynak, E., P.N.H, Schnegelsberg, D.F. Jin, G.M, Clifford, F. D. Warren, E. A. Drier and H. Oppermann, "Osteogenic Protein–2: A New Member of the Transforming Growth Factor–$\beta$ Superfamily Expressed Early in Embryogenesis", J. Biol. Chem., vol. 267, No. 35, pp. 25220–25227 (Dec. 1992).

Paralkar, V. M., R. G. Hammonds and A. H. Reddi, "Identification and Characterization of Cellular Binding Proteins (Receptors) for Recombinant Human Bone Morphogenetic Protein 2B, an Initiator of Bone Differentiation Cascade", Proc. Natl. Acad. Sci. USA, vol. 88, pp. 3397–3401 (Apr. 1991).

Penton, A., Y. Chen, K. Staehling–Hampton, J. L. Wrana, L. Attisano, J. Szidonya, A. Cassill, J. Massagué and F. M. Hoffmann, "Identification of Two Bone Morphogenetic Protein Type I Receptors in Drosophila and Evidence That BRK25D is a Decapentaplegic Receptor," Cell, vol. 78, pp. 239–250 (Jul. 29, 1994).

Sumitomo, S., T. Saito and T. Nohno, "A New Receptor Protein Kianse from Chick Embryo Related to Type II Receptor for TGF–$\beta$", J. DNA Sequencing and Mapping, vol. 3, pp. 297–302 (no month identified 1993).

ten Dijke, P., H. Ichijo, P. Franzén, P. Schulz, J. Saras, H. Toyoshima, C. H. Heldin and K. Miyazono, "Activin Receptor–like Kinase: A Novel Subclass of Cell–surface Receptors with Predicted Serine/Threonine Kinases Activity", Oncogene, vol. 8, pp. 2879–2887 (no month identified 1993).

ten Dijke, H. Yamashita, H. Ichijo, P. Franzén, M. Laiho, K. Miyazono, C. H. Heldin, "Characterization of Type I Receptors for Transforming Growth Factor–$\beta$ and K. Activin", Science, vol. 264, pp. 101–104 (Apr. 1, 1994).

ten Dijke, P., H. Yamashita, T. K. Sampath, A. H. Reddi, M. Estevez, D. L. Riddle, H. Ichijo, C. H. Heldin and Miyazono, "Identification of Type I Receptors for Osteogenic Protein–1 and Bone Morphogenetic Protein–4", J. Biological Chemistry, vol. 269, No. 25, pp. 16985–16988 (Jun. 1994).

Wall, N.A., M. Blessing, V.V.E. Wright and B.L.M. Hogan, "Biosynthesis and In Vivo Localization of the Decapentaplegic–Vg–related Protein, DVR–6 (Bone Morphogenetic Protein–6)", J. Cell Biol., vol. 120, No. 2, pp. 493–502 (Jan. 1993).

Wozney, J. M., "The Bone Morphogenetic Protein Family", Molec. Reproduct. and Develop., vol. 32, No. 2, pp. 160–167 (Jun. 1992).

Xie, T., A. L. Finelli and R. W. Padgett, "The Drosophila saxophone Gene: A Serine–Threonine Kinase Receptor of the TGF–$\beta$ Superfamily", Science, vol. 263, pp. 1756–1759 (Mar. 25, 1994).

Yamaji, N., R. S. Thies, A. J. Celeste and J. M. Wozney, "The Molecular Cloning of Bone Morphogenetic Protein Receptors", Abstract from Meeting of American Society for Bone and Mineral Research, (Sep. 22, 1993).

* cited by examiner

PCR PRIMERS USED IN ISOLATION OF HUMAN BRK-3

TSK-1: Sense derived form kinase domain II

```
                        A A
5' G A C G T N G C N G T N A A     T N T T 3'
                        G G
```

TSK-2: Antisense derived from kinase domain VIII

```
       T                      T A
5' G A C   T C N G G N G C N A A     T A 3'
       C                      G G
```

AVR-5: Sense derived form kinase domain IV

```
           A     T     A     T
5' A T G A A   C A   G A   A A   A T 3'
           G     C     G     C
```

TSK-4: Antisense derived form kinase domain VIB

CDNA ENCODING A BMP TYPE II RECEPTOR

TECHNICAL FIELD

The present invention relates to the field of bone formation and development. Specifically, the present invention relates to a bone morphogenetic protein receptor, a DNA sequence coding for said receptor, and cells transfected with a DNA sequence coding for said receptor.

BACKGROUND

Humans and other warm-blooded animals can be afflicted by a number of bone-related disorders. Such disorders range from bone fractures, to debilitating diseases such as osteoporosis. While in healthy individuals bone growth generally proceeds normally and fractures heal without the need for pharmacological intervention, in certain instances bones may become weakened or may fail to heal properly. For example, healing may proceed slowly in the elderly and in patients undergoing treatment with corticosteroids (e.g., transplant patients). Osteoporosis is a condition in which bone hard tissue is lost disproportionately to the development of new hard tissue. Osteoporosis can generally be defined as the reduction in the quantity of bone, or the atrophy of skeletal tissue; marrow and bone spaces become larger, fibrous binding decreases, and compact bone becomes fragile. Another bone related disorder is osteoarthritis, which is a disorder of the movable joints characterized by deterioration and abrasion of articular cartilage, as well as by formation of new bone at the joint surface.

While a variety of treatments are available for such bone-related disorders, none of the treatments provide optimum results. One of the difficulties facing individuals who treat bone-related disorders is a lack of complete understanding of bone metabolism and of the bone-related disorders. A key to such understanding is identifying and characterizing each of the components involved in bone growth. Bone morphogenetic proteins (BMPs) have been demonstrated to play a role in bone formation and development (J. M. Wozney, *Molec. Reproduct. and Develop.*, 32: 160–167 (1992)).

Furthermore, the role of BMPs may not be limited to their role in bone. The finding that the BMPs are found at significant concentrations in other tissues such as brain, kidney, stratified squamous epithelia, and hair follicle (N. A. Wall, M. Blessing, C. V. E. Wright, and B. L. M. Hogan, *J. Cell Biol.*, 120: 493–502 (1993); E. Özkaynak, P. N. J. Schnegelsberg, D. F. Jin, G. M. Clifford, F. D. Warren, E. A. Drier, and H. Oppennann, *J. Biol. Chem.*, 267: 25220–25227 (1992); K. M. Lyons, C. M. Jones, and B. L. M. Hogan, *Trends in Genetics*, 7: 408–412 (1991); V. Drozdoff, N. A. Wall, and W. J. Pledger, *Proceedings of the National. Academy of Sciences, U.S.A.*, 91: 5528–5532 (1994)) suggests that they may play additional roles in development and differentiation. In support of this, BMPs have recently been found to promote nerve cell differentiation and to affect hair follicle formation (K. Basler, T. Edlund, T. M. Jessell, and T. Yamada, *Cell*, 73: 687–702 (1993); V. M. Paralkar, B. S. Weeks, Y. M. Yu, H. K. Klieinman, and A. H. Reddi, *J. Cell Biol.*, 119: 1721–1728 (1992); M. Blessing, L. B. Nanney, L. E. King, C. M. Jones, and B. L. Hogan, *Genes Dev.*, 7: 204–215 (1993)).

A BMP initiates its biological effect on cells by binding to a specific BMP receptor expressed on the plasma membrane of a BMP-responsive cell. A receptor is a protein, usually spanning the cell membrane, which binds to a ligand from outside the cell, and as a result of that binding sends a signal to the inside of the cell which alters cellular function. In this case, the ligand is the protein BMP, and the signal induces the cellular differentiation.

Because of the ability of a BMP receptor to specifically bind BMPs, purified BMP receptor compositions are useful in diagnostic assays for BMPs, as well as in raising antibodies to the BMP receptor for use in diagnosis and therapy. In addition, purified BMP receptor compositions may be used directly in therapy to bind or scavenge BMPs, thereby providing a means for regulating the activities of BMPs in bone and other tissues. In order to study the structural and biological characteristics of BMP receptors and the role played by BMPs in the responses of various cell populations to BMPs during tissue growth/formation stimulation, or to use a BMP receptor effectively in therapy, diagnosis, or assay, purified compositions of BMP receptor are needed. Such compositions, however, are obtainable in practical yields only by cloning and expressing genes encoding the receptors using recombinant DNA technology. Efforts to purify BMP receptors for use in biochemical analysis or to clone and express mammalian genes encoding BMP receptors have been impeded by lack of a suitable source of receptor protein or mRNA. Prior to the present invention, few cell lines were known to express high levels of high affinity BMP receptors which precluded purification of the receptor for protein sequencing or construction of genetic libraries for direct expression cloning. Availability of the BMP receptor sequence will make it possible to generate cell lines with high levels of recombinant BMP receptor for biochemical analysis and use in screening experiments.

The BMPs are members of the TGF-β superfamily. Other members of the TGF-β superfamily include TGF-β, activins, inhibins, Müllerian Inhibiting Substance, and the Growth and Differentiation Factors (GDFs). As expected, the receptors for various members of the TGF-β superfamily share similar structural features. Receptors of the TGF-β ligand superfamily are typically classified into one of two subgroups, designated as type I and type II. The type I and type II receptors are classified as such based on amino acid sequence characteristics. Both the type I and type II receptors possess a relatively small extracellular ligand binding domain, a transmembrane region, and an intracellular protein kinase domain that is predicted to have serine/threonine kinase activity (Lin and Moustakas, *Cellular and Molecular Biology*, 40: 337–349 (1994); L. S. Mathews, *Endocrine Reviews*, 15: 310–325 (1994); L. Attisano, J. L. Wrana, F. López-Casillas, and J. Massagué, *Biochimica et Biophysica Acta*, 1222: 71–80 (1994)).

The type I receptors cloned to date belong to a distinct family whose kinase domains are highly related and share >85% sequence similarity (B. B. Koenig et al., *Molecular and Cellular Biology*, 14: 5961–5974 (1994)). The intracellular juxtamembrane region of the type I receptors is characterized by an SGSGSG motif 35–40 amino acids from the transmembrane region, and the carboxy terminus of these receptors is extremely short (B. B. Koenig et al., *Molecular and Cellular Biology*, 14: 5961–5974 (1994); L. Attisano, J. L. Wrana, F. López-Casillas, and J. Massagué, *Biochimica et Biophysica Acta*, 1222: 71–80 (1994)). The extracellular domain of the type I receptors contains a characteristic cluster of cysteine residues, termed the "cysteine box", located within 25–30 amino acids of the transmembrane region, and another cluster of cysteine residues, termed the "upstream cysteine box", located after the putative signal sequence (B. B. Koenig, et al., *Molecular and*

Cellular Biology, 14: 5961–5974 (1994); L. Attisano, et al., Biochimica et Biophysica Acta, 1222: 71–80 (1994)).

In contrast to the type I receptors, the kinase domains of the type II receptors are only distantly related to one another. The SGSGSG motif found in type I receptors is not found in type II receptors. Also, the "upstream cysteine box" of type I receptors is not present in type II receptors. Furthermore, while all of the activin type II receptors contain a proline-rich sequence motif in the intracellular juxtamembrane region, there is no characteristic sequence motif that is common to all type II receptors (L. S. Mathews, Endocrine Reviews, 15: 310–325 (1994)). The length of the carboxy terminus of the type II receptors is considerably variable, with the longest known carboxy terminus being found in the BMP type II receptor, DAF-4 (M. Estevez, L. Attisano, J. L. Wrana, P. S. Albert, J. Massagué, and D. L. Riddle, Nature, 365: 644–49 (1993)), that was cloned from the nematode C. elegans. The extracellular domain of the type II receptors contains a single cysteine box located near the transmembrane region. Aside from the presence of the cysteine box, there is little sequence similarity amongst the extracellular domains of the type II receptors for TGF-β, activin, and BMPs.

Signaling by members of the TGF-β ligand superfamily requires the presence of both type I and type II receptors on the surface of the same cell (L. S. Mathews, Endocrine Reviews, 15: 310–325 (1994); L. Attisano, J. L. Wrana, F. L ópez-Casillas, and J. Massagué, Biochimica et Biophysica Acta, 1222: 71–80 (1994)). The BMPs are members of the TGF-β ligand superfamily; given the high degree of structural similarity among these family members, it is expected that their receptors will be structurally and functionally related to the TGF-β and activin receptors. It is anticipated that, like the TGF-β and activin receptor systems (J. Massagué, L. Attisano, and J. L. Wrana, Trends in Cell Biology, 4: 172–178 (1994)), both a BMP type I receptor and a BMP type II receptor will be needed in order to transduce a BMP signal within a cell or tissue. Hence, there is a need for a mammalian type II BMP receptor kinase protein in addition to the type I receptors that have already been cloned.

Three distinct mammalian type I receptors have been reported for the BMPs: BRK-1 (see U.S. Ser. No. 08/158, 735, filed Nov. 24, 1993 by J. S. Cook, et al.; and B. B. Koenig et al., Molecular and Cellular Biology, 14: 5961–5974 (1994)), ALK-2, and ALK-6. BRK-1 is the mouse homologue of ALK-3, which has also been demonstrated to bind BMP-4, as does ALK-6; ALK-2 binds BMP-7 (see P. ten Dijke, H. Yamashita, T. K. Sampath, A. H. Reddi, M. Estevez, D. L. Riddle, H. Ichijo, C. H. Heldin, and K. Miyazono, J. Biological Chemistry, 269: 16985–16988 (1994)). It is also postulated that ALK-6 is the mouse homologue of the chicken receptor BRK-2 (also referred to as RPK-1) (S. Sumitomo, T. Saito, and T. Nohno, DNA Sequence, 3: 297–302 (1993)).

The only type II receptor for BMP-2 and BMP-4, named DAF-4, has been cloned from the nematode C. elegans (M. Estevez, L. Attisano, J. L. Wrana, P. S. Albert, J. Massagué, and D. L. Riddle, Nature, 365: 644–9 (1993)). Because of the large evolutionary distance between the nematode and mammals, it has not been possible to use the DAF-4 cDNA as a probe with which to clone the mammalian DAF-4 homologue. This implies that the DNA sequence of the mammalian type II receptor for BMPs is substantially divergent from that of DAF-4, and it is necessary to clone a mammalian type II receptor for the BMPs. Thus, the BMP receptor kinase protein of the present invention provides a mammalian type II receptor which will enable the formation of a high affinity complex that is competent for signaling a response to BMPs in concert with the mammalian type I receptor(s) for BMPs. The mammalian BMP receptor complex is therefore more relevant for the identification of novel compounds which interact with the BMP receptor, and which will be useful as therapeutic agents in humans and other mammals, than is a receptor complex that is composed of the nematode type II receptor and the mammalian type I receptor.

OBJECTS OF THE PRESENT INVENTION

It is an object of the present invention to provide an isolated BMP type II receptor kinase protein.

It is also an object of the present invention to provide a DNA sequence encoding a BMP type II receptor kinase protein.

It is also an object of the present invention to provide a recombinant expression vector encoding a BMP type II receptor kinase protein.

It is also an object of the present invention to provide a host cell comprising a recombinant expression vector encoding a BMP receptor kinase protein.

It is also an object of the present invention to provide a method for producing a BMP type II receptor kinase protein, or a soluble fragment thereof.

It is also an object of the present invention to provide antibodies specific for the BMP type II receptor kinase proteins of the present invention.

It is also an object of the present invention to provide a reporter system for evaluating whether a test compound is capable of acting as an indirect agonist or antagonist of the BMP type II receptor protein kinase of the present invention.

It is also an object of the present invention to provide a method for determining whether a compound is capable of binding to a BMP receptor kinase protein of the present invention.

SUMMARY

The present invention relates to an isolated BMP type II receptor kinase protein or soluble fragment thereof, a DNA sequence coding for said BMP receptor kinase protein or said soluble fragment thereof, a recombinant expression vector comprising said DNA sequence, a host cell comprising said recombinant expression vector, a method of expressing said BMP receptor kinase protein or soluble fragment thereof, an antibody directed to a BMP type II receptor kinase protein of the present invention, a method for evaluating whether a test compound is capable of acting as an indirect agonist or antagonist to the BMP type II receptor protein kinase of the present invention, and a method for determining whether a compound is capable of binding to a BMP receptor kinase protein of the present invention.

BRIEF DESCRIPTION OF THE DRAWINGS

FIG. 1 shows the DNA sequence of the degenerate oligonucleotide primers used in the PCR amplification of t-BRK-3. The nucleotide bases adenine, thymine, cytosine, and guanine are represented by A, T, C and G respectively. The letter N represents the presence of an equal mixture of A, T, C, and G at that site. The primers are derived from the sequence of the TGF-β type II receptor (H. Y. Lin, X. F. Wang, E. Ng-Eaton, R. A. Weinberg, and H. F. Lodish, Cell, 68: 775–785 (1992)).

DESCRIPTION

Figure 2:
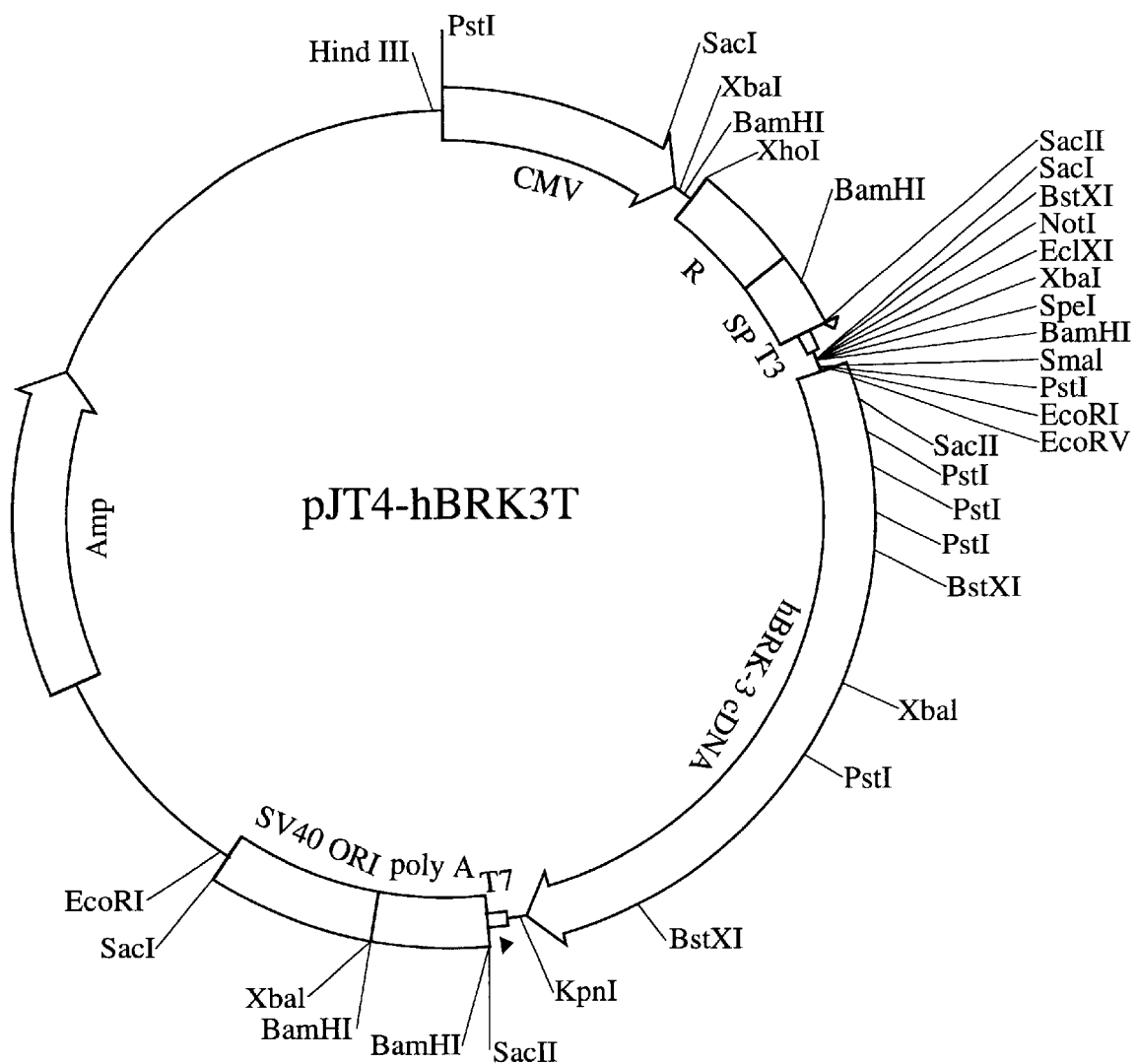
FIG. 2 shows the construct pJT4-hBRK3T, used for transient mammalian expression of t-BRK-3. CMV, cytomegalovirus early promoter/enhancer; R, the "R" element from the long terminal repeat of human T-cell leukemia virus-1; SP, an intron splice site from the SV40 virus; T3, promoter region from the T3 bacteriophage; T7, promoter region from the T7 bacteriophage; poly A, region from the SV40 virus directing polyadenylation of the message; SV40 ORI, origin of replication from the SV40 virus; Amp, ampicillin resistance gene for selection in E. coli.

The present invention answers the need for a mammalian BMP type II receptor by providing an isolated BMP receptor kinase protein; a DNA sequence coding for said protein; a recombinant expression vector comprising said DNA sequence; a host cell comprising said recombinant expression vector; and a method of expressing said BMP receptor kinase protein. The BMP type II receptor of the present invention will also reconstitute the high affinity BMP receptor complex thought to be necessary for signaling in concert with the BMP type I receptors.

As used herein, "human BMP receptor kinase protein-3" or "h-BRK-3" means a protein having the amino acid sequence SEQ ID NO:2, as well as proteins having amino acid sequences substantially similar to SEQ ID NO:2, and which are biologically active in that they are capable of binding a BMP molecule (including, but not limited to BMP-2, DR-BMP-2, BMP-4, and/or BMP-7), or transducing a biological signal initiated by a BMP molecule binding to a cell, or crossreacting with antibodies raised against h-BRK-3 protein, or peptides derived from the protein sequence of h-BRK-3 or m-BRK-3 (see below), or forming a complex with a BMP type I receptor, or co-immunoprecipitating with a BMP type I receptor when antibodies specific for either h-BRK-3 or a BMP type I receptor are used.

As used herein, "truncated human BMP receptor kinase protein" or "t-BRK-3" means a protein having amino acid sequence SEQ ID NO:4, or a sequence having the properties described above for BRK-3.

As used herein, "mouse BMP receptor kinase protein" or "m-BRK-3" means a protein having amino acid sequence SEQ ID NO:8, or a sequence having the properties described above for BRK-3.

As used herein, "BRK-3" refers generally to h-BRK-3, t-BRK-3 and m-BRK-3, or a substantially similar BMP receptor kinase protein.

As used herein, "substantially similar" when used to define either amino acid or nucleic acid sequences, means that a particular subject sequence, for example, a sequence altered by mutagenesis, varies from a reference sequence by one or more substitutions, deletions, or additions, the net effect of which is to retain biological activity of the BRK-3 protein. Alternatively, nucleic acid sequences and analogs are "substantially similar" to the specific DNA sequence disclosed herein if the DNA sequences, as a result of degeneracy in the genetic code, encode an amino acid sequence substantially similar to the reference amino acid sequence. In addition, "substantially similar" means a receptor protein that will react with antibodies generated against the BRK-3 protein or peptides derived from the protein sequence of BRK-3.

As used herein, "biologically active" means that a particular molecule shares sufficient amino acid sequence similarity with the embodiments of the present invention disclosed herein to be capable of binding detectable quantities of BMP-2 or BMP-4, or transmitting a BMP-2 or BMP-4 stimulus to a cell, for example, as a component of a hybrid receptor construct. Preferably, biologically active BRK-3 within the scope of the present invention means the receptor protein is capable of binding [$^{125}$I]-BMP-4 with nanomolar or subnanomolar affinity ($K_d$ approximately equal to $10^{-9}$M). Preferably, the affinity is from about $1\times10^{-10}$M to $1\times10^{-9}$M, with a proportion of binding sites exhibiting a $K_d$ less than $10^{-10}$M.

As used herein, "soluble fragment" refers to an amino acid sequence corresponding to the extracellular region of BRK-3 which is capable of binding BMPs. Soluble fragments include truncated proteins wherein regions of the receptor molecule not required for BMP binding have been deleted. Examples of such soluble fragments of the present invention include, but are not limited to, polypeptides having the amino acid sequences substantially similar to SEQ ID NO:6; SEQ ID NO:10; amino acid residues 1–150 depicted in SEQ ID NO:2; amino acid residues 1–150 depicted in SEQ ID NO:8; or polypeptides encoded by nucleic acid residues substantially similar to SEQ ID NO:5; SEQ ID NO:9; nucleic acid residues 409–858 depicted in SEQ ID NO:1, or nucleic acid residues 17–466 depicted in SEQ ID NO:7.

As used herein, "digit-removed BMP-2" and "DR-BMP-2" refer to a fragment of BMP-2 protein wherein the amino terminus of mature BMP-2 has been removed by mild trypsin digestion (B. B. Koenig et al., *Molecular and Cellular Biology*, 14: 5961–5974 (1994)).

As used herein, "isolated", in reference to the receptor protein of the present invention or DNA sequences encoding said protein, means that the protein or DNA sequence is removed from the complex cellular milieu in which it naturally occurs, and said protein is expressible from said DNA sequence in a cell that does not naturally express it when operably linked to the appropriate regulatory sequences.

As used herein, "operably linked" refers to a condition in which portions of a linear DNA sequence are capable of influencing the activity of other portions of the same linear DNA sequence. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous in reading frame.

As used herein, "ATCC" means American Type Culture Collection, Rockville, Md.

As used herein, "bone morphogenetic protein 2" or "BMP-2" means a peptide encoded by a DNA sequence contained in ATCC No. 40345 (see ATCC/NIH REPOSITORY CATALOGUE OF HUMAN AND MOUSE DNA PROBES AND LIBRARIES, sixth Edition, 1992, p. 57, hereinafter "ATCC/NIH REPOSITORY CATALOGUE"). Isolation of BMP-2 is disclosed in U.S. Pat. No. 5,013,649, Wang, Wozney and Rosen, issued May 7, 1991; U.S. Pat. No. 5,166,058, Wang, Wozney and Rosen, issued Nov. 24, 1992; and U.S. Pat. No. 5,168,050, Hammonds and Mason, issued Dec. 1, 1992; each of which is incorporated herein by reference.

As used herein, "bone morphogenetic protein 4" or "BMP-4" means a peptide encoded by a DNA sequence contained in ATCC No. 40342 (see ATCC/NIH REPOSITORY CATALOGUE). Isolation of BMP-4 is disclosed in U.S. Pat. No. 5,013,649, Wang, Wozney and Rosen, issued May 7, 1991, incorporated herein by reference.

As used herein, "bone morphogenetic protein 7" or "BMP-7" means a peptide encoded by a DNA sequence contained in ATCC No. 68020 and ATT 68182 (see ATCC/NIH Repository Catalogue), where the cDNA in ATCC 68182 is claimed to contain all of the nucleotide sequences necessary to encode BMP-7 proteins. Isolation of BMP-7 is disclosed in U.S. Pat. No. 5,141,905, issued Aug. 25, 1992, to Rosen, et al., which is incorporated herein by reference.

As used herein, a "BMP Type I Receptor Kinase" is a protein capable of binding BMP-2, BMP-4 and/or other known BMPs, and bears sequence characteristics of a type I receptor including, but not limited to, an extracellular ligand binding domain containing a cysteine box and an upstream cysteine box, an SGSGSG motif, designated the GS domain, in the intracellular juxtamembrane region, an intracellular kinase domain that is > about 85% similar to other type I receptors for other ligands in the TGF-β superfamily, and/or a relatively short carboxy terminus. As used herein, "BMP Type I Receptor Kinase" also includes receptor proteins having the characteristics of a BMP type I receptor as described in the literature, such as in: B. B. Koenig et al., *Molecular and Cellular Biology*, 14: 5961–5974 (1994); L. Attisano, et al., *Biochimica et Biophysica Acta*, 1222: 71–80 (1994); J. Massagué, L. Attisano, and J. L. Wrana, *Trends in Cell Biology*, 4: 172–178 (1994); and ten Dijke, et al., *J. Biological Chemistry*, 269: 16985–16988 (1994).

Examples of BMP type I receptors include, but are not limited to: BRK-1 (B. B. Koenig et al., *Molecular and Cellular Biology*, 14: 5961–5974 (1994)); BRK-2, also referred to as RPK-1 (S. Sumitomo, T. Saito, and T. Nohno, *DNA Sequence*, 3: 297–302 (1993); ALK-2, which has been shown to be a receptor for BMP-7 (ten Dijke et al., *J. Biological Chemistry*, 269: 16985–16988 (1994)); the *Xenopus* BMP type I receptor that binds BMP-2 and BMP-4 and which is involved in mesoderm induction (J. M. Graff, R. S. Thies, J. J. Song, A. J. Celeste, and D. A. Melton, *Cell*, 79: 169–179 (1994)); and type I receptors from Drosophila that bind the decapentaplegic peptide, which is the *Drosophila* homologue of BMP-2 and BMP-4. These Drosophila receptors are designated 25D1, 25D2, and 43E (T. Xie, A. L. Finelli, and R. W. Padgett, *Science*, 263: 1756–1759 (1994); A. Penton, Y. Chen, K. Staehling-Hampton, J. L. Wrana, L. Attisano, J. Szidonya, A. Cassill, J. Massagué, and F. M. Hoffmann, *Cell*, 78: 239–250 (1994); and T. Brummel, V. Twombly, G. Marques, J. Wrana, S. Newfeld, L. Attisano, J. Massagué, M. O'Connor, and W. Gelbart, *Cell*, 78: 251–261 (1994)).

As used herein, "DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences (introns) which are typically present in eukaryotic genes. Genomic DNA containing the relevant sequences could also be used. Sequences of non-translated DNA may be present 5' or 3' from the open reading frame, where the same do not interfere with manipulation or expression of the coding regions. DNA sequences encoding the proteins provided by this invention can be assembled from cDNA fragments and short oligonucleotide linkers, or from a series of oligonucleotides, to provide a synthetic gene which is capable of being expressed in a recombinant transcriptional unit.

As used herein, "recombinant" means that a protein is derived from a DNA sequence which has been manipulated in vitro and introduced into a host organism.

As used herein, "microbial" refers to recombinant proteins made in bacterial, fungal (e.g., yeast), or insect expression systems.

As used herein, "recombinant expression vector" refers to a DNA construct used to express DNA which encodes a desired protein (for example, BRK-3) and which includes a transcriptional subunit comprising an assembly of 1) genetic elements having a regulatory role in gene expression, for example, promoters and enhancers, 2) a structural or coding sequence which is transcribed into mRNA and translated into protein, and 3) appropriate transcription and translation initiation and termination sequences. Using methodology well known in the art, recombinant expression vectors of the present invention can be constructed. Possible vectors for use in the present invention include, but are not limited to: for mammalian cells, pJT4 (discussed further below), pcDNA-1 (Invitrogen, San Diego, Calif.) and pSV-SPORT 1 (Gibco-BRL, Gaithersburg, Md.); for insect cells, pBlueBac III or pBlueBacHis baculovirus vectors (Invitrogen, San Diego, Calif.); and for bacterial cells, pET-3 (Novagen, Madison, Wis.). The DNA sequence coding for a BRK-3 protein receptor kinase of the present invention can be present in the vector operably linked to regulatory elements.

In one embodiment of the present invention, mammalian host cells are preferably transfected with the plasmid construct pJT6-mBRK-3L, thereby resulting in expression of m-BRK-3. In another embodiment of the present invention, mammalian host cells are preferably transfected with the plasmid construct, pJT4-hBRK3T, thereby resulting in expression of t-BRK-3. Transfection with the recombinant molecules can be effected using methods well known in the art.

As used herein, "host cell" means a cell comprising a recombinant expression vector of the present invention. Host cells may be stably transfected or transiently transfected within a recombinant expression plasmid or infected by a recombinant virus vector. The host cells include prokaryotic cells, such as *Escherichia coli*, fungal systems such as *Saccharomyces cerevisiae*, permanent cell lines derived from insects such as Sf-9 and Sf-21, and permanent mammalian cell lines such as Chinese hamster ovary (CHO) and SV40-transformed African green monkey kidney cells (COS).

In one embodiment, the present invention relates to a type II BMP receptor kinase protein, or soluble fragment thereof Preferably, the BMP receptor kinase protein is h-BRK-3, having an amino acid sequence SEQ ID NO: 2, or the soluble fragment thereof having an amino acid sequence SEQ ID NO: 6. Also preferred is the BMP receptor kinase protein m-BRK-3 having an amino acid sequence SEQ ID NO: 8, or the soluble fragment thereof having an amino acid sequence SEQ ID NO: 10. Also preferred is the BMP receptor kinase protein t-BRK-3 having an amino acid sequence SEQ ID NO: 4.

In another embodiment, the present invention relates to a DNA sequence coding or the h-BRK-3 receptor protein, or a soluble fragment thereof. (The DNA can be genomic or cDNA.) Preferably the h-BRK-3 protein is coded for by the nucleic acid sequence SEQ ID NO: 1; the soluble fragment thereof is preferably coded for by the nucleic acid sequence SEQ ID NO: 5.

In another embodiment, the present invention relates to a DNA sequence coding for the t-BRK-3 protein. (The DNA sequence can be genomic DNA or cDNA.) Preferably the DNA sequence is SEQ ID NO:3.

In another embodiment, the present invention relates to a DNA sequence coding for the m-BRK-3 protein, or a soluble fragment thereof (The DNA sequence can be genomic DNA or cDNA.) Preferably the m-BRK-3 protein is coded for by the DNA sequence SEQ ID NO:7; the soluble fragment is preferably coded for by the DNA sequence SEQ ID NO:9.

In another embodiment, the present invention relates to a recombinant expression vector comprising a DNA sequence coding for the m-BRK-3 protein. Preferably the recombinant expression vector is a plasmid having all of the identifying characteristics of the pJT6-mBRK-3S or pJT6-mBRK-3L plasmid constructs contained in ATCC No. 69694 and ATCC No. 69695, respectively. In another embodiment, the present invention relates to a host cell comprising the above described recombinant expression vector. Preferably the host cell is a mammalian cell; more preferably a CHO cell or COS cell, or a mink lung epithelial cell.

In another embodiment, the present invention relates to a recombinant expression vector comprising a DNA sequence coding for t-BRK-3. Preferably the recombinant expression vector is a plasmid having all of the identifying characteristics of the pJT4-hBRK3T plasmid construct contained in ATCC No. 69676. In another embodiment, the present invention relates to a host cell comprising the recombinant expression vector comprising a DNA sequence that codes for t-BRK-3. Preferably the host cell is a mammalian cell; more preferably a CHO cell or COS cell.

In another embodiment, the present invention relates to a recombinant expression vector comprising a DNA sequence coding for h-BRK-3. In another embodiment, the present invention relates to a host cell comprising the recombinant expression vector comprising a DNA sequence that codes for h-BRK-3. Preferably the host cell is a mammalian cell; more preferably a CHO cell or COS cell.

In another embodiment, the present invention relates to a method for producing BRK-3, t-BRK-3, or m-BRK-3 comprising isolating BRK-3, t-BRK-3, or m-BRK-3 from the host cell described above.

The BMP type II receptor of the present invention is useful for identifying compounds (e.g., BMP (preferably BMP-2, BMP-4, or BMP-7), or other as yet to be discovered compounds) capable of binding to a BMP receptor kinase protein, the method comprising introducing a sample comprising the compound to the BMP type II receptor kinase protein of the present invention that is expressed in a cell, and allowing the compound to bind to the receptor kinase protein. Preferably the type II receptor kinase protein has amino acid sequence SEQ ID NO:2 (h-BRK-3) or a soluble fragment thereof, or SEQ ID NO:8 (m-BRK-3) or SEQ ID NO:4 (t-BRK-3) or soluble fragment thereof. Such a method is also useful for determining the amount of BMP or other receptor binding compound present in the sample.

For example, BMP concentration in a sample can be determined by radioreceptor assay, in which unlabeled BMP in the sample competes with labeled tracer BMP for binding to the BRK-3 receptor. As described in co-pending application U.S. Ser. No. 08/334,178, filed by Rosenbaum on Nov. 4, 1994, the BRK-3 receptor of the present invention may be complexed to a BMP type I receptor. As the amount of BMP in esample increases, it reduces the amount of labeled BMP which is able to bind to BRK-3 or a receptor protein complex comprising BRK-3. Comparison with a standard curve prepared with known concentrations of unlabeled BMP allows accurate quantitation of BMP concentration in the sample. Labeling of tracer BMP is preferably done by iodination with [$^{125}$I]NaI. BRK-3 can be expressed in the outer membrane of a stable cell line, or supplied as a soluble fragment, or as a soluble fragment covalently attached to a solid support. To perform the assay, unlabeled BMP from the sample and labeled tracer BMP compete for binding to the receptor until equilibrium is reached. The receptor-BMP complex is then isolated from free ligand, for example by washing (in the case of an adherent cell line), rapid filtration or centrifugation (in the case of a nonadherent cell line or receptor bound to a solid support), or precipitation of the receptor-ligand complex with antibodies, polyethylene glycol, or other precipitating agent followed by filtration or centrifugation (in the case of a soluble receptor). The amount of labeled BMP in the complex is then quantitated, typically by gamma counting, and compared to known standards. These methods have been described in the literature using other receptors (M. Williams, *Med. Res. Rev.*, 11: 147–184 (1991); M. Higuchi and B. B. Aggarwal, *Anal. Biochem.*, 204: 53–58 (1992); M. J. Cain, R. K. Garlick and P. M. Sweetman, *J. Cardiovasc. Pharm.*, 17: S150–S151 (1991); each of which are incorporated herein by reference), and are readily adapted to the BRK-3 receptor/BMP system. Such a radioreceptor assay can be used for diagnostic purposes for quantitation of BMP in clinical samples, where such quantitation is necessary.

The BMP type II receptor protein of the present invention is also useful in high-throughput screens to identify compounds capable of binding to BRK-3, or a homologous receptor protein. In such a method, the higher the affinity of the compound for BRK-3, the more efficiently it will compete with the tracer for binding to the receptor, and the lower the counts in the receptor-ligand complex. In this case, one compares a series of compounds at the same concentration range to see which competed for receptor binding with the highest affinity.

This invention is useful for determining whether a ligand, such as a known or putative drug, is capable of binding to and/or activating the receptors encoded by the DNA molecules of the present invention. Transfection of said DNA sequence into the cell systems described herein provides an assay system for the ability of ligands to bind to and/or activate the receptor encoded by the isolated DNA molecule. Recombinant cell lines, such as those described herein, are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for competitive binding assays. Soluble receptors derived from the ligand binding domain of the receptor can also be employed in high throughput screening of drug candidates. Functional assays of intracellular signaling can act as assays for binding affinity and efficacy in the activation of receptor function. In addition, the recombinant cell lines may be modified to include a reporter gene operably linked to a response element such that a signal sent by the receptor turns on the reporter gene. Such a system is especially useful in high throughput screens directed at identification of receptor agonists. These recombinant cell lines constitute "drug discovery systems", useful for the identification of natural or synthetic compounds with potential for drug development. Such identified compounds could be further modified or used directly as therapeutic compounds to activate or inhibit the natural functions of the receptor encoded by the isolated DNA molecule.

The present invention relates to a receptor-reporter system to identify compounds which will alter transcription of the gene for the BMP type II receptor BRK-3, thereby acting as indirect BRK-3 receptor agonists or antagonists. The reporter system for evaluating whether test compounds are capable of acting as agonists of the BMP type II receptor protein kinase BRK-3, or functionally modified forms thereof, comprises:
  (a) culturing cells containing:
    (i) DNA encoding BRK-3 protein, or functionally modified forms thereof, and
    (ii) DNA encoding a hormone response element operatively linked to a reporter gene,
  wherein the culturing is carried out in the presence of at least one test compound whose ability to induce the transcriptional activity of BRK-3 protein is sought to be determined, and thereafter (b) monitoring the cells for expression of the reporter gene.

The reporter system for evaluating whether test compounds are capable of acting as antagonists of the BMP type II receptor protein kinase BRK-3, or functionally modified forms thereof, comprises:

(a) culturing cells containing:
   (i) DNA encoding BRK-3 protein, or functionally modified forms thereof, and
   (ii) DNA encoding a hormone response element operatively linked to a reporter gene,
wherein the culturing is carried out in the presence of:
   a fixed concentration of at least one agonist for transcription of BRK-3 or, functionally modified forms thereof, and increasing concentrations of at least one test compound whose ability inhibit transcriptional activation of the BRK-3 receptor protein is sought to be determined; and thereafter (b) monitoring in the cells the level of expression of the product of the reporter gene as a function of the concentration of the test compound, thereby indicating the ability of the test compound to inhibit activation of transcription.

Cell lines expressing a high number of the BMP type II receptor proteins, or a soluble form thereof, of the present invention are also useful as a source of protein for receptor purification. The purified receptor or its soluble form can then be used for high-throughput screening assays for the purposes described above. The purified receptor or its soluble form can also be used for determination of the structure of the BMP:BRK-3 complex, using X-ray crystallography or NMR techniques, which can then be used in rational design of BMP agonists or antagonists. In addition, the purified receptor or its soluble form can be used in combination with a type I receptor or its soluble form for determination of the structure of a BMP:BRK-3:type I receptor complex. The soluble receptor proteins can also be used therapeutically as an agonist or antagonist of BMP function in vivo.

The present invention also relates to antibodies generated against the BMP type II receptor kinase proteins of the present invention. Such antibodies can be prepared by employing standard techniques as are well known to those skilled in the art, using the BMP type II receptor kinase protein of the present invention as antigens for antibody production. These antibodies can be employed for diagnostic applications, therapeutic applications, and the like. Preferably for therapeutic applications, the antibodies will be monoclonal antibodies.

The soluble receptor proteins of the present invention and the antibodies of the invention can be administered in a clinical setting using methods such as by intraperitoneal, intramuscular, intravenous, or subcutaneous injection, implant or transdermal modes of administration, and the like. Such administration can be expected to provide therapeutic alteration of the activity of the BMPs.

The nucleotide sequences disclosed herein, SEQ ID NO:3 and SEQ ID NO:1, represent the sequence of the DNA that codes for t-BRK-3 and h-BRK-3, respectively, isolated from human skin fibroblasts. SEQ ID NO:7 represents the DNA sequence coding for m-BRK-3 receptor protein from mouse NIH3T3 cells. These sequences could be readily used to obtain the cDNA for BRK-3 from other species, including, but not limited to, rat, rabbit, Drosophila, and Xenopus. These cDNA sequences can also be readily used to isolate the genomic DNA for BRK-3. This would permit analysis of the regulatory elements controlling receptor gene expression, which may offer new opportunities for therapeutic intervention and disease diagnosis. The nucleotide sequences are also useful to determine the distribution of the BRK-3 receptor in normal tissues and in disease states, which allows an assessment of its physiological role in vivo.

For purposes of illustrating a preferred embodiment of the present invention, the following non-limiting examples are discussed in detail.

EXAMPLE 1

Generation of PCR Fragments

In order to generate a PCR fragment of type II receptors related to the TGF-β type II receptor, primers shown in FIG. 1 are designed from the kinase domains of the TGF-β type II receptor. For the first round of PCR, the primers are TSK-1, derived from kinase domain II, and TSK-2, derived from kinase domain VIII. The template DNA consists of cDNA prepared from mRNA isolated from human skin fibroblasts from a 9 month old male. The PCR reaction, carried out in a total volume of 50 μl, contains approximately 0.2 μg of this cDNA, primers TSK-1 and TSK-2 at a concentration of 15 μM, stocks of all four deoxynucleotides at a concentration of 0.2 mM each, 1.5 unit of DNA polymerase from *Thermus thennophilus* (hereafter, Tth polymerase) (Toyobo, Osaka, Japan) and reaction buffer for the Tth polymerase (Toyobo, Osaka, Japan). After an initial melting period of 1 min at 94° C., the temperature cycle is carried out as follows for 35 cycles: melting, 92° C. for 40 sec; annealing, 48° C. for 40 sec; extension, 75° C. for 90 sec. After the 35th cycle, the reaction is held at 75° C. for an additional 5 min to complete the extension.

Several bands are amplified, including some in the area of 470 base pairs (bp) corresponding to the predicted sequence length of a type II receptor homologous to the TGF-β type II receptor. Accordingly, fragments in this size range are recovered from an agarose gel using QLAEX (Qiagen, Chatsworth, Calif., a kit for gel purification of DNA fragments, including activated silica spheres and buffers) according to the manufacturer's instructions, then resuspended in 10 mM Tris, pH 8.0, 1 mM EDTA (TE) in a volume of 20 μl.

To reduce the background from fragments amplified from cDNAs not related to the TGF-β type II receptor, a second round of PCR is carried out using "nested" primers based on conserved regions of the TGF-β type II receptor located within the 470 bp region amplified in the first round. The nested primers are AVR-5, derived from kinase domain IV of the TGF-β type II receptor, and TSK-4, derived from kinase domain VIB (FIG. 1). The template consists of an aliquot (0.5 μl) of the PCR fragments isolated from the first round of PCR. To this is added the primers AVR-5 (5 μM) and TSK-4 (15 μM), all four deoxynucleotides (0.2 mM each), 1.5 units of Tth DNA polymerase, and reaction buffer for the Tth DNA polymerase, in a total volume of 50 μl. The temperature cycle program is executed exactly as described above for the first round of PCR. Agarose gel electrophoresis of the PCR reaction products shows amplification of a band in the range of 300 bp, as expected. This fragment is isolated using QIAEX.

In order to subclone the PCR product of the second PCR reaction, the purified fragment is phosphorylated using polynucleotide kinase and ligated to the cloning vector pGEM7Zf (+) (Promega, Madison, Wis.) which has previously been cut with Sma I and dephosphorylated. The ligation mix is used to transform *E. coli* XL 1-Blue (Stratagene, La Jolla, Calif.). When the transformation mix is plated on agar containing isopropyl-β-D-thiogalactoside (IPTG) and 5-bromo-4-chloro-3-indolyl-β-D-galactoside (X-gal), colonies are obtained which lack blue color, indicating the presence of an insert. Plasmid DNA is prepared from a selection of these colonies. Three of the candidate plasmids, designated HSK7-1, HSK7-2, and HSK7-4 are found to have inserts of the expected size (300 bp). Upon sequencing of the inserts, the 300 bp insert from HSK7-2 is found to encode a portion of a novel kinase that is predicted to be a novel member of the TGF-β receptor superfamily. Accordingly, the HSK7-2 PCR fragment is used as a probe to isolate the full-length receptor clone.

EXAMPLE 2

Isolation of Human t-BRK-3 cDNA

In order to locate the cDNA corresponding to the 300 bp insert in HSK7-2, a cDNA library is constructed from the same mRNA used to isolate the PCR fragment. This is accomplished using the SUPERSCRIPT Choice System (Life Technologies, Gaithersburg, Md.; a kit for cDNA synthesis, including primers, adapters, SUPERSCRIPT II RNAse H⁻ Reverse Transcriptase (Life Technologies, Gaithersburg Md.; a modified form of reverse transcriptase from Moloney murine leukemia virus), enzymes, nucleotides, buffers, and gel filtration columns) according to the manufacturer's instructions, except that 180 units of RNase inhibitor (Takara, Kyoto, Japan) is added to the first strand synthesis. The template is mRNA (4 µg) from human skin fibroblasts from a 9 month old male. A total of 4 µg of cDNA is obtained after first and second strand synthesis. This is followed by the addition of Eco RI adapters (supplied with the kit) which contain internal Not I and Sal I sites. The Eco RI-adapted cDNA is then phosphorylated and subjected to size fractionation according to the manufacturer's instructions, using gel filtration columns provided with the kit.

The size fractionated cDNA is ligated into the Eco RI site of the phage λgt10, and packaged in vitro with GIGAPACK II Gold Packaging Extract (Stratagene, La Jolla, Calif.; a restriction-minus in vitro packaging extract for high-efficiency construction of cDNA libraries in λ phage) according to the manufacturer's instructions. A total of $8.1 \times 10^5$ phages are obtained.

The library is screened on ten HYBOND Nylon membranes (Amersham, Arlington Heights, Ill.; nylon membranes optimized for immobilization of nucleic acids), at a density of $1 \times 10^5$ plaques/filter. The insert from HSK7-2 is labeled with the MULTIPRIME DNA Labeling System (Amersham, Arlington Heights, Ill.; a kit for random primer labeling of DNA, including Klenow DNA polymerase, primers, and buffers) according to the manufacturer's instructions. The labeled probe is allowed to hybridize to the library filters in 50% formamide, 6×SSPE (1×SSPE=0.14 M NaCl, 8 mM sodium phosphate, 0.08 mM EDTA, pH 7.7), 5×Denhardt's solution (1×Denhardt's=0.02% Ficoll type 400, 0.02% polyvinylpyrrolidone, 0.02% BSA), 0.5% sodium dodecyl sulfate (SDS), and 100 µg/ml denatured salmon sperm DNA at 42° C. for 12 hr. The blot is then washed in 2×SSPE, 0.1% SDS three times at room temperature (15 minutes each), followed by a 1 hr wash at 42° C.

After three rounds of screening, 3 independent clones are obtained. One of the clones, designated HSK723, is found to encode the same sequence as the HSK7-2 insert. Complete DNA sequence is obtained for this clone. The cDNA from this clone is designated t-BRK-3.

EXAMPLE 3 t-BRK-3 Sequence Analysis

The DNA sequence of this t-BRK-3 clone is shown in SEQ ID NO: 3, and the deduced protein sequence of t-BRK-3 in SEQ ID NO: 4. The t-BRK-3 open reading frame derived from clone HSK723 encodes a protein of at least 583 amino acids. No stop codon is observed to be located in-frame in the 3' region of the HSK723 cDNA, indicating that this clone is incomplete at the 3' end. It is thus designated t-BRK-3.

The deduced protein sequence of t-BRK-3 shown in SEQ ID NO: 4 is searched against all translated protein sequences in GenBank Release 84.0, dated Aug. 15, 1994, using a standard Needleman-Wunsch algorithm (S. B. Needleman and C. D. Wunsch, *J. Mol. Biol.* 48: 443–453 (1970)), and is found to represent a novel sequence.

Analysis of the predicted protein sequence reveals a predicted structure of a TGF-β type II superfamily member transmembrane serine/threonine kinase. The predicted single transmembrane region encompasses residues 151–172 in SEQ ID NO:4. Three potential N-linked glycosylation sites are located at amino acid residues 55, 110, and 126 in the predicted extracellular domain. Amino acids 116–123 in SEQ ID NO:4 contain the cluster of cysteine residues called the "cysteine box" that is a characteristic of receptors for ligands of the TGF-β superfamily. The cysteine box of t-BRK-3 is identical in 6 of 8 amino acid residues to the cysteine box of the DAF-4 type II receptor for BMP-2 and BMP-4. However, the overall sequence identity of t-BRK-3 to DAF-4 in the extracellular domain is only 7.1%.

Amino acids 200–504 (in SEQ ID NO: 4) in the predicted cytoplasmic region of t-BRK-3 contains all of the consensus sequences that characterize a protein kinase domain with predicted specificity for serine/threonine residues (S. K. Hanks, A. M. Quinn, and T. Hunter, *Science*, 241: 42–52 (1988)).

EXAMPLE 4

Construction of Expression Vectors for t-BRK-3, BRK-1, BRK-2, and DAF-4

In order to express t-BRK-3 in mammalian cells, it is subcloned into the vector pJT4, designed for transient expression. The pJT4 vector, optimized for transient expression in COS cells, includes the cytomegalovirus early promoter and enhancer, which gives very efficient transcription of message; an "R" element from the long terminal repeat of the human T-cell leukemia virus-1, which has been shown to increase expression levels further; an intron splice site from SV40, which is believed to enhance message stability; a multiple cloning site; a polyadenylation signal derived from SV40, which directs the addition of a poly A tail to the message, as is required for most eukaryotic mRNA; and the SV40 origin of replication, which permits the replication of the plasmid to extremely high copy number in cells which contain the SV40 large T antigen, such as COS cells. In addition, for manipulation and amplification of the vector in bacteria, the vector contains an *E. coli* origin of replication and an ampicillin resistance gene. Insertion of the truncated human BRK-3 cDNA into pJT4 is accomplished as follows.

Since no stop codon had been identified in the 3' region of the kinase domain, PCR is performed to insert a stop codon to permit translation of the protein. Accordingly, a PCR primer is designed to insert two stop codons after nucleotide 2028 in SEQ ID NO: 3, thus terminating the kinase after Ile 540 in SEQ ID NO: 4. This is chosen to correspond to the length of the activin type II receptor (L. S. Mathews and W. V. Vale, *Cell*, 65: 973–982 (1991)), so that it should be sufficient for proper folding of the kinase domain. The stop codons are followed by a Kpn I site. The complete sequence of the primer (which includes the reverse complement of nucleotides 2013–2028 in SEQ ID NO:3) is 5' ACG CGG TAC CTC ACT AAA TTT TTG GCA CAC GC 3'. A second primer is designed as an exact match to the t-BRK-3 sequence in the area of the Afl III site (nucleotides 1618–1637 in SEQ ID NO:3), having the sequence 5' GTA GAC ATG TAT GCT CTT GG 3'. The template for the reaction is clone HSK723, described in example 2, which contains the cDNA for t-BRK-3 in BLUESCRIPT II SK (+) (Stratagene, La Jolla, Calif.; a 2.96 kb colony-producing phagemid derived from pUC 19).

PCR is carried out using the GENE AMP PCR Kit with AMPLITAQ DNA Polymerase (Perkin Elmer, Norwalk, Conn.; a kit containing components necessary for amplification of DNA using the polymerase chain reaction, including AMPLITAQ, a recombinant modified form of the DNA polymerase from *Thermus aquaticus* (Perkin Elmer, Norwalk Conn.), nucleotides, and buffers), according to the manufacturer's instructions, using a GENE AMP PCR System 9600 Thermocycler (Perkin Elmer, Norwalk, Conn.). An initial melting at 95° C. for 5 min is followed by 20 cycles of the following program: melting at 95° C. for 1 min, annealing at 50° C. for 1 min, and extension at 72° C. for 1 min. After the last cycle, the temperature is held at 72° C. for an additional 2 min to complete extension.

The resulting amplified band, at the expected size of 400 bp, is isolated from an agarose gel and digested with Afl III and Kpn I. Meanwhile, the cDNA for t-BRK-3 is digested with Eco RV and Afl III, and the vector pJT4 is digested with Eco RV and Kpn I. These three isolated fragments are ligated in a single step to give the construct pJT4-hBRK3T, shown in FIG. 2. To confirm that no errors are introduced during PCR, the region from the Afl III site to the KpnI site at the 3' end is sequenced using the TAQ DYE DEOXY Terminator Cycle Sequencing Kit (Applied Biosystems, Foster, Calif.; kit containing components for automated DNA sequencing using the dideoxy terminator method, including AMPLITAQ, nucleotide mix, dye-labeled dideoxy nucleotide terminators, and buffers) and an Applied Biosystems Model 373A Automated DNA Sequencer. No errors are found.

To determine the effects of co-expression of t-BRK-3 with type I BMP receptors, it is necessary to co-express the cDNA for t-BRK-3 with the cDNA for BRK-1 or the cDNA for BRK-2. The DNA sequence for mouse BRK-1 is shown in SEQ ID NO: 11, and the deduced amino acid sequence for mouse BRK-1 is shown in SEQ ID NO: 12. The DNA sequence for chicken BRK-2 is shown in SEQ ID NO: 13, and the deduced protein sequence shown for chicken BRK-2 is shown in SEQ ID NO: 14.

Figure 3:
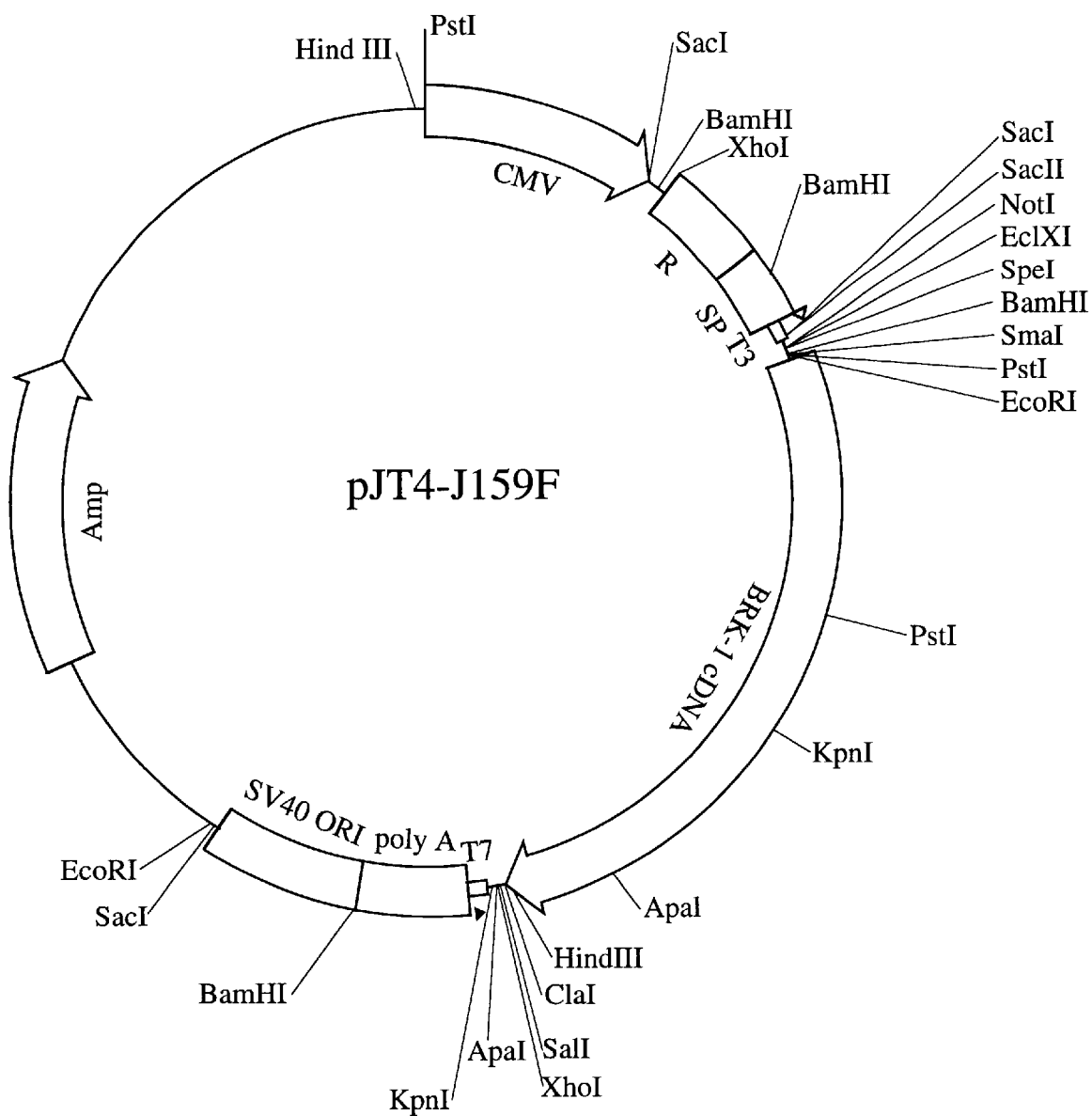
FIG. 3 shows the construct pJT4-J159F, used for transient mammalian expression of BRK-1. Abbreviations are the same as those in FIG. 2.

For mammalian expression of BRK-1, the plasmid pJT4-J159F is used. Construction of this plasmid is described in U.S. Ser. No. 08/158,735, filed Nov. 24, 1993 by Cook, et al. and B. B. Koenig et al., *Molecular and Cellular Biology* 14: 5961–5974 (1994); ATCC 69457. Briefly, the construct containing the BRK-1 cDNA subcloned in BLUESCRIPT SK (−) is linearized with the restriction endonuclease Alf III, and the overhanging end filled in using DNA Polymerase I Klenow fragment. The linearized plasmid is then digested with Not I, liberating the insert from the plasmid. The insert is then subcloned into the pJT4 expression vector at the Not I and EcoRV sites. The blunt end generated by the Klenow reaction is compatible with the EcoRV site, which is also a blunt end; ligation eliminates the Eco RV site. The construct pJT4-J159F is shown in FIG. 3.

Figure 4:
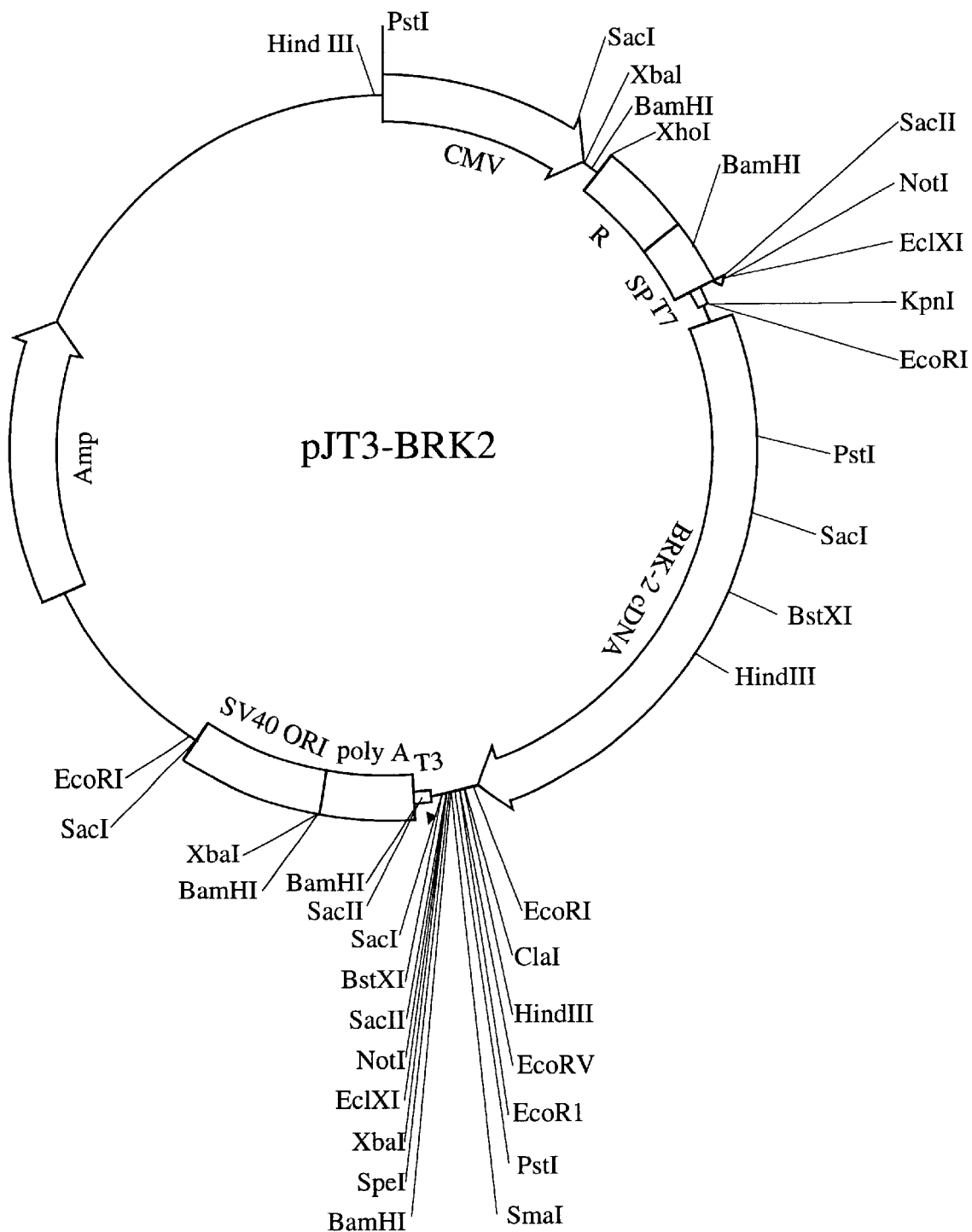
FIG. 4 shows the construct pJT3-BRK2, used for transient mammalian expression of BRK2. Abbreviations are the same as those in FIG. 2.

For mammalian expression of BRK-2, its cDNA is subcloned into the vector pJT3. This vector is identical to pJT4, described in this example, except that the multiple cloning site is in the opposite orientation, and an additional Not I site is present at the 5' end of the multiple cloning site. The cDNA for BRK-2 (see S. Sumitomo, et al., *DNA Sequence*, 3: 297–302 (1993)), originally obtained in the vector pRc/CMV (Invitrogen, San Diego, Calif.; a mammalian expression vector), is excised by digestion with Kpn I and Xho I. It is subcloned into pJT3 at the Kpn I and Sal I sites. This regenerates a Kpn I site at the 5' end of BRK-2, while the Xho I and Sal I sites are destroyed. The resulting construct is designated pJT3-BRK-2 and is shown in FIG. 4.

Figure 5:
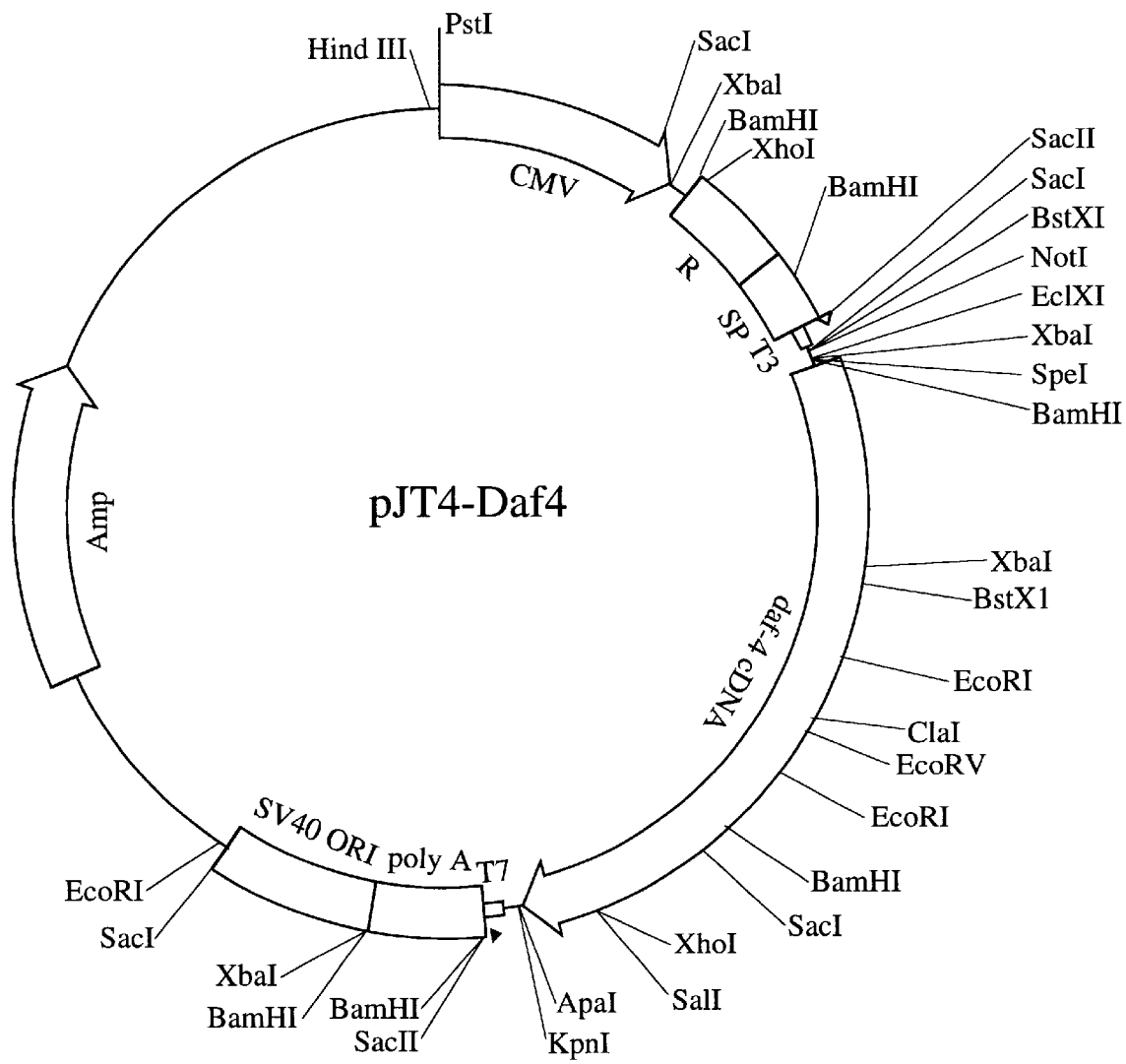
FIG. 5 shows the construct pJT4-Daf4, used for transient mammalian expression of the C. elegans receptor DAF-4. Abbreviations are the same as those in FIG. 2.

For mammalian expression of DAF-4, the type II BMP receptor from *Caenorhabditis elegans* (M. Estevez, L. Attisano, J. L. Wrana, P. S. Albert, J. Massagué, and D. L. Riddle, *Nature*, 365: 644–9 (1993), the cDNA is obtained in BLUESCRIPT II and subcloned into pJT4 as follows. A 2.4 kb fragment containing the daf-4 cDNA is excised by digestion with Dra I and Apa I. This fragment is subcloned into pJT4 at the Sma I and Apa I site. The Apa I site is regenerated, while the Dra I and Sma I sites are destroyed. This construct is designated pJT4-Daf4, and is shown in FIG. 5.

For mammalian expression of m-BRK-3, see Example 10, below.

EXAMPLE 5

Mammalian Expression of t-BRK-3, BRK-1, BRK-2, and DAF-4

Transient expression of BRK-3 in mammalian cells using pJT4-hBRK3T is carried out in COS-7 cells (ATCC CRL 1651) using electroporation or COS-1 cells (ATCC CRL 1650) using DEAE Dextran (Pharmacia Biotech, Piscataway, N.J.).

COS-7 cells are grown to confluence in Dulbecco's Modified Eagle (DME) high glucose media supplemented with 10% fetal bovine serum (Hyclone, Logan, Utah), nonessential amino acids (GIBCO, Gaithersburg, Md.), and glutamine, then trypsinized to release cells from the plate. The detached COS-7 cells are pelleted in a tabletop centrifuge, then resuspended in fresh media at a concentration of $6.25 \times 10^6$ cells/ml. The cell suspension ($5 \times 10^6$ cells, 0.8 ml) is transferred to the cuvette of a BioRad GENE PULSER electroporation system (BioRad, Hercules, Calif.). The purified plasmid containing the receptor DNA of interest (10 µg for pJT4-J159F and pJT3-BRK2 and/or 20 µg for pJT4-hBRK3T) is added to the cuvette, and the cells subjected to electroporation at 4.0 kV/cm, with a capacitance of 25 µFd. Cells are then plated (400,000 cells per well for 12 well plates and $5 \times 10^6$ cells for 100 mm plates) and allowed to recover. Fresh media is supplied after 24 hr. At 48 hr, cells are ready to be tested for binding of BMP-4.

For transient expression of BMP receptors in COS-1 cells, the cells are grown to approximately 50%–80% confluence in DME high glucose media supplemented with 10% fetal bovine serum (HyClone, Logan, Utah), nonessential amino acids, and glutamine in 100 mm plates. The cells are washed twice with 37° C. serum-free DME media, after which 4 ml of DNA mixture is added to each 100 mm plate. The DNA mixture contains DME, 10% Nu-Serum (Collaborative Biomedical Products, Bedford, Mass.), 400 µg/ml DEAE- Dextran (Pharmacia, Piscataway, N.J.), 0.1 mM chloroquine (Sigma, St. Louis, Mo.), and the cDNAs of interest: for t-BRK-3, 16 μg pJT4-hBRK3T; for BRK-1, 8 μg pJT4-J159F; for BRK-2, 8 μg pJT3-BRK2; for DAF-4, 16 μg pJT4-Daf4. The cells are then incubated at 37° C. with the DNA mixture for 3 hr. The solution is aspirated and the cells are incubated with 4 ml of a solution containing 10% dimethylsulfoxide (DMSO) in Dulbecco's phosphate buffered saline without calcium or magnesium (PBS; Life Technologies, Gaithersburg, Md.). After 2 min, the DMSO solution is aspirated, the cells are washed with the growth media described above, and fresh media is returned to the plates. The transfected cells are split into 12 well plates 24 hr post transfection for whole cell binding or cross linking. After 48 to 68 hr the cells are suitable for binding analysis.

EXAMPLE 6

Generation of the Radiolabeled BMP-4 Ligand

[$^{125}$I]-BMP-4 is prepared using IODOBEADS (Pierce, Rockford, Ill.; immobilized chloramine-T on nonporous polystyrene beads). Lyophilized BMP-4 (2 μg) is taken up in 50 μl of 10 mM acetic acid and added to 450 μl of phosphate-buffered saline (PBS) (Sigma, St. Louis, Mo.) on ice. To the tube is added 500 μCurie of $^{125}$I (Amersham, Arlington Heights, Ill.) (2200 Ci/mmol) in 5 μl, and one IODOBEAD. The reaction is incubated on ice for 10 min with occasional shaking. The reaction is then terminated by removal of the reaction from the IODOBEAD. To remove unreacted $^{125}$I, the mixture is applied to a PD-10 gel filtration column (Pharmacia, Piscataway, N.J.) previously equilibrated in 10 mM acetic acid, 0.1 M NaCl, 0.25% gelatin. The resulting labeled protein is >95% precipitable by trichloroacetic acid, indicating that all $^{125}$I is protein bound, and has a typical specific activity of 4000 to 9000 Ci/mmol.

Alternatively, BMP-4 is labeled with $^{125}$I by the chloramine-T method (C. A. Frolik, L. M. Wakefield, D. M. Smith, and M. B. Sporn, *J. Biol. Chem.*, 259: 10995–11000 (1984)). BMP-4 (2 μg) is taken up in 5 μl of 30% acetonitrile, 0.1% trifluoroacetic acid (TFA) plus an additional 5 μl of 1.5 M sodium phosphate, pH 7.4. Carrier free $^{125}$I (1 mCi, 9 μl) is added, together with 2 μl of a chloramine T solution (100 μg/ml). An additional 2 μl of the chloramine T solution is added at 2.0 min and at 3.5 min. After 4.5 minutes, the reaction is stopped by the addition of 10 μl of 50 mM N-acetyl tyrosine, 100 μl of 60 mM potassium iodide, and 100 μl of 11M urea, 1 M acetic acid. After a 3.5 minute incubation, unreacted iodine is removed on a PD-10 gel filtration column Pharmacia, Piscataway, N.J.) run in 4 mM HCl, 75 mM NaCl, 1 mg/ml bovine serum albumin (BSA). The resulting labeled protein is >95% precipitable by trichloroacetic acid, indicating that all $^{125}$I is protein bound, and has a typical specific activity of 3000–8000 Ci/mmol.

EXAMPLE 7

Characterization of BMP-4 Binding to t-BRK-3

Binding of BMP-4 to t-BRK-3 can be demonstrated by whole cell binding of radiolabeled BMP-4, and by covalent crosslinking of radiolabeled BMP-4 to the receptor. These two methods are described in detail below.

a. Whole Cell Binding:

COS-7 or COS-1 cells are transfected with pJT4-hBRK3T as described in example 5. After transfection, cells are seeded into 12 well plates and the binding experiments are carried out at 48 to 68 hr. At that time, cells are washed once with binding buffer (50 mM HEPES, pH 7.4, 128 mM NaCl, 5 mM KCl, 5 mM MgSO$_4$, 1.2 mM CaCl$_2$, 2 mg/ml BSA), then equilibrated in the same buffer at 4° C. for 30–60 min with gentle shaking. The buffer is then aspirated, and to each well is added 500 μl of binding buffer (4° C.), containing [$^{125}$I]-BMP-4 tracer (100–400 pM), as well as varying concentrations of unlabeled BMP-2, BMP-4, or other unlabeled ligand, depending on the assay. For determination of nonspecific binding, BMP-4 is added to the binding buffer at a final concentration of 10 to 50 nM. To prevent degradation of ligand during the incubation, a protease inhibitor cocktail is also added, to give a final concentration of 10 μg/ml leupeptin, 10 μg/ml antipain, 50 μg/ml aprotinin, 100 μg/ml benzamidine, 100 μg/ml soybean trypsin inhibitor, 10 μg/ml bestatin, 10 μg/ml pepstatin, and 300 μM phenylmethylsulfonyl fluoride (PMSF). The cells are incubated for 4 hr at 4° C. with gentle shaking. At the end of the incubation period, the buffer is aspirated, and the cells are rinsed 4 times with 1 ml washing buffer (50 mM HEPES, pH 7.4, 128 mM NaCl, 5 mM KCl, 5 mM MgSO$_4$, 1.2 mM CaCl$_2$, 0.5 mg/ml BSA). After the final wash is aspirated, 200 μl of solubilization buffer (10 mM Tris Cl, pH 7.4, 1 mM EDTA, 1% (v/v) Triton X-100) is added to each well and incubated at room temperature for 15–30 min. The solubilized cells are then transferred to fresh tubes and counted in a Packard Model 5005 COBRA Gamma Counter (Packard Instruments, Meriden, Conn.).

Figure 6:
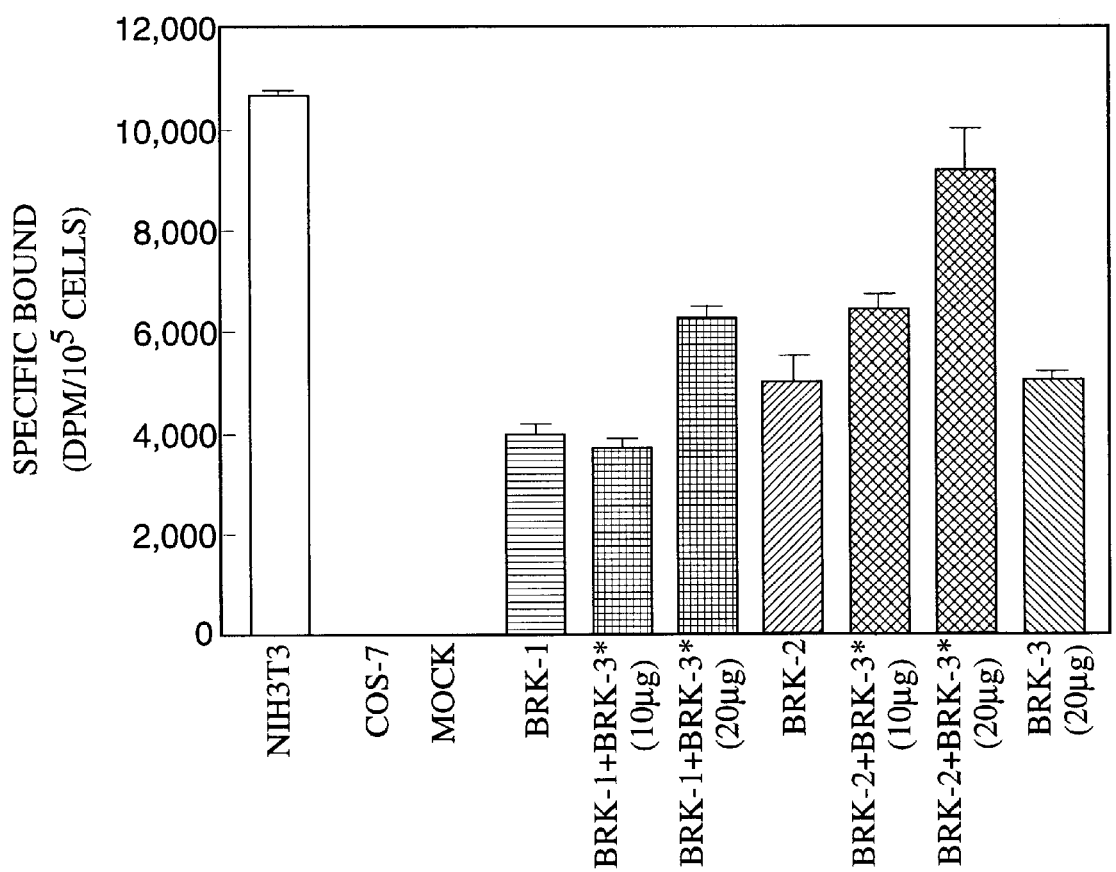
FIG. 6 shows whole cell binding of [$^{125}$I]-BMP-4 to t-BRK-3 expressed in COS-7 cells, in the presence or absence of the type I receptors BRK-1 and BRK2. Bars represent specific binding of [$^{125}$I]-BMP-4, normalized to cell number. Left to right, NIH3T3 embryonic fibroblasts; COS-7 cells; COS-7 cells transfected with the vector pJT-4 alone (designated "mock"); COS-7 cells transfected with BRK-1 alone, BRK-1 plus 10 or 20 μg of t-BRK-3, BRK-2 alone, BRK-2 plus 10 or 20 μg of t-BRK-3, and t-BRK-3 alone (20 μg).

Results are shown in FIG. 6, which shows specific binding of [$^{125}$I]-BMP-4 to NIH3T3 cells (ATCC CRL 1658), which display significant endogenous binding of BMP-4, and COS 7 cells transfected with the cDNA for t-BRK-3 in the presence and absence of BRK-1 and BRK-2. t-BRK-3 is capable of binding [$^{125}$I]-BMP-4 when expressed alone (bar on far right), at a level similar to that seen for BRK-1 and BRK-2 expressed alone. Binding of [$^{125}$I]-BMP-4 is increased by co-expression of t-BRK-3 with BRK-1, and to a greater extent by co-expression of t-BRK-3 with BRK-2.

b. Covalent Crosslinking:

Bifunctional crosslinking reagent disuccinimidyl glutarate (DSG) (Pierce, Rockford, Ill.) is used to covalently crosslink bound radiolabeled ligand to its receptor by reaction with free amino groups on lysine residues in the two proteins. Following the crosslinking, cellular proteins are separated by gel electrophoresis, and radioactive bands visualized. The labeled bands represent the receptor selectively "tagged" with the radiolabeled ligand. In this procedure, cells are transfected with the cDNA for BRK-3, and/or BRK-1 or BRK-2, as described in example 5, then seeded into 12 well plates. At 48–68 hr after transfection, the cells are washed, equilibrated, and incubated with [$^{125}$I]-BMP-4 and competing unlabeled ligands as described in this example for whole cell binding studies. After completion of the 4 hr incubation with ligand, the cells are washed two to three times at 4° C. with 2 ml of binding buffer having the same composition as described above, except that no BSA is added. To each well is then added 1 ml of fresh BSA-free binding buffer, followed by freshly prepared DSG to a final concentration of 135 μM. After swirling gently to mix the DSG, the plates are incubated for exactly 15 minutes at 4° C. with gentle shaking. At this point the media is aspirated and the cells washed with 3 ml detachment buffer (10 mM Tris base, 0.25 M sucrose, 1 mM EDTA, 0.3 mM PMSF) or PBS. Solubilization buffer (50 μl) is then added to each well and the cells are allowed to solubilize for 30–45 minutes at 4° C. with shaking. An aliquot of the sample (20 μl) is transferred to a fresh tube and 5 μl of 5× sample loading buffer (0.25 M TrisCl, pH 6.8, 10% SDS, 0.5 M DTT, 0.5% bromophenol blue, 50% glycerol; purchased from Five Prime Three Prime, Boulder, Colo.) is added. The samples are boiled for 5 min and centrifuged (13,0000×g, 5 min). The supernatants are loaded onto 7.5% SDS-polyacrylamide gels (Integrated Separation Systems, Natick, Mass.) and subjected to electrophoresis. The gels are stained in 0.12% Coomassie Blue R250, 5% methanol, 7.5% acetic acid; destained in 5% methanol, 7.5% acetic acid; then dried. Radioactivity on the dried gel is visualized and quantitated on a PHOSPHORIMAGER (Molecular Devices, Sunnyvale, Calif., a device for quantitation of radioactivity using stable phosphor screens), or subjected to autoradiography using Kodak X-OMAT AR autoradiography film (Kodak, Rochester, N.Y.).

Figure 7:
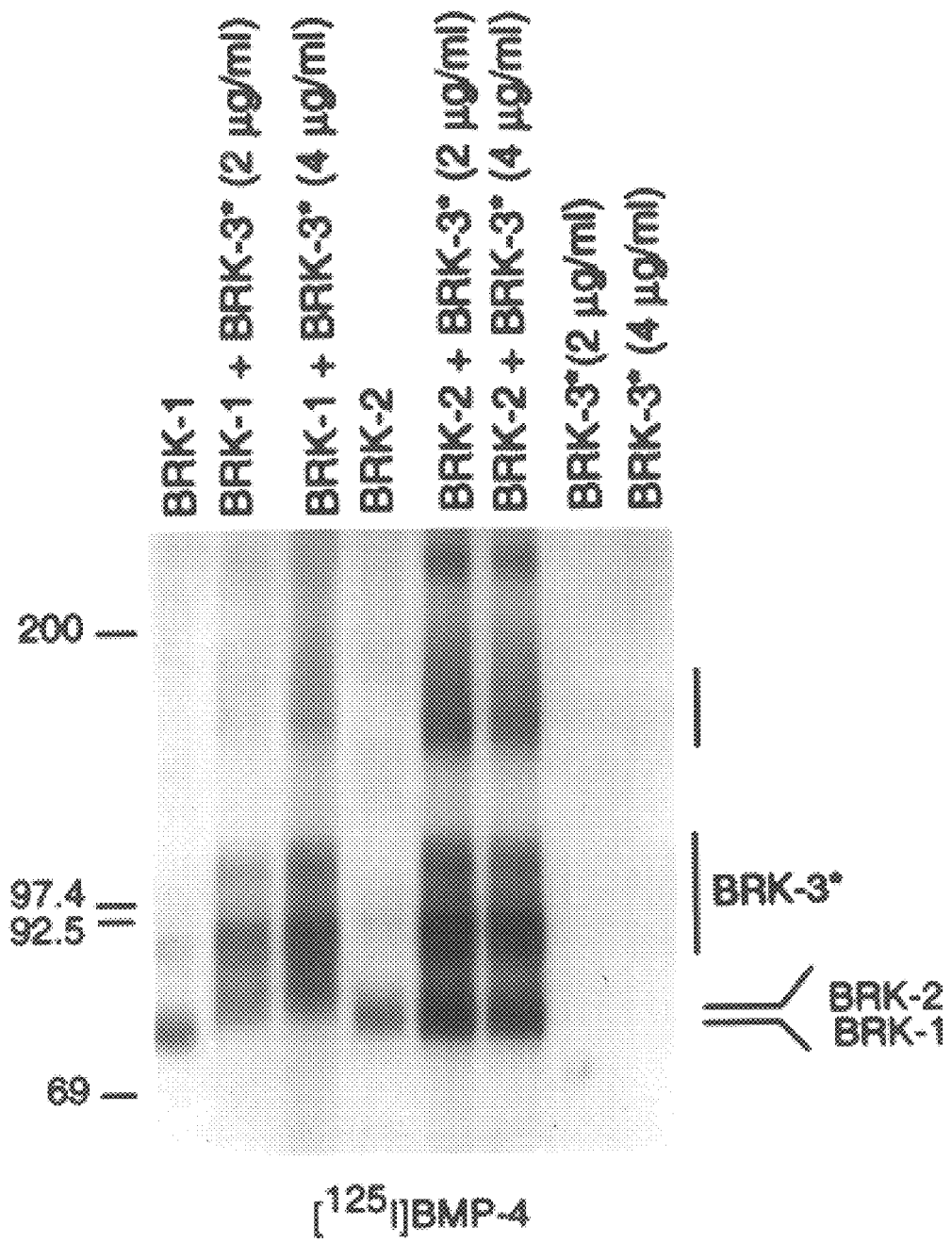
FIG. 7 shows crosslinking of [$^{125}$I]-BMP-4 to COS-1 cells transfected with t-BRK-3, in the presence or absence of the type I receptors BRK-1 and BRK-2. Molecular weight standards are shown on the left. Labels on the right indicate the bands which migrate at the predicted molecular weights of t-BRK-3, BRK-1, and BRK-2 crosslinked to [$^{125}$I]-BMP-4. Left to right, the lanes represent COS-1 cells transfected with BRK-1 alone; BRK-1 plus 2 μg/ml t-BRK-3; BRK-1 plus 4 μg/ml t-BRK-3; BRK-2 alone; BRK-2 plus 2 μg/ml t-BRK-3; BRK-2 plus 4 μg/ml t-BRK-3; t-BRK-3 alone at 2 μg/ml; and t-BRK alone at 4 μg/ml. Volume of DNA mixture is 4 ml. In this figure, "BRK-3*" is t-BRK-3.

Results are shown in FIG. 7. When t-BRK-3 is expressed alone in COS-1 cells, no crosslinked band is seen. Expression of BRK-1 alone results in a crosslinked band at a molecular weight of 78 kD, corresponding to the predicted molecular weight of BRK-1 plus the monomer molecular weight of BMP-4. Co-expression of t-BRK-3 and BRK-1 results in the appearance of a band of similar size to that for BRK-1, as well as a new crosslinked band at 94 kD, corresponding to the predicted molecular weight of t-BRK-3 plus the monomer molecular weight of crosslinked BMP-4. Similarly, expression of BRK-2 alone yields a single crosslinked band at 75 kD, corresponding to the predicted molecular weight of BRK-2 plus the crosslinked BMP-4 monomer. Co-expression of t-BRK-3 with BRK-2 yields a crosslinked band corresponding to that seen for BRK-2 alone, as well as a new crosslinked band at 94 kD, again corresponding to the predicted molecular weight of t-BRK-3 plus the monomer molecular weight of crosslinked BMP-4. Thus, crosslinking of [$^{125}$I]-BMP-4 to t-BRK-3 is observed only in the presence of a co-expressed type I BMP receptor.

EXAMPLE 8

Demonstration of Complex Formation with Type I BMP Receptors

Receptors of the TGF-β receptor family have been shown to form complexes involving a type I and a type II receptor (L. Attisano, J. L. Wrana, F. Lopez-Casillas, and J. Massagué, J. Biochim Biophys. Acta, 1222: 71–80 (1994)). In order to demonstrate that the type II BMP receptor t-BRK-3 can form a complex with the type I BMP receptors BRK-1 and BRK-2, COS-1 cells are co-transfected with the cDNA for t-BRK-3 and BRK-1, or t-BRK-3 and BRK-2, as described in Example 5. The receptors are crosslinked to [$^{125}$I]-BMP-4, then subjected to immunoprecipitation with antibodies specific for the type I receptors BRK-1 and BRK-2. If antibodies specific for a type I receptor precipitate not only the type I receptor crosslinked to [$^{125}$I]-BMP-4, but also BRK-3 crosslinked to [$^{125}$I]-BMP-4, this indicates that the two receptors must be forming a complex, as expected for type I and type II receptors having the same ligand-binding specificity.

Antibodies specific for the type I receptors BRK-1 and BRK-2 are generated using as antigen the peptide LNTRVGTKRYMAPEVLDESLNKNC (B. B. Koenig, et al., Molec. Cell. Biol., 14: 5961–5974 (1994)). This peptide is based on the amino acid sequence of BRK-1 in the intracellular kinase domain, amino acids 398–420 in SEQ ID NO: 12, with the addition of a cysteine at the C terminus to permit conjugation of the peptide. Comparison of the amino acid sequence of the kinase domain of BRK-1 with the kinase domain of the Raf protein suggests that this region of BRK-1 corresponds to a region of the Raf kinase which was used to make highly specific antibodies (W. Kolch, E. Weissinger, H. Mischak, J. Troppmair, S. D. Showalter, P. Lloyd, G. Heidecker, and U. R. Rapp, Oncogene, 5: 713–720 (1990)). This peptide is conjugated by standard methods to keyhole limpet hemocynanin, and used to immunize three New Zealand White rabbits (Hazleton Washington, Vienna, Va.). The resulting antisera are evaluated for their ability to recognize the original peptide coated on plastic, using an antibody capture ELISA. The antisera are designated 1378, 1379, and 1380. These antibodies are shown to immunoprecipitate BRK-1 from COS-7 cells transfected with the cDNA for BRK-1, using the procedure detailed in this example (B. B. Koenig, et al., Mol. Cell. Biol., 14: 5961–5974 (1994)). Because the sequence of BRK-2 is nearly identical to that of BRK-1 in this region, these antibodies are subsequently tested for their ability to immunoprecipitate BRK-2 as well, and are found to be effective for this purpose. Antibody 1379 gives superior results for immunoprecipitation of BRK-1, and antibody 1380 is preferred for immunoprecipitation of BRK-2.

In the immunoprecipitation procedure, COS-7 or COS-1 cells are transfected with the cDNA for t-BRK-3 and/or BRK-1, BRK-2, or DAF-4 as described in Example 5, and plated into 100 mm dishes. They are then crosslinked to [$^{125}$I]-BMP-4 as described in example 7, except that the incubation with [$^{125}$I]-BMP-4 and unlabeled ligand is carried out in a total of 4 ml, instead of 500 μl, and all other volumes are increased accordingly. Following the crosslinking, cells are washed three times with ice-cold PBS, then lysed with 1 ml of RIP buffer (20 mM TrisCl, pH 8.0, 100 mM NaCl, 1 mM Na$_2$EDTA, 0.5% Nonidet P-40, 0.5% sodium deoxycholate, 10 mM sodium iodide, and 1% bovine serum albumin) for 10 min. The lysate is centrifuged in a microcentrifuge at 13,000 rpm for 10 min at 4° C. The supernatant is transferred to a fresh tube and made 0.1% in SDS. To remove any existing antibody present in the lysate, 50 μl of PANSORBIN (Calbiochem, La Jolla, Calif.; a 10% solution of Staphylococcus aureus) is added. After a 30 minute incubation at 4° C., the lysate is centrifuged as before, and the supernatant again transferred to a fresh tube.

The primary antibody-1379 when cells are transfected with t-BRK-3 and BRK-1; 1380 when cells are transfected with t-BRK-3 and BRK-2—is then added to the tube at a final dilution of 1:100, and incubated for 2 hr on ice or overnight at 4° C. To precipitate the complex of antigen:primary antibody, 25–50 μl of PANSORBIN is then added and incubated 30 min on ice. The complex is pelleted at 13,000 rpm for 10 min in a microcentrifuge and the supernatant discarded. The pellet is washed twice in RIP buffer containing 0.1% SDS, and once in TNEN buffer (20 mM Tris, pH 8.0, 100 mM NaCl, 1 mM EDTA, 0.5% NP-40). The pellet is resuspended in 25 μl of 1× sample loading buffer. (Alternatively, the pellet may be washed twice with TNEN buffer, with similar results.) The sample is boiled for 5 min, centrifuged for 5 min, and subjected to gel electrophoresis after loading of the samples onto a 7.5% SDS-polyacrylamide gel.

Figure 8:
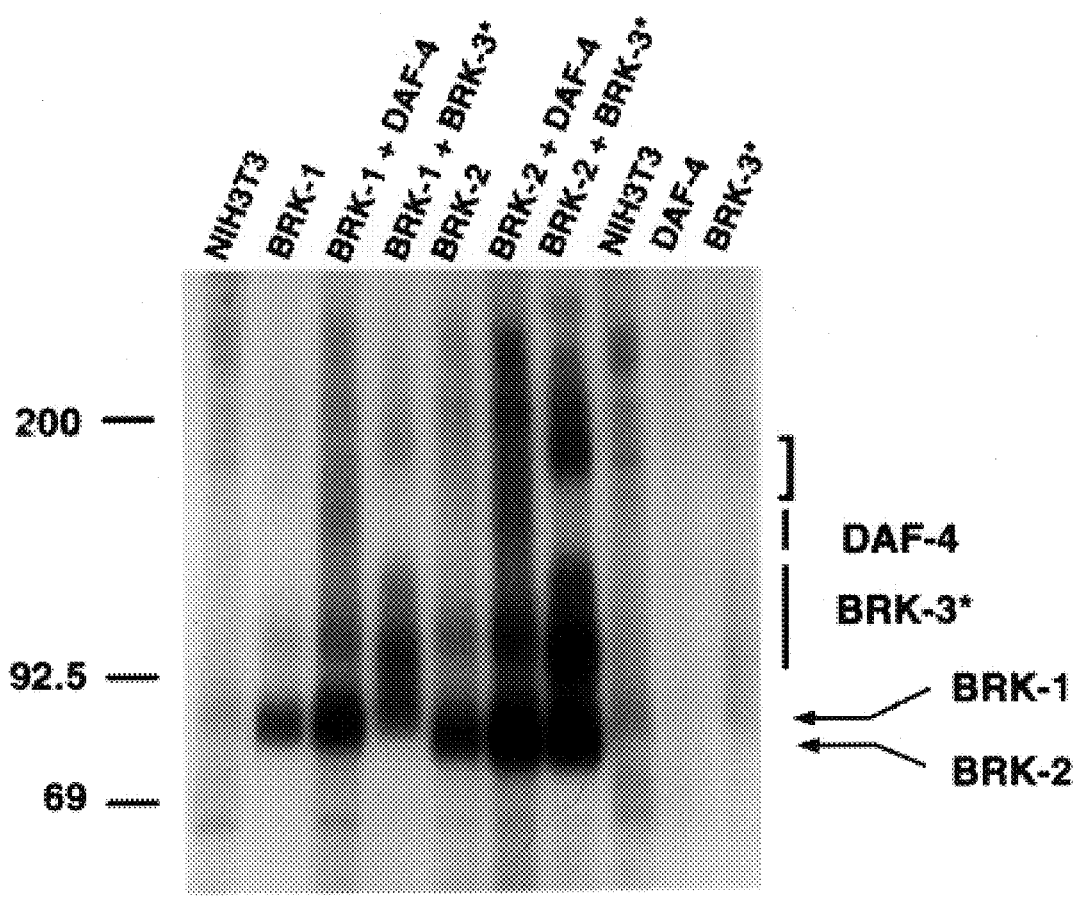
FIG. 8 shows an immunoprecipitation of t-BRK-3 and the C. elegans type II receptor DAF-4 expressed in COS-1 cells and crosslinked to [$^{125}$I]-BMP-4 in the presence or absence of the type I receptors BRK-1 or BRK-2. Molecular weight standards are shown on the left; areas shown at the right indicate labeled protein bands migrating at the predicted molecular weight of DAF-4, t-BRK-3, BRK-1, or BRK-2 crosslinked to [$^{125}$I]-BMP-4. Antiserum 1379 was used for COS-1 cells transfected with BRK-1 in the presence or absence of type II receptors, and antiserum 1380 for COS-1 cells transfected with BRK-2 in the presence or absence of type II receptors. For all others, antiserum is listed in parentheses. Left to right, NIH3T3 embryonic fibroblasts (1379), followed by COS-1 cells transfected with BRK-1 alone; BRK-1 plus DAF-4; BRK-1 plus t-BRK-3; BRK-2 alone; BRK-2 plus DAF-4; BRK-2 plus t-BRK-3. This is followed by NIH3T3 cells (1380), followed by COS-1 cells transfected with DAF-4 alone (1379), and t-BRK-3 alone (1380). In this figure, "BRK-3*" is t-BRK-3.

Results of this experiment are shown in FIG. 8, which shows the results of immunoprecipitations on COS-1 cells transfected with t-BRK-3 in the presence or absence of BRK-1 or BRK-2. Cells transfected with t-BRK-3 alone, crosslinked to [$^{125}$I]-BMP-4, and immunoprecipitated with antibody 1380 show no radiolabel in the immunoprecipitate, as expected since t-BRK-3 does not crossreact with this antibody. Cells transfected with BRK-1, crosslinked, and immunoprecipitated with antibody 1379 show a single labeled band at 78 kD, consistent with the predicted molecular weight of BRK-1 plus the cross-linked monomer of BMP-4. Immunoprecipitation of cells co-transfected with BRK-1 and t-BRK-3 yields the same band seen with BRK-1 alone, plus an additional labeled band at 94 kD, consistent with the predicted molecular weight of t-BRK-3 plus the crosslinked BMP-4 monomer. (A less intense band at 120 kD is also observed.) The fact that antibodies to BRK-1 precipitate not only BRK-1, but t-BRK-3 as well in these cells indicates complex formation between BRK-1 and t-BRK-3. Similarly, cells transfected with BRK-2, crosslinked to [$^{125}$I]-BMP-4, and subjected to immunoprecipitation with antibody 1380 show a labeled band at 75 kD, consistent with the predicted molecular weight of BRK-2 plus the crosslinked monomer of BMP-4. Immunoprecipitation of cells co-transfected with BRK-2 and t-BRK-3 yields the same band seen with BRK-2 alone, plus a strongly labeled band at 94 kD, consistent with the predicted molecular weight of t-BRK-3 plus the crosslinked monomer of BMP-4. As expected, this band co-migrates with the larger labeled band in cells co-transfected with BRK-1 and t-BRK-3. (A less intense band at 120 kD) is also observed.) Again, the fact that an antibody to BRK-2 precipitates not only BRK-2 but t-BRK-3 as well in these cells strongly indicates that BRK-2 and t-BRK-3 form a complex. Thus, t-BRK-3 forms a complex with two different type I BMP receptors, as expected for a type II BMP receptor.

A second immunoprecipitation experiment is carried out to test the ligand specificity of the t-BRK-3 receptor complex for BMP-2, BMP-4, and TGF-$\beta_1$. A derivative of BMP-2 designated "digit -removed" BMP-2 (DR-BMP-2) is also tested; DR-BMP-2 is prepared by mild trypsin digestion of BMP-2 to remove the amino terminus, and shows significantly reduced nonspecific binding to whole cells (B. B. Koenig, et al., *Molec. Cell. Biol.*, 14: 5961–5974 (1994)).

Figure 9:
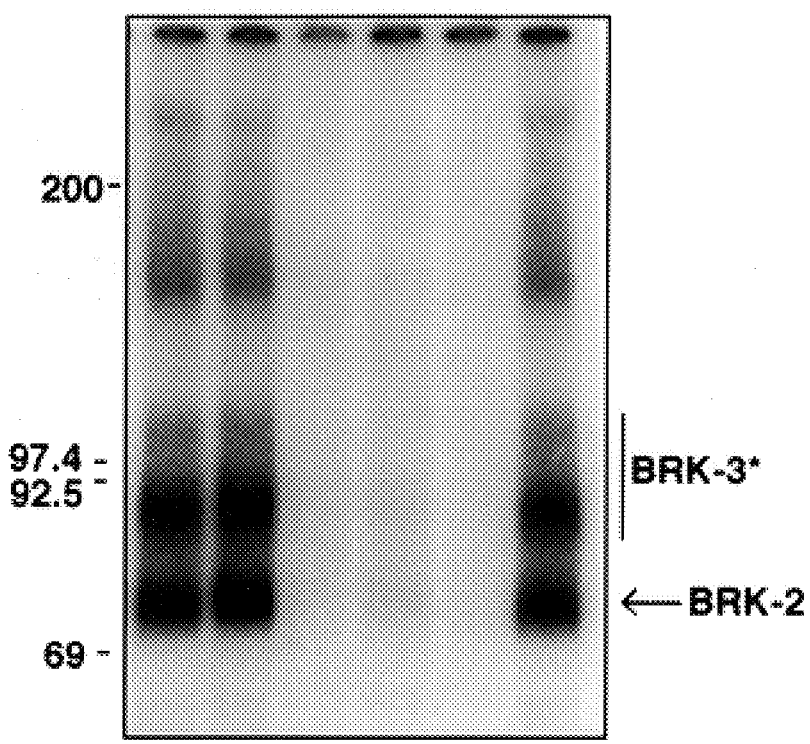
FIG. 9 shows an immunoprecipitation of COS-1 cells transfected with BRK-2 and t-BRK-3 and crosslinked to [$^{125}$I]-BMP-4 at a concentration of 210 pM, in the presence or absence of excess unlabeled competitors as indicated. Antiserum 1380 is used. Duplicate lanes at left show no unlabeled competitor added, followed by addition of (left to right) 10 nM BMP-4; 10 nM BMP-2; 10 nM DR-BRMP-2; and 50 nM TGF-$\beta_1$. In this figure, "BRK-3*" is t-BRK-3.

COS-1 cells are co-transfected with the cDNA for BRK-2 and t-BRK-3 as described in Example 5, crosslinked to [$^{125}$I]-BMP-4, and subjected to immunoprecipitation with antibody 1380 as described in this example, except that an excess of unlabeled ligand (10 nM BMP-4, 10 nM BMP-2, 10 nM DR-BMP-2, or 50 rM TGF-$\beta_1$) is added to the incubation at the same time as the [$^{125}$I]-BMP-4. The results are shown in FIG. 9. When no competing unlabeled ligands are present, two labeled bands are observed, at 75 kD and 94 kD, consistent with crosslinked BRK-2 and BRK-3 respectively, as seen in FIG. 8. In the presence of excess unlabeled BMP-4, BMP-2, or DR-BMP-2, however, these bands are completely abolished, demonstrating that these ligands compete effectively with [$^{125}$I]-BMP-4 to bind to the complex, and that all these ligands show specific binding to the BRK-2 and BRK-3 receptor complex. However, the presence of 50 nM TGF-$\beta_1$ has no effect on the labeled bands, indicating that TGF-$\beta_1$ does not bind to the same site as [$^{125}$I]-BMP-4. This shows that the BRK-2/t-BRK-3 complex binds specifically to BMP-2 and BMP-4 and does not bind TGF-$\beta$.

EXAMPLE 9

Isolation of Mouse BRK-3

In order to isolate the full-length mouse homologue of BRK-3, a cDNA library is constructed from NIH3T3 mouse embryonic fibroblasts (ATCC CRL 1658). Total RNA (1.26 mg) is isolated from the cells using a Total RNA Separator Kit (Clontech, Palo Alto, Calif.). Messenger RNA (81 µg) is isolated from this total RNA (1 mg) using the mRNA Separator Kit (Clontech, Palo Alto, Calif.). An aliquot of the mRNA (4 µg) is used to make cDNA library using the SUPER SCRIPT Plasmid System for cDNA Synthesis and Plasmid Cloning (Life Technologies, Gaithersburg, Md.) according to the manufacturer's instructions. The resulting library contained approximately 4.9×10$^5$ primary colonies, and is divided into 98 pools, each containing 5000 colonies.

The initial screen of the library is accomplished by Southern blotting. Plasmids are purified from each of the 98 pools, using QIAGEN columns (Qiagen, Chatsworth, Calif.). DNA from each pool (approximately 5 µg) is digested with Mlu I to release the cDNA insert, then run on a 1% agarose gel. The gel is denatured for 30 min in 0.6 M NaCl, 0.4 N NaOH, then neutralized 30 min in 1.5 M NaCl, 0.5 M Tris, pH 7.5. The DNA is then transferred overnight to a HYBOND Nylon membrane (Amersham, Arlington Heights, Ill.) using 10×SSC as the transfer buffer (1×SSC= 0.15 M NaCl, 0.015 M sodium citrate, pH 7.0).

Human t-BRK-3 is cut with EcoRV and Afl III to give a 1.5 kb fragment. The fragment is randomly labeled with alpha[$^{32}$P]-dCTP having a specific activity of 3000 Ci/mmol (NEN Research Products, Boston, Mass.), using a PRIME-IT II Random Primer Labeling Kit (Stratagene, La Jolla, Calif.; a kit for random primer labeling of DNA, including Klenow DNA polymerase, primers, and buffers). The labeled probe is allowed to hybridize to the Southern blot for 18 hr at 42° C. in hybridization buffer (Sigma, St. Louis, Mo.) consisting of 50% deionized formamide, 5×SSPE (1×SSPE=0.14 M NaCl, 8 mM sodium phosphate, 0.08 mM EDTA, pH 7.7), 1×Denhardt's solutions, and 100 µg/ml of denatured salmon testis DNA. The blot is then washed in 0.25×SSPE, 0.5% sodium dodecyl sulfate (SDS), two times at 42° C. for 15 min each, then two times at 65° C. for 20 min each. The blot is then exposed to Kodak X-OMAT AR autoradiography film for 18 hr at −80° C. Development of the film shows five positive pools, as judged by the presence of a labeled band of approximately 2.5 kb.

For secondary screening, plates are streaked with the *E. coli* stocks from the five positive pools (5000 colonies/ plate). A HYBOND nylon membrane is placed on top of the plate so that the bacterial colonies are transferred to the filter. The colonies are then allowed to recover at 37° C. for 2–3 hr. The filter is soaked in 10% SDS for 3 min, then transferred to 1.5 M NaCl, 0.5 M NaOH for 5 min, neutralized in 1.5 M NaCl, 1.5 M Tris, pH 7.5 for 5 min, and washed in 2×SSC. To remove proteins, the blots are then shaken with 50 µg/ml of proteinase K (Boehringer Mannheim, Indianapolis, Ind.) in 0.1 M Tris, pH 7.6, 10 mM EDTA, 0.15 M NaCl, 0.02% SDS at 55° C. for 1 hr. The human BRK-3 fragment (Eco RV-Afl III) is labeled and the blots hybridized, washed, and subjected to autoradiography exactly as described above for the primary screening.

Colonies which corresponded to labeled spots on the autoradiograph are streaked on plates for tertiary screening, which is performed exactly as described above for secondary screening. Four positive clones are isolated. One clone, pSPORT1/N89-5, is found to have the largest insert size, 2.9 kb.

The inserts from the four positive clones are sequenced using the TAQ DYE DEOXY Terminator Cycle Sequencing Kit and an Applied Biosystems Model 373A Automated DNA Sequencer. Comparison of the four sequences shows that three of the four are identical at the 3' end, and all four align with the coding region of human BRK-3 at the 5' end. The longest clone, pSPORT1/N89-5, aligns with the human BRK-3 sequence approximately 600 pairs from the beginning of the coding region.

To generate more sequence information, the insert from pSPORT1/N89-5 is digested with EcoRI and Sca I, and the resulting 1.4 kb fragment is subcloned into BLUESCRIPT II SK(−) at the Eco RI and Hinc II sites. pSPORT1/N89-5 is also digested with Eco RI and Eco RV and the resulting 2.1 kb insert subcloned into the same vector at the same sites. Finally, the plasmid is digested with Sca I and Not I, and subcloned into the same vector at the Hinc II and Not I sites. Sequencing of these three constructs yields the complete sequence of the insert from pSPORT1/N89-5.

The missing 600 base pairs at the 5' end of the coding region is cloned using the 5' RACE System for Rapid Amplification of cDNA Ends (Life Technologies, Gaithersburg, Md.). An antisense primer is designed corresponding to the known sequence of pSPORT1/N89-5, having the sequence 5'CTG TGT GAA GAT AAG CCA GTC 3' (the reverse complement of nucleotides 968–948 in SEQ ID NO:7). After first strand synthesis of cDNA from 1 μg of NIH3T3 mRNA, a poly C tail is added to the newly synthesized cDNA using terminal deoxynucleotidyl transferase, according to the manufacturer's instructions. The primer above is used to amplify the 5' end of the BRK-3 cDNA, together with the Anchor Primer supplied with the kit, having the sequence 5' (CUA)$_4$ GGC CAC GCG TCG ACT AGT ACG GGI IGG GII GGG IIG 3' (where I=inosine and U=uracil). PCR was performed using the GENE-AMP PCR Kit with AMPLITAQ DNA Polymerase. An initial melting period at 95° C. for 5 min was followed by 35 cycles of the following program: melting at 95° C. for 1 min, annealing at 55° C. for 1 min, and extension at 72° C. for 2 min. After the last cycle, the reaction was held at 72° C. for 5 min to complete extension. To reduce background from nonspecific primer binding, a second round of PCR is performed using the nested primer 5' CAA GAG CTT ACC CAA TCA CTT G 3', again derived from the known sequence of the insert from pSPORT1/N89-5 (the reverse complement of nucleotides 921–900 in SEQ ID NO: 7), together with same 5' anchor primer used in the first round of PCR.

The amplified products of the second PCR reaction in the size range of 600–1000 bp are digested with Ecl XI and Sal I and subcloned into BLUESCRIPT II SK(−) at the Ecl XI and Sal I sites. The inserts are then sequenced, yielding an additional 600 bp of sequence which align with the coding region of human t-BRK-3. Three separate clones, designated R6-8B2, R6-11-1, and R6-11-2, are sequenced with identical results.

In order to assemble a full length clone of mouse BRK-3, a Sal I site is first placed at the 5' end of clone R6-11-1 as follows. A primer is synthesized which contains a Sal I site followed by nucleotides 1–20 of the sequence of R6-11-1; the sequence of the primer is 5' CAC ACG CGT CGA CCA TGA CTT CCT CGC TGC ATC G 3'. This is used together with the M13 reverse primer, 5' AAC AGC TAT GAC CAT G 3', in order to amplify a DNA fragment using plasmid DNA from clone R6-11-1 as the template. PCR was performed using the GENE-AMP PCR Kit with AMPLITAQ DNA Polymerase. An initial melting period at 95° C. for 5 min was followed by 35 cycles of the following program: melting at 95° C. for 1 min, annealing at 55° C. for 1 min, and extension at 72° C. for 2 min. After the last cycle, the reaction was held at 72° C. for 5 min to complete extension. The fragment amplified from R6-11-1, together with the insert from pSPORT1/N89-5 (230 ng), is then subcloned in to BLUESCRIPT II SK(−) as follows. The amplified fragment from R6-11-1 is digested with Sal I and Ed XI. The insert from pSPORT1/N89-5 is digested with Ecl XI and Pst I. The vector BLUESCRIPT II SK(−) is digested with Sal I and Pst I. The three fragments are combined in a three-way ligation using T4 DNA ligase (3 hr, 25° C.) and used to transform electrocompetent E. coli, strain DH5-a, using a BIO-RAD Gene PULSER (BIO-RAD, Hercules, Calif.) according to the manufacturer's instructions. A positive colony is selected and is designated pBLUESCRIPT-mBRK3. Sequencing of the 5' portion of the insert that was amplified by PCR shows a sequence identical to that of clone R6-11-1, indicating that no mutations are introduced during the amplification.

For mammalian expression, m-BRK-3 is subcloned into the mammalian expression vector pJT6. This vector is a derivative of pJT3, described in example 4 above, in which the Not I site at the 5' end of the multiple cloning site has been deleted, and a spacer inserted between the Pst I and BamHI restriction sites in the multiple cloning site. To accomplish the subcloning, m-BRK-3 is excised from pBLUESCRIPT-mBRK3 using Not I and Sal I, then subcloned into pJT6 at the Not I and Sal I sites to generate pJT6-mBRK3.

However, resequencing of the 3' end of pJT6-mBRK3 and the original cDNA in pSPORT1/N89-5 results in an altered reading frame at the 3' end, and shows that the stop codon is actually located 3' to the Pst I site. Thus, pJT6-mBRK3 does not contain a stop codon. Accordingly, two new constructs are prepared as follows.

Figure 10:
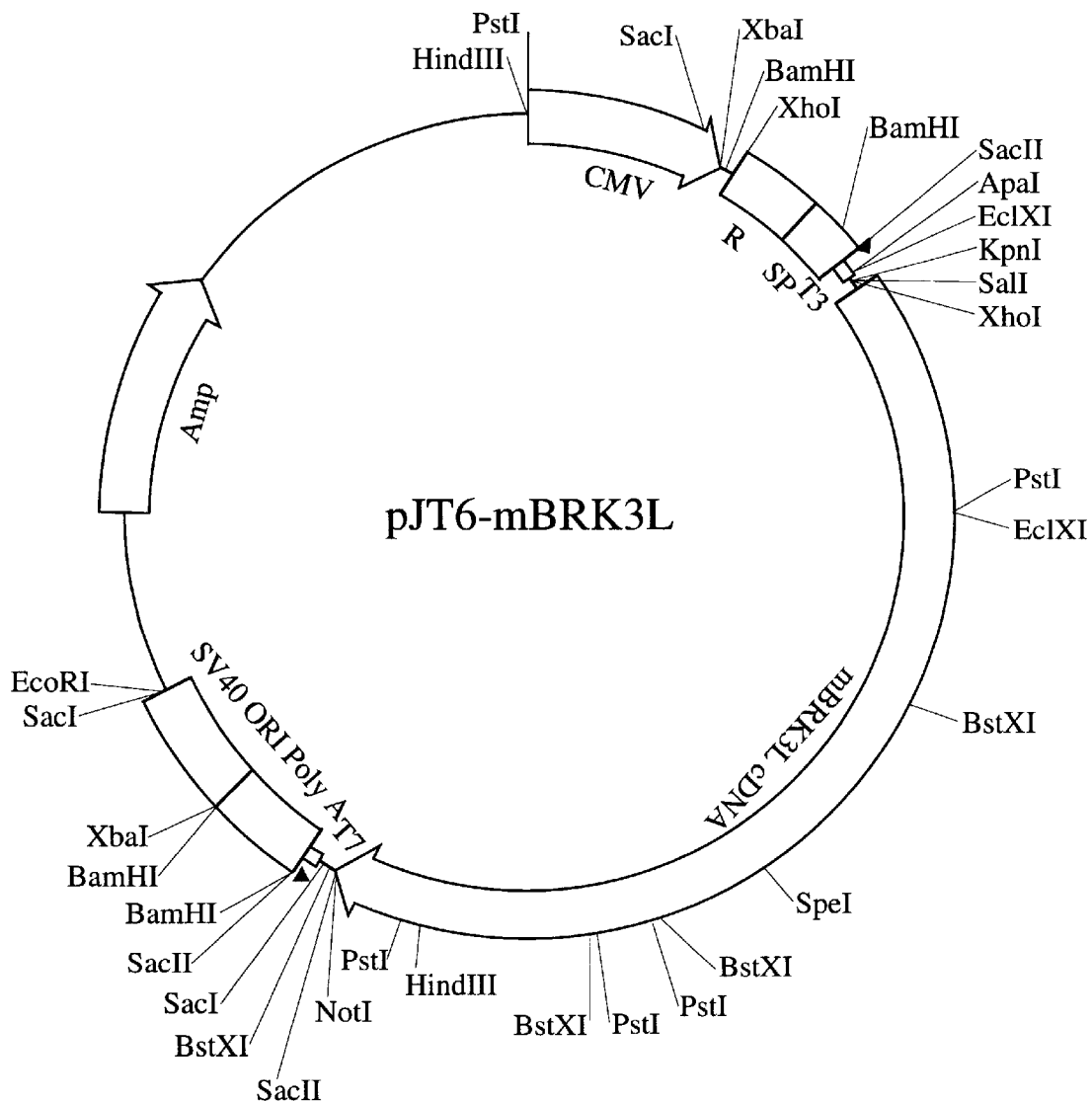
FIG. 10 shows the construct pJT6-mBRK-3L, used for transient mammalian expression of mouse BRK-3. Abbreviations used are the same as those for FIG. 2.

First, pJT6-mBRK3 is digested with SpeI (site at position 2306 in SEQ ID NO: 7) and Not I (in the multiple cloning site of pJT6), removing the 3' end of the insert. The longest clone isolated during the screening of the NIH-3T3 library, pSPORT1/N89-5, is also digested with Spe I and Not I. The 1.2 kb fragment liberated from pSPORT1/N89-5 is subcloned into the Spe I/Not I digested pJT6-mBRK3, regenerating both sites. This construct is designated pJT6-mBRK-3L, and contains the entire 3' end of the pSPORT1/N89-5 clone. A map of the construct is shown in FIG. 10.

Figure 11:
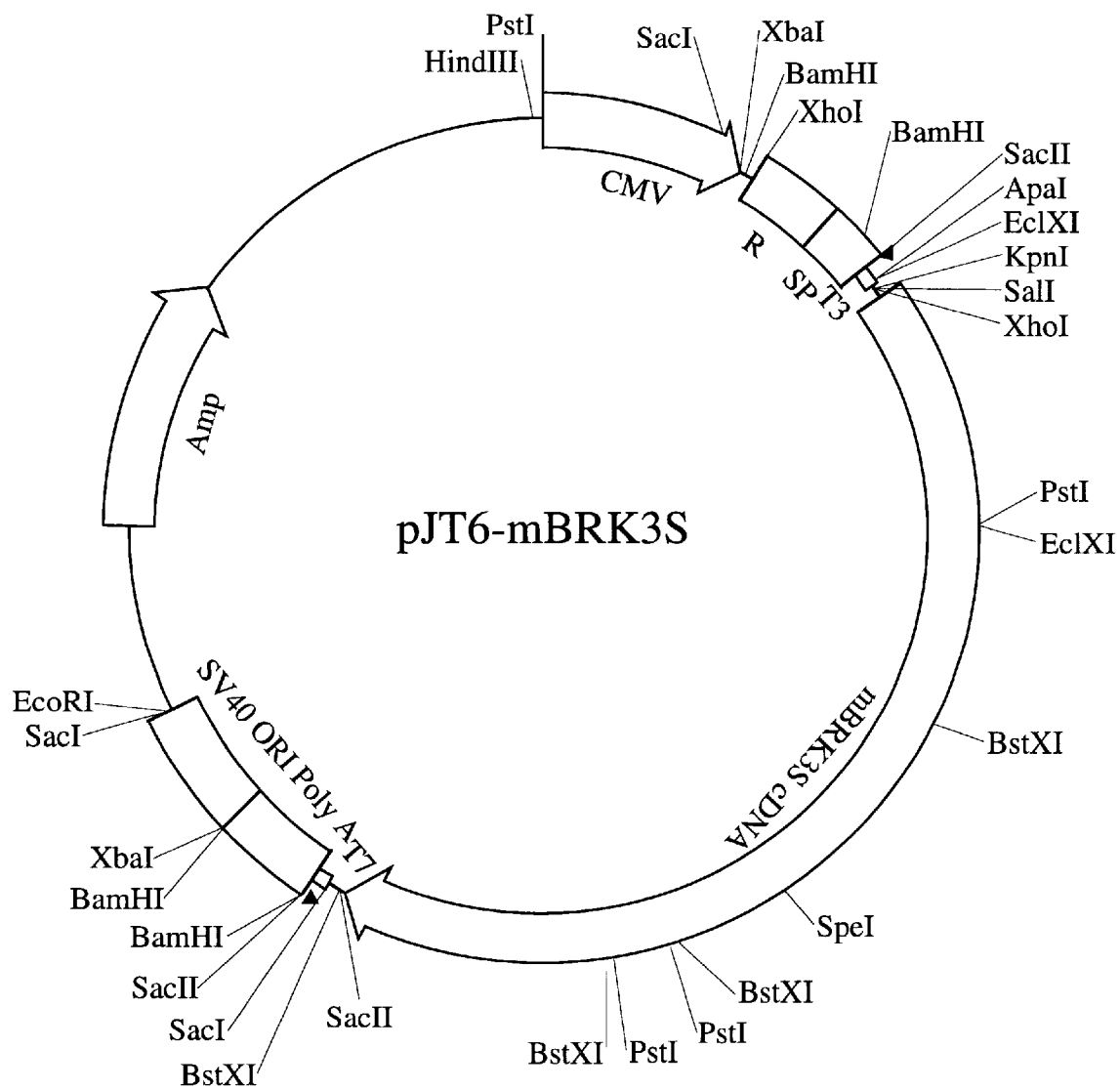
FIG. 11 shows the construct pJT6-mBRK-3S, used for transient mammalian expression of mouse BRK-3. In this construct, most of the untranslated 3' region has been removed. Abbreviations used are the same as those for FIG. 2.

The 3' end of the clone contains 403 nucleotides in the untranslated region 3' to the stop codon. This region is very A-T rich, which might possibly lead to decreased expression levels. To remove this region, a second construct is prepared. The pSPORT1/N89-5 plasmid is digested with Hind III (site at nucleotide 3168 in SEQ ID NO: 7, 21 bases 3' to the stop codon). The linearized plasmid is treated with Klenow fragment of DNA polymerase (Boehringer Mannheim, Indianapolis, Ind.) to fill in overhangs, then cut with Spe I to liberate an 863 bp fragment at the 3' end of the insert. At the same time, pJT6-mBRK3 is digested with Not I. The linearized plasmid is treated with Klenow fragment, then cut with Spe I, releasing the 3' end of the insert. The Not I/Spe I digested pJT6-mBRK3 is then ligated to the fragment liberated from pSPORT1/N89-5 by Hind III/Spe I. This regenerates the Spe I site; the Hind III and Not I sites are destroyed. The resulting construct is designated pJT6-mBRK3S, and is shown in FIG. 11.

The construct pJT6-mBRK-3S is also constructed directly from the partial cDNA clone of m-BRK-3, pSPORT1/N89-5, and the construct containing the 5' end of the cDNA, clone R6-11-1. This is accomplished by digestion of clone R6-11-1 with Sal I and Ecl XI, digestion of pSPORT1/N89-5 with Ecl X and Hind III, and digestion of BLUESCRIPT II SK (−) with Sal I and Hind III. These fragments are then subjected to a three-way ligation to generate the full length m-BRK-3 cDNA in the BLUESCRIPT II vector. The full length cDNA is then excised from this construct using Sal I and Not I, then subcloned into the Sal I and Not I sites of the pJT6 vector. The resulting plasmid has exactly the same cDNA for BRK-3 as does pJT6-mBRK3S described in the above example. However, it carries additional vector sequence at the 3' end of the cDNA, comprising the region between the Hind III and Not I sites in the multiple cloning site of BLUESCRIPT II SK(−).

EXAMPLE 10

Sequence Analysis of Mouse BRK-3

The DNA sequence of the full length mouse BRK-3 insert from pJT6-mBRK3L is shown in SEQ ID NO: 7, and the deduced protein sequence is shown in SEQ ID NO: 8. The deduced amino acid sequence of mouse BRK-3 is searched against all translated protein sequences in GenBank release 84.0, dated Aug. 15, 1994, using a standard Needleman-Wunsch algorithm (S. B. Needleman and C. D. Wunsch, *J. Mol. Biol.*, 48: 443–453 (1970)). It is found to be a unique sequence. It encodes a protein of 1038 amino acids. Comparing mouse BRK-3 with the truncated human receptor over the region encoded by t-BRK-3 (amino acids 1–582 in SEQ ID NO:4; amino acids 1–582 in SEQ ID NO: 8), the two receptors are 98% identical in sequence. Like t-BRK-3, m-BRK-3 contains a predicted transmembrane region encompassing amino acids 151–172. As with t-BRK-3, the intracellular domain contains all of the consensus sequences that characterize a protein kinase domain with predicted specificity for serine/threonine residues (S. K. Hanks, A. M. Quinn, and T. Hunter, *Science*, 241: 42–52 (1988)). The kinase domain is followed by an extremely long carboxy terminus (534 amino acids). Indeed, due to the presence of this carboxy terminus, the intracellular domain in BRK-3 (866 amino acids) is much larger than that of any other receptor in the TGF-β receptor family. It is nearly twice as long as the intracellular domain of DAF-4 (490 amino acids), which has the longest intracellular domain known in the TGF-β family until the present invention.

EXAMPLE 11

Demonstration of [$^{125}$I]-BMP-4 binding to m-BRK-3

In order to demonstrate that [$^{125}$I]-BMP-4 binds specifically to m-BRK-3, COS-1 cells are transfected as described in Example 5 using the constructs pJT6-mBRK-3S and pJT6-mBRK-3L. In addition, the cells are also co-transfected with cDNA for the type I receptor BRK-2, using the construct pJT3-BRK-2, to determine whether the presence of a type I BMP receptor affects binding of [$^{125}$I]-BMP-4. Whole cell binding with [$^{125}$I]-BMP-4 is carried out as described in Example 7.

Figure 12:
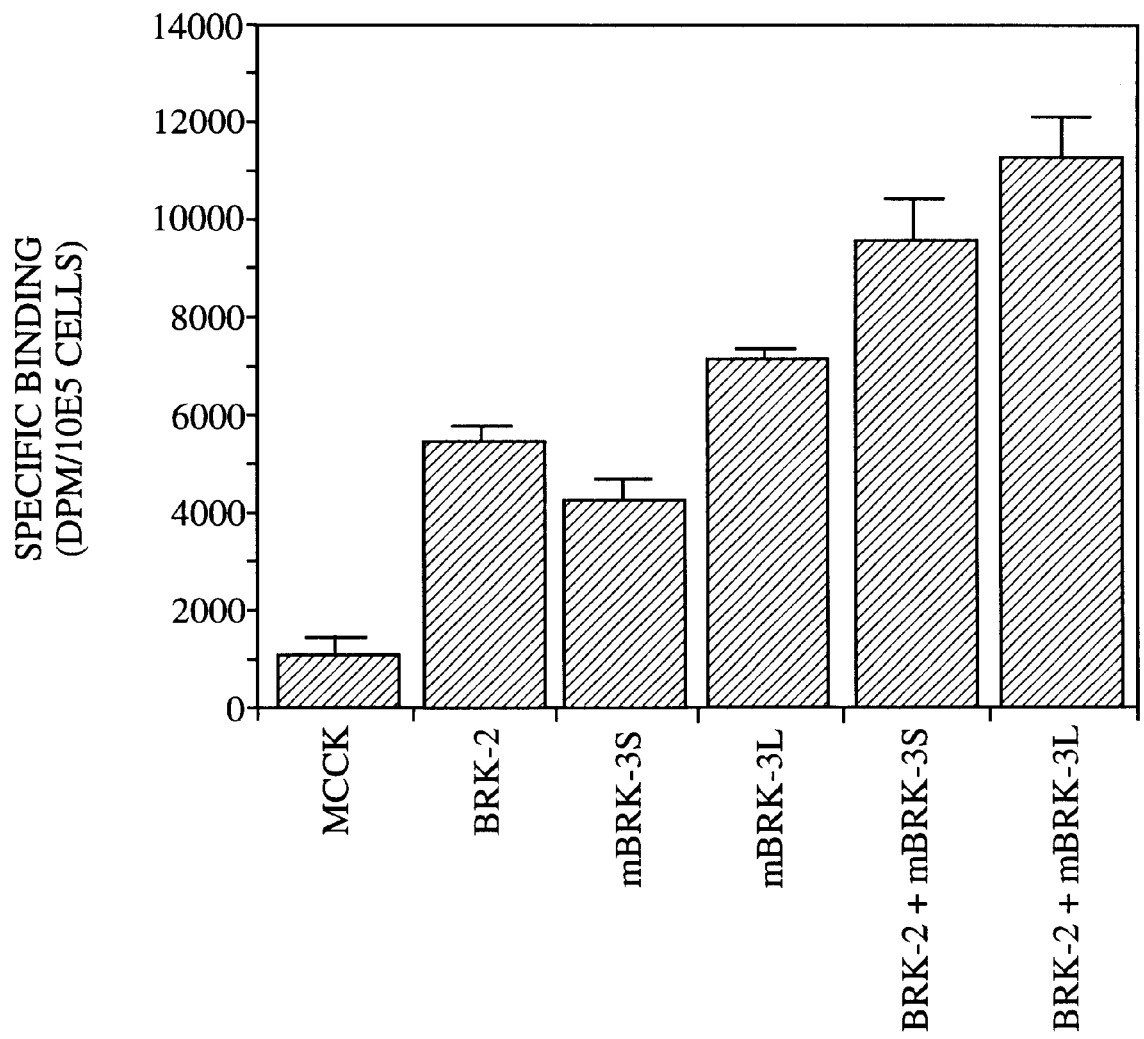
FIG. 12 shows whole cell binding of [$^{125}$I]-BMP-4 to mouse BRK-3 expressed in COS-1 cells, in the presence or absence of the type I receptor BRK-2. Bars represent specific binding of [$^{125}$I]-BMP-4, normalized to cell number. Constructs used for mouse BRK-3 are pJT6-mBRK-3L and pJT6-mBRK-3S; for BRK-2, the construct is pJT3-BRK-2. Both constructs contain the complete coding region of mouse BRK-3. In pJT6-mBRK-3S, an A-T rich region in the 3' untranslated region has been deleted. Left to right, COS-1 cells transfected with the vector pJT-6 alone (designated "mock"); pJT3-BRK-2 alone; the construct pJT6-mBRK-3S alone; pJT6-mBRK-3L alone; pJT3-BRK-2 plus pJT6-BRK-3S; and pJT3-BRK-2 plus pJT6-BRK-3L.

The results are shown in FIG. 12, which shows specific binding of [$^{125}$I]-BMP-4 normalized to cell number. When cells are transfected with mouse BRK-3 alone, using either of the two constructs tested, specific binding of [$^{125}$I]-BMP-4 is increased to 4–7 times the level seen with mock transfected cells. Transfection of BRK-2 alone shows increased binding at a similar level to that seen with mouse BRK-3 alone. When cells are co-transfected with BRK-2 as well as mouse BRK-3, the binding is further increased to 9–11 times that of mock-transfected cells, consistent with the results obtained with BRK-2 in combination with t-BRK-3 (FIG. 6 in. Example 7 above).

Figure 13:
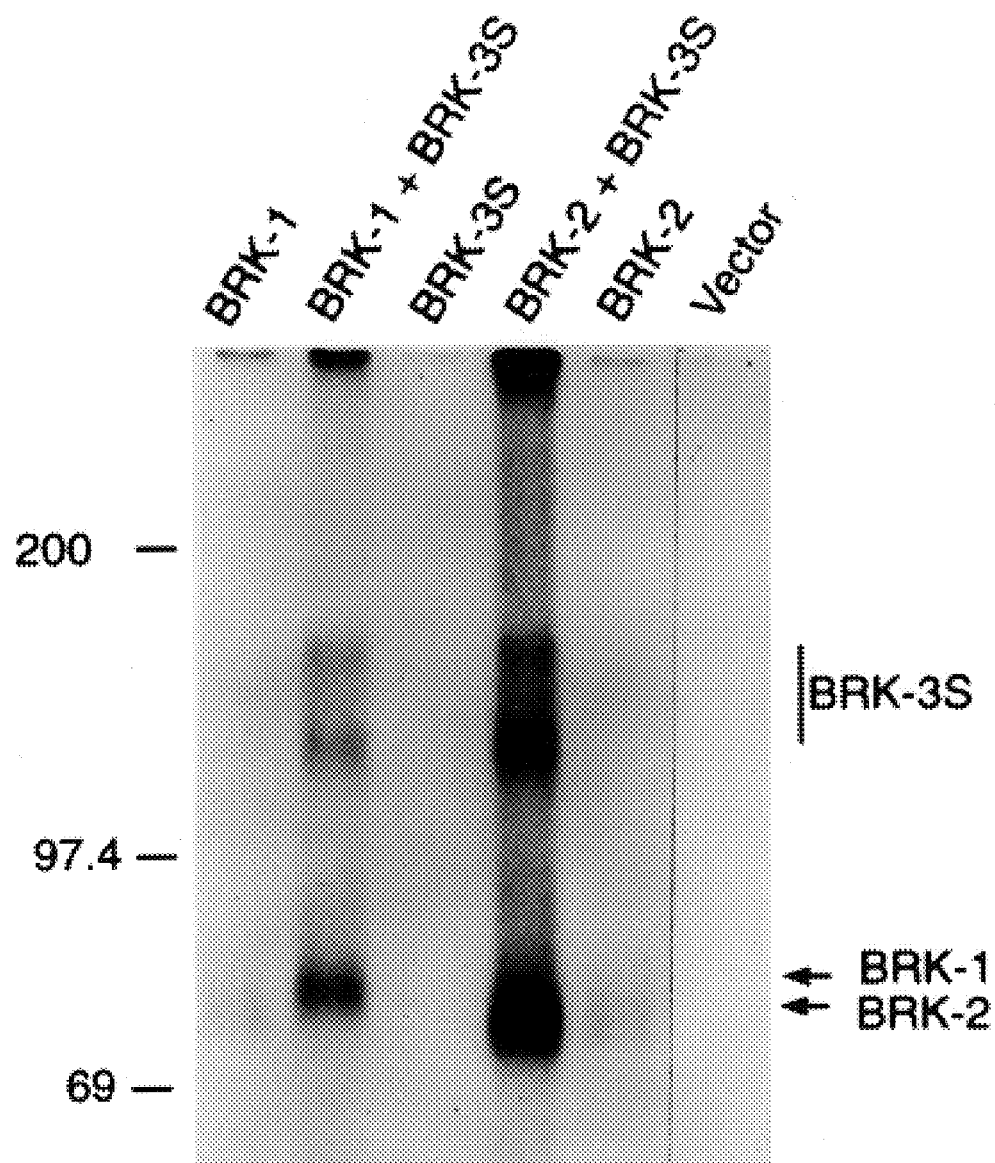
FIG. 13 shows crosslinking of [$^{125}$I]-BMP-4 to m-BRK-3 in the presence and absence of type I BMP receptors. COS-1 cells are transfected with the cDNA for BRK-3 using the construct pJT6-mBRK-3S, and/or with cDNAs for BRK-1 (using pJT4-J159F) or BRK-2 (using pJT3-BRK-2). The cells are then allowed to bind [$^{125}$I]-BMP-4, crosslinked with disuccinimidyl suberate, and subjected to SDS gel electrophoresis. Position of molecular weight standards is indicated on the left. Left to right: COS-1 cells transfected with BRK-1 alone; BRK-1 plus m-BRK-3; m-BRK-3 alone; BRK-2 plus m-BRK-3; BRK-2 alone; and vector alone. Bands identified with BRK-1, BRK-2, and BRK-3 are indicated on the right.

As an additional demonstration that m-BRK-3 binds to [$^{125}$I]-BMP-4, a crosslinking experiment is carried out. COS-1 cells are transfected with the cDNA for m-BRK-3, using the construct pJT6-mBRK-3S, and/or with cDNAs for BRK-1 (using pJT4-J159F) or BRK-2 (using pJT3-BRK-2) as described in Example 5. The transfected cells are incubated with [$^{125}$I]-BMP-4 and crosslinked as described in Example 7, except that disuccinimidyl suberate (DSS) is used as the crosslinking agent rather than disuccinimidyl glutarate. The results of such an experiment are shown in FIG. 13. Cells transfected with m-BRK-3 alone show no crosslinked band, consistent with the results obtained with t-BRK-3 (FIG. 7). Cells transfected with the cDNA for BRK-1 alone show a single species migrating at an apparent molecular weight of 81 kD, consistent with the predicted molecular weight of BRK-1 plus the crosslinked BMP-4 monomer. Cells transfected with the cDNAs for BRK-1 and m-BRK-3 show three labeled bands, one of which is consistent with the band seen with BRK-1 alone (81 kD). The other bands migrate with an apparent molecular weight of 159 kD and 128 kD. The larger of these is consistent with the predicted molecular weight of m-BRK-3 plus the crosslinked BMP-4 monomer. Note that the intensity of the crosslinked band identified with BRK-1 is considerably increased, compared to that seen with BRK-1 alone.

Similarly, transfection of cells with the cDNA for BRK-2 alone yields a crosslinked band migrating at an apparent molecular weight of 78 kD, consistent with the predicted molecular weight of BRK-2 plus the crosslinked BMP-4 monomer. In cells transfected with the cDNAs for BRK-2 and mBRK3, the 78 kD species identified with BRK-2 is observed, as well as crosslinked bands at 159 kD and 128 kD, comigrating with the higher molecular weight bands seen in cells transfected with the cDNAs for BRK-1 and m-BRK-3. As with BRK-1, the intensity of crosslinking to the band identified with BRK-2 is considerably increased compared to that seen with BRK-2 alone. Finally, no labeled bands are observed in cells transfected with vector alone.

Figure 14:
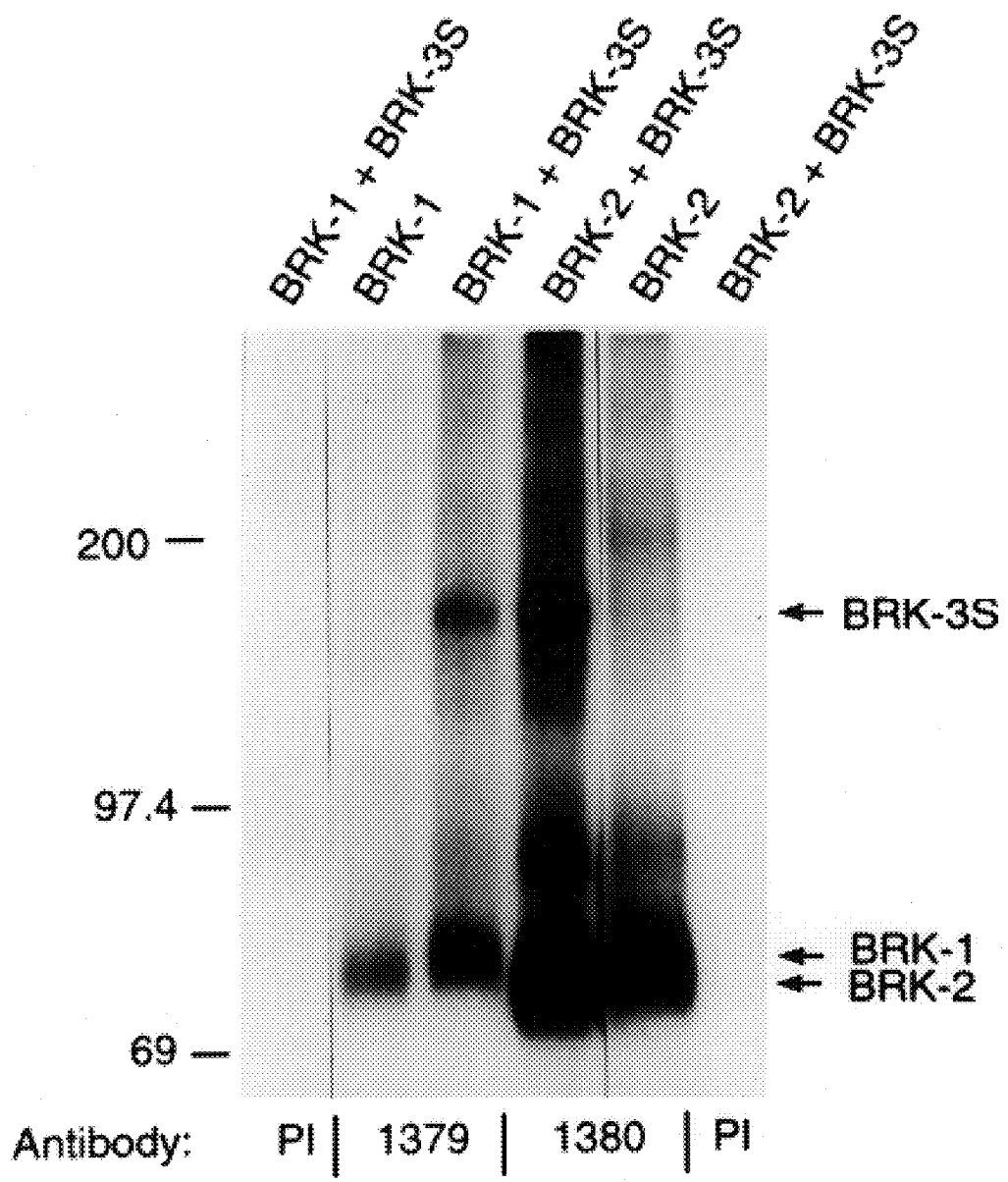
FIG. 14 shows immunoprecipitation of m-BRK-3 in the presence and absence of type I BMP receptors. COS-1 cells are transfected with the cDNA for m-BRK-3 using the construct pJT6-mBRK-3S, and/or with cDNAs for BRK-1 (using pJT4-J159F) or BRK-2 (using pJT3-BRK-2). The cells are then allowed to bind [$^{125}$I]-BMP-4, crosslinked with disuccinimidyl suberate, immunoprecipitated with antibodies to BRK-1 or BRK-2, and subjected to SDS gel electrophoresis. Antisera used are indicated below the lanes: PI, preimmune; 1379, for cells transfected with cDNA for BRK-1; 1380, for cells transfected with cDNA for BRK-2. Position of molecular weight standards is indicated on the left. Left to right, COS-1 cells transfected with BRK-1 plus m-BRK-3 (preimmune serum); BRK-1 alone; BRK-1 plus m-BRK-3; BRK-2 plus m-BRK-3; BRK-2 alone; and BRK-2 plus m-BRK-3 (preimmune serum).

An immunoprecipitation experiment is carried out to demonstrate the ability of m-BRK-3 to form a complex with type I BMP receptors. COS-1 cells are transfected with the cDNA for m-BRK-3, using the construct pJT6-mBRK-3 S, and/or with cDNAs for BRK-1 (using pJT4-J159F) or BRK-2 (using pJT3-BRK-2) as described in Example 5. The transfected cells are incubated with [$^{125}$I]-BMP-4, crosslinked, and subjected to immunoprecipitation with antibodies to the appropriate type I receptor or preimmune serum as described in example 8, except that DSS is used as the crosslinking agent rather than disuccinimidyl glutarate. The results of this experiment are shown in FIG. 14. In cells transfected with cDNA for BRK-1 alone, a single band is precipitated by antibodies to BRK-1, migrating at an apparent molecular weight of 81 kD. In cells transfected with cDNAs for BRK-1 and m-BRK-3, antibodies to BRK-1 precipitate the 81 kD band, which is now increased in intensity. In addition, however, a band migrating at an apparent molecular weight of 159 kD is observed, consistent with the predicted molecular weight of m-BRK-3 plus crosslinked BMP-4 monomer. Similarly, in cells transfected with cDNA for BRK-2 alone, antibodies to BRK-2 precipitate a labeled species migrating at an apparent molecular weight of 78 kD. In cells transfected with cDNAs for BRK-2 and m-BRK-3 and precipitated with antibodies to BRK-2, the 78 kD band identified with BRK-2 is again observed, at increased intensity. In addition, a labeled species is seen at 159 kD, consistent with m-BRK-3 and comigrating with the higher molecular weight band seen in cells transfected with cDNAs for BRK-1 and m-BRK-3. In cells transfected with cDNAs for BRK-2 and m-BRK-3, an additional labeled band is observed at 94 kD. As a control, cells are transfected with the cDNAs for BRK-1 and m-BRK-3, or BRK-2 and m-BRK-3, then subjected to immunoprecipitation with pre-immune sera (lanes far left and far right); no labeled bands are observed.

This experiment shows that when m-BRK-3 is co-expressed with the type I BMP receptors BRK-1 or BRK-2, antibodies which precipitate the type I receptor also precipitate m-BRK-3. Thus, m-BRK-3 can form a complex with either of these mammalian type I BMP receptors, as expected for a mammalian type II BMP receptor. This is consistent with results obtained with t-BRK-3 described in Example 8 above.

EXAMPLE 12

Isolation of Full Length Human BRK-3 cDNA

Since clone HSK723, described in Example 2, does not contain an in-frame stop codon, it is desired to obtain additional sequence 3' to the end of this cDNA. Accordingly, the human foreskin fibroblast library prepared in Example 1 is rescreened with the HSK7-2 PCR fragment, using labeling and screening conditions exactly as described in Example 2. This results in isolation of a longer clone, designated pHSK1030, which contains additional human BRK-3 sequence (total of 3355 base pairs) subcloned in BLUESCRIPT SK(–). Sequencing of the insert from pHSK1030 discloses a coding region of 982 amino acids, but the insert still does not contain an in-frame stop codon.

The remainder of the coding region is cloned by PCR as follows. Two forward primers are derived from the plus strand of clone pHSK1030. The sequences of these primers are as follows: primer RPK3-1, 5' CCTGTCACATAATAGGCGTGTGCC-3' (identical to nucleotides 1998–2021 in SEQ ID NO:1); primer RPK3-2, 5' CGCGGATCCATCATACTGACAGCATCG 3' (which incorporates a BamHI site followed by nucleotides 2078–2095 in SEQ ID NO:1). Two additional primers are derived from the minus strand of λgt10. These primers are: G10F1, 5' GCTGGGTAGTCCCCACCTTT 3' and G10F2, 5' GAGCAAGTTCAGCCTGGT 3'.

The human fibroblast cDNA library prepared in Example 1 is used as the template for PCR. The library (0.3 μg) is incubated with the RPK3–1 and G10F1 primers (1 μM each), Tth polymerase (1.2 units), all four deoxynucleotides (200 μM each), buffer for the Tth polymerase, and water in a total of 50 μl. Conditions for the PCR cycle are as follows: initial melting at 94° C. for 2 min, followed by 20 cycles of melting, 94° C. for 1.5 min; annealing, 52° C. for 2 min; and extension, 72° C. for 3 min. After cycle 20, the sample is held at 72° C. for an additional 8 min to insure complete extension.

To increase specificity and reduce background, a second round of nested PCR is carried out. The incubation mixture is the same as described in this example for the first round, except that (1) an aliquot of the first PCR reaction (0.5 μl) is used as the template; and (2) RPK3-2 and G10F2 primers are used, instead of RPK3-1 and G10F1. Conditions for the PCR run are identical to those described in this example for the first round of PCR.

The second round of PCR results in the amplification of a 1.6 kb fragment, which is isolated from an agarose gel by QIAEX. This fragment is digested with EcoRI and BamHI, and subcloned into BLUESCRIPT SK(–) at the EcoRI and Bam HI sites. The resulting construct, pHSK723-3U, is sequenced and found to encode the remaining coding region of BRK-3 with an in-frame stop codon.

Figure 15:
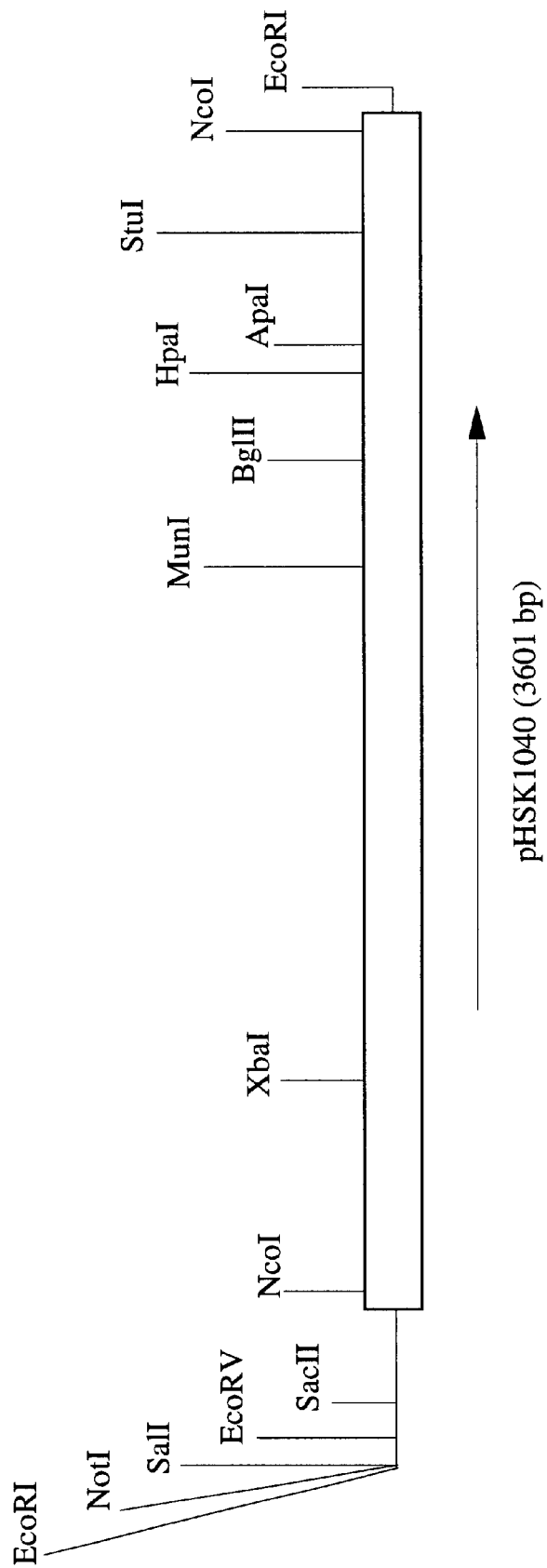
FIG. 15 shows a map of the insert of pHSK1040. This construct contains the complete coding region of human BRK-3 in BLUESCRIPT II SK (−).

In order to assemble the full length human BRK-3, the inserts from pHSK1030 and pHSK723-3U are joined at a unique Stu I site (located at nucleotide 3219 in SEQ ID NO:1) in the vector BLUESCRIPT II SK(–). This yields the complete construct pHSK1040, which contains the complete coding sequence of human BRK-3. The pHSK1040 is shown in FIG. 15. The DNA sequence of human BRK-3 is shown in SEQ ID NO: 1, and the deduced amino acid sequence for human BRK-3 is shown in SEQ ID NO: 2.

The amino acid sequence of human BRK-3 (SEQ ID NO:2) is compared to the amino acid sequence for m-BRK-3 (SEQ ID NO:8) and found to be 96.7% identical.

EXAMPLE 13

Use of the BRK-3 in a Ligand Binding Assay for the Identification of BMP Receptor Agonists and Antagonists Identification of ligands that interact with BRK-3 can be achieved through the use of assays that are designed to measure the interaction of ligands with BRK-3. An example of a receptor binding assay that is adapted to handle large numbers of samples is carried out as follows.

COS-1 cells are transfected with the cDNA for m-BRK-3 using the construct pJT6-mBRK-3L as described in example 11 above, except that cells are grown in a 12 well culture dish. At 48–68 hr after transfection, the cells are washed once with 1.0 ml binding buffer (50 mM HEPES, pH 7.4, 128 mM NaCl, 5 mM KCL, 5 mM $MgSO_4$, 1.2 mM $CaCl_2$, 2 mg/ml BSA), then equilibrated in the same buffer at 4° C. for 60 min. with gentle shaking. After equilibration, the buffer is aspirated, and to each well is added 500 μl of 4° C. binding buffer containing [$^{125}$I]BMP-4 tracer (100–400 pM) in the presence or absence of varying concentrations of unlabeled test compounds (i.e., putative ligands), for a period of 4 hours at 4° C. with gentle shaking. For determination of nonspecific binding and complete displacement from the BMP receptor complex, BMP-2 is added at a final concentration of 10 nM. To prevent degradation of ligand, a protease inhibitor cocktail is also added, to give a final concentration of 10 μg/ml leupeptin, 10 μg/ml antipain, 50 μg/ml aprotinin, 100 μg/ml benzamidine, 100 μg/ml soybean trypsin inhibitor, 10 μg/ml bestatin, 10 μg/ml pepstatin, and 300 μM phenylmethylsulfonyl fluoride (PMSF). At the end of the incubation period, the buffer is aspirated, and the cells are rinsed 4 times with 1 ml washing buffer (50 mM HEPES, pH 7.4, 128 mM NaCl, 5 mM KCl, 5 mM $MgSO_4$, 1.2 mM $CaCl_2$, 0.5 mg/ml BSA). After the final wash is aspirated, 200 μl of solubilization buffer (10 mM Tris Cl, pH 7.4, 1 mM EDTA, 1% (v/v) Triton X-100) is added to each well and incubated at room temperature for 15–30 min. The solubilized cells are then transferred to fresh tubes and counted in a Packard Model 5005 COBRA Gamma Counter (Packard Instruments, Meriden, Conn.).

Test compounds which interact with the m-BRK-3 receptor are observed to compete with binding to the receptor with the [$^{125}$I]BMP-4 tracer in the cells expressing m-BRK-3, such that less [$^{125}$I]BMP-4 tracer is bound in the presence of the test compound in comparison to the binding observed when the tracer is incubated in the absence of the novel compound. A decrease in binding of the [$^{125}$I]BMP-4 tracer by ≧30% at the highest concentration of the test compound that is studied demonstrates that the test compound binds to m-BRK-3.

Similar results are obtained when other, related BRK-3 protein receptor kinases of the present invention are used according to the method of this example.

EXAMPLE 14

Use of m-BRK-3 and BRK-2 in a Ligand Binding Assay for the Identification of BMP Receptor Agonists and Antagonists Identification of ligands that interact with BRK-3 complexed to a type I BMP receptor can be achieved through the use of assays that are designed to measure the interaction of the ligands with this BMP receptor complex. A receptor binding assay that uses the m-BRK-3/BRK-2 complex and is adapted to handle large numbers of samples is carried out as follows.

COS-1 cells are transfected with the cDNAs for m-BRK-3, using the construct pJT6-mBRK-3L, and BRK-2, using the construct pJT3-BRK-2, as described in example 11 above, except that the cells are grown in a 12 well culture dish. The DNA mixture used to transfect the cells contains 2 µg/ml of pJT3-BRK-2 and 4 µg/ml of pJT6-mBRK-3L. At 48–68 hours after transfection, the cells are washed once with 1 ml binding buffer (50 mM HEPES, pH 7.4, 128 mM NaCl, 5 mM KCL, 5 mM $MgSO_4$, 1.2 mM $CaCl_2$, 2 mg/ml BSA), then equilibrated in the same buffer at 4° C. for 60 min with gentle shaking. After equilibration, the buffer is aspirated, and to each well is added 500 µl of 4° C. binding buffer containing [$^{125}$I]BMP-4 tracer (100–400 pM) in the presence or absence of varying concentrations of test compounds (i.e., putative ligands), for a period of 4 hours at 4° C. with gentle shaking. For determination of nonspecific binding and complete displacement from the BMP receptor complex, BMP-2 is added at a final concentration of 10 nM. To prevent degradation of ligand, a protease inhibitor cocktail is also added, to give a final concentration of 10 µg/ml leupeptin, 10 µg/ml antipain, 50 µg/ml aprotinin, 100 µg/ml benzamidine, 100 µg/ml soybean trypsin inhibitor, 10 µg/ml bestatin, 10 µg/ml pepstatin, and 300 µM phenylmethylsulfonyl fluoride (PMSF). At the end of the incubation period, the buffer is aspirated, and the cells are rinsed 4 times with 1 ml washing buffer (50 mM HEPES, pH 7.4, 128 mM NaCl, 5 mM KCl, 5 mM $MgSO_4$, 1.2 mM $CaCl_2$, 0.5 mg/ml BSA). After the final wash is aspirated, 200 µl of solubilization buffer (10 mM Tris Cl, pH 7.4, 1 mM EDTA, 1% (v/v) Triton X-100) is added to each well and incubated at room temperature for 15–30 min. The solubilized cells are then transferred to fresh tubes and counted in a Packard Model 5005 COBRA Gamma Counter (Packard Instruments, Meriden, Conn.).

Test compounds which interact with the m-BRK-3/BRK-2 receptor complex are observed to compete for binding to the receptor complex with the [$^{125}$I]BMP-4 tracer, such that less [$^{125}$I]BMP-4 tracer is bound in the presence of the test compound in comparison to the binding observed when the tracer is incubated in the absence of the novel compound. A decrease in binding of the [$^{125}$I]BMP-4 tracer by $\geq 30\%$ at the highest concentration of the test compound that is studied demonstrates that the test compound binds to the m-BRK-3/BRK-2 receptor complex.

Similar results are obtained when the other BRK-3 protein receptor kinases of the present invention, or homologues thereof, are used in combination with BRK-2 or other BMP type I receptors.

Deposit of BRK-3, t-BRK-3 and m-BRK-3

*E. coli* transformed with pJT4-J159F (SEQ ID NO:11 subcloned into expression vector pJT4) was deposited with the ATCC on Oct. 7, 1993, and assigned ATCC Designation No. 69457.

*E. coli* transformed with pJT4-hBRK3T (SEQ ID NO:3 subcloned into expression vector pJT4) was deposited with the ATCC on Aug. 16, 1994 and assigned ATCC designation No. 69676.

*E. coli* transformed with pJT6-mBRK-3S (SEQ ID NO: 7 subcloned into expression vector pJT6) was deposited with the ATCC on Sep. 28, 1994 and assigned ATCC designation No. 69694.

*E. coli* transformed with pJT6-mBRK-3L (SEQ ID NO:7 subcloned into expression vector pJT6) was deposited with the ATCC on Sep. 28, 1994 and assigned ATCC designation No. 69695.

*E. coli* transformed with pHSK1040 (SEQ ID NO:1 subcloned into BLUESCRIPT II SK(-) was deposited with the ATCC on Oct. 12, 1994, and assigned ATCC designation No. 69703.

As is recognized in the art, there are occasionally errors in DNA and amino acid sequencing methods. As a result, the sequences encoded in the deposited material are incorporated herein by reference and controlling in the event of an error in any of the sequences found in the written description of the present invention. It is further noted that one of ordinary skill in the art reproducing Applicants' work from the written disclosure can discover any sequencing errors using routine skill. The deposit of ATCC No. 69457, ATCC No. 69676, ATCC No. 69694, ATCC No. 69695 and ATCC No. 69703 is not to be considered as an admission that the deposited material is essential to the practice of the present invention.

All publications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. An isolated BMP receptor kinase protein having amino acid sequence SEQ ID NO:2.

2. An isolated DNA sequence coding for the BMP receptor kinase protein of claim 1.

3. The DNA sequence of claim 2, wherein the DNA sequence is SEQ ID NO:1.

4. An isolated truncated BMP receptor kinase protein having amino acid sequence SEQ ID NO:4.

5. An isolated DNA sequence coding for the truncated BMP receptor kinase protein of claim 4.

6. The DNA sequence of claim 5, wherein the DNA sequence is SEQ ID NO:3.

7. An isolated soluble fragment of BMP receptor kinase protein having amino acid sequence SEQ ID No:6.

8. A DNA sequence coding for the said soluble fragment of claim 7.

9. The DNA sequence of claim 8, wherein the DNA sequence is SEQ ID NO:5.

10. An isolated BMP receptor kinase protein having amino acid sequence SEQ ID NO:8.

11. An isolated DNA sequence coding for the BMP receptor kinase protein of claim 10.

12. The DNA sequence of claim 11, wherein the DNA sequence is SEQ ID NO:7.

13. The isolated soluble fragment of BMP receptor kinase protein having amino acid sequence SEQ ID No:10.

14. A DNA sequence coding for the said soluble fragment of claim 13.

15. The DNA sequence of claim 14, wherein the DNA sequence is SEQ ID NO:9.

16. A recombinant expression vector comprising the DNA sequence of claim 5.

17. A recombinant expression vector comprising the DNA sequence of claim 6.

18. A recombinant expression vector of claim 17, having all of the identifying characteristics of pJT4-hBRK3T contained in ATCC No. 69676.

19. A recombinant expression vector comprising the DNA sequence of claim 11.

20. A recombinant expression vector comprising the DNA sequence of claim 12.

21. A recombinant expression vector of claim 20, having all of the identifying characteristics of pJT6-mBRK-3L contained in ATCC No. 69695.

22. A host cell comprising the recombinant expression vector of claim 16.

23. A host cell comprising the recombinant expression vector of claim 17.

24. A mammalian host cell comprising the recombinant expression vector of claim 18.

25. The mammalian host cell of claim 18, wherein the cell is a Chinese hamster ovary cell or a COS cell.

26. A host cell comprising the recombinant expression vector of claim 19.

27. A host cell comprising the recombinant expression vector of claim 20.

28. A mammalian host cell comprising the recombinant expression vector of claim 21.

29. The mammalian host cell of claim 28, wherein the cell is a Chinese hamster ovary cell or a COS cell.

30. A method for producing truncated BMP receptor kinase protein comprising culturing the host cell of claim 22 in a manner allowing expression of the truncated BMP receptor kinase protein and isolation of the BMP receptor kinase protein.

31. A method for producing BMP receptor kinase protein comprising culturing the host cell of claim 26 in a manner allowing expression of the BMP receptor kinase protein and isolation of the BMP receptor kinase protein.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 3601 base pairs
      (B) TYPE: nucleic acid (C) STRANDEDNESS: double
            (D) TOPOLOGY: linear (ii) MOLECULE TYPE: cDNA (ix) FEATURE:
            (A) NAME/KEY: CDS
            (B) LOCATION: join(409..3522)

(xi) SEQUENCE DESCRIPTION: SEQ ID NO:1:

```
CGCCCCCCGA CCCCGGATCG AATCCCCGCC CTCCGCACCC TGGATATGTT TTCTCCCAGA        60

CCTGGATATT TTTTTGATAT CGTGAAACTA CGAGGGAAAT AATTTGGGGG ATTTCTTCTT       120

GGCTCCCTGC TTTCCCCACA GACATGCCTT CCGTTTGGAG GGCCGCGGCA CCCCGTCCGA       180

GGCGAAGGAA CCCCCCCAGC CGCGAGGGAG AGAAATGAAG GGAATTTCTG CAGCGGCATG       240

AAAGCTCTGC AGCTAGGTCC TCTCATCAGC CATTTGTCCT TTCAAACTGT ATTGTGATAC       300

GGGCAGGATC AGTCCACGGG AGAGAAGACG AGCCTCCCGG CTGTTTCTCC GCCGGTCTAC       360

TTCCCATATT TCTTTTCTTT GCCCTCCTGA TTCTTGGCTG GCCCAGGG ATG ACT TCC       417
                                                  Met Thr Ser
                                                    1
```

```
TCG CTG CAG CGG CCC TGG CGG GTG CCC TGG CTA CCA TGG ACC ATC CTG        465
Ser Leu Gln Arg Pro Trp Arg Val Pro Trp Leu Pro Trp Thr Ile Leu
     5                  10                  15

CTG GTC AGC ACT GCG GCT GCT TCG CAG AAT CAA GAA CGG CTA TGT GCG        513
Leu Val Ser Thr Ala Ala Ala Ser Gln Asn Gln Glu Arg Leu Cys Ala
 20                  25                  30                  35

TTT AAA GAT CCG TAT CAG CAA GAC CTT GGG ATA GGT GAG AGT AGA ATC        561
Phe Lys Asp Pro Tyr Gln Gln Asp Leu Gly Ile Gly Glu Ser Arg Ile
                 40                  45                  50

TCT CAT GAA AAT GGG ACA ATA TTA TGC TCG AAA GGT AGC ACC TGC TAT        609
Ser His Glu Asn Gly Thr Ile Leu Cys Ser Lys Gly Ser Thr Cys Tyr
             55                  60                  65

GGC CTT TGG GAG AAA TCA AAA GGG GAC ATA AAT CTT GTA AAA CAA GGA        657
Gly Leu Trp Glu Lys Ser Lys Gly Asp Ile Asn Leu Val Lys Gln Gly
         70                  75                  80

TGT TGG TCT CAC ATT GGA GAT CCC CAA GAG TGT CAC TAT GAA GAA TGT        705
Cys Trp Ser His Ile Gly Asp Pro Gln Glu Cys His Tyr Glu Glu Cys
     85                  90                  95

GTA GTA ACT ACC ACT CCT CCC TCA ATT CAG AAT GGA ACA TAC CGT TTC        753
Val Val Thr Thr Thr Pro Pro Ser Ile Gln Asn Gly Thr Tyr Arg Phe
100                 105                 110                 115

TGC TGT TGT AGC ACA GAT TTA TGT AAT GTC AAC TTT ACT GAG AAT TTT        801
Cys Cys Cys Ser Thr Asp Leu Cys Asn Val Asn Phe Thr Glu Asn Phe
                120                 125                 130

CCA CCT CCT GAC ACA ACA CCA CTC AGT CCA CCT CAT TCA TTT AAC CGA        849
Pro Pro Pro Asp Thr Thr Pro Leu Ser Pro Pro His Ser Phe Asn Arg
            135                 140                 145

GAT GAG ACA ATA ATC ATT GCT TTG GCA TCA GTC TCT GTA TTA GCT GTT        897
Asp Glu Thr Ile Ile Ile Ala Leu Ala Ser Val Ser Val Leu Ala Val
        150                 155                 160

TTG ATA GTT GCC TTA TGC TTT GGA TAC AGA ATG TTG ACA GGA GAC CGT        945
Leu Ile Val Ala Leu Cys Phe Gly Tyr Arg Met Leu Thr Gly Asp Arg
    165                 170                 175

AAA CAA GGT CTT CAC AGT ATG AAC ATG ATG GAG GCA GCA GCA TCC GAA        993
Lys Gln Gly Leu His Ser Met Asn Met Met Glu Ala Ala Ala Ser Glu
180                 185                 190                 195

CCC TCT CTT GAT CTA GAT AAT CTG AAA CTG TTG GAG CTG ATT GGC CGA       1041
Pro Ser Leu Asp Leu Asp Asn Leu Lys Leu Leu Glu Leu Ile Gly Arg
                200                 205                 210
```

-continued

```
GGT CGA TAT GGA GCA GTA TAT AAA GGC TCC TTG GAT GAG CGT CCA GTT    1089
Gly Arg Tyr Gly Ala Val Tyr Lys Gly Ser Leu Asp Glu Arg Pro Val
            215                 220                 225

GCT GTA AAA GTG TTT TCC TTT GCA AAC CGT CAG AAT TTT ATC AAC GAA    1137
Ala Val Lys Val Phe Ser Phe Ala Asn Arg Gln Asn Phe Ile Asn Glu
            230                 235                 240

AAG AAC ATT TAC AGA GTG CCT TTG ATG GAA CAT GAC AAC ATT GCC CGC    1185
Lys Asn Ile Tyr Arg Val Pro Leu Met Glu His Asp Asn Ile Ala Arg
245                 250                 255

TTT ATA GTT GGA GAT GAG AGA GTC ACT GCA GAT GGA CGC ATG GAA TAT    1233
Phe Ile Val Gly Asp Glu Arg Val Thr Ala Asp Gly Arg Met Glu Tyr
260                 265                 270                 275

TTG CTT GTG ATG GAG TAC TAT CCC AAT GGA TCT TTA TGC AAG TAT TTA    1281
Leu Leu Val Met Glu Tyr Tyr Pro Asn Gly Ser Leu Cys Lys Tyr Leu
            280                 285                 290

AGT CTC CAC ACA AGT GAC TGG GTA AGC TCT TGC CGT CTT GCT CAT TCT    1329
Ser Leu His Thr Ser Asp Trp Val Ser Ser Cys Arg Leu Ala His Ser
            295                 300                 305

GTT ACT AGA GGA CTG GCT TAT CTT CAC ACA GAA TTA CCA CGA GGA GAT    1377
Val Thr Arg Gly Leu Ala Tyr Leu His Thr Glu Leu Pro Arg Gly Asp
            310                 315                 320

CAT TAT AAA CCT GCA ATT TCC CAT CGA GAT TTA AAC AGC AGA AAT GTC    1425
His Tyr Lys Pro Ala Ile Ser His Arg Asp Leu Asn Ser Arg Asn Val
325                 330                 335

CTA GTG AAA AAT GAT GGA ACC TGT GTT ATT AGT GAC TTT GGA CTG TCC    1473
Leu Val Lys Asn Asp Gly Thr Cys Val Ile Ser Asp Phe Gly Leu Ser
340                 345                 350                 355

ATG AGG CTG ACT GGA AAT AGA CTG GTG CGC CCA GGG GAG GAA GAT AAT    1521
Met Arg Leu Thr Gly Asn Arg Leu Val Arg Pro Gly Glu Glu Asp Asn
            360                 365                 370

GCA GCC ATA AGC GAG GTT GGC ACT ATC AGA TAT ATG GCA CCA GAA GTG    1569
Ala Ala Ile Ser Glu Val Gly Thr Ile Arg Tyr Met Ala Pro Glu Val
            375                 380                 385

CTA GAA GGA GCT GTG AAC TTG AGG GAC TGT GAA TCA GCT TTG AAA CAA    1617
Leu Glu Gly Ala Val Asn Leu Arg Asp Cys Glu Ser Ala Leu Lys Gln
            390                 395                 400

GTA GAC ATG TAT GCT CTT GGA CTA ATC TAT TGG GAG ATA TTT ATG AGA    1665
Val Asp Met Tyr Ala Leu Gly Leu Ile Tyr Trp Glu Ile Phe Met Arg
405                 410                 415

TGT ACA GAC CTC TTC CCA GGG GAA TCC GTA CCA GAG TAC CAG ATG GCT    1713
Cys Thr Asp Leu Phe Pro Gly Glu Ser Val Pro Glu Tyr Gln Met Ala
420                 425                 430                 435

TTT CAG ACA GAG GTT GGA AAC CAT CCC ACT TTT GAG GAT ATG CAG GTT    1761
Phe Gln Thr Glu Val Gly Asn His Pro Thr Phe Glu Asp Met Gln Val
            440                 445                 450

CTC GTG TCT AGG GAA AAA CAG AGA CCC AAG TTC CCA GAA GCC TGG AAA    1809
Leu Val Ser Arg Glu Lys Gln Arg Pro Lys Phe Pro Glu Ala Trp Lys
            455                 460                 465

GAA AAT AGC CTG GCA GTG AGG TCA CTC AAG GAG ACA ATC GAA GAC TGT    1857
Glu Asn Ser Leu Ala Val Arg Ser Leu Lys Glu Thr Ile Glu Asp Cys
            470                 475                 480

TGG GAC CAG GAT GCA GAG GCT CGG CTT ACT GCA CAG TGT GCT GAG GAA    1905
Trp Asp Gln Asp Ala Glu Ala Arg Leu Thr Ala Gln Cys Ala Glu Glu
            485                 490                 495

AGG ATG GCT GAA CTT ATG ATG ATT TGG GAA AGA AAC AAA TCT GTG AGC    1953
Arg Met Ala Glu Leu Met Met Ile Trp Glu Arg Asn Lys Ser Val Ser
500                 505                 510                 515

CCA ACA GTC AAT CCA ATG TCT ACT GCT ATG CAG AAT GAA CGC AAC CTG    2001
Pro Thr Val Asn Pro Met Ser Thr Ala Met Gln Asn Glu Arg Asn Leu
            520                 525                 530
```

```
TCA CAT AAT AGG CGT GTG CCA AAA ATT GGT CCT TAT CCA GAT TAT TCT    2049
Ser His Asn Arg Arg Val Pro Lys Ile Gly Pro Tyr Pro Asp Tyr Ser
            535                 540                 545

TCC TCC TCA TAC ATT GAA GAC TCT ATC CAT CAT ACT GAC AGC ATC GTG    2097
Ser Ser Ser Tyr Ile Glu Asp Ser Ile His His Thr Asp Ser Ile Val
            550                 555                 560

AAG AAT ATT TCC TCT GAG CAT TCT ATG TCC AGC ACA CCT TTG ACT ATA    2145
Lys Asn Ile Ser Ser Glu His Ser Met Ser Ser Thr Pro Leu Thr Ile
            565                 570                 575

GGG GAA AAA AAC CGA AAT TCA ATT AAC TAT GAA CGA CAG CAA GCA CAA    2193
Gly Glu Lys Asn Arg Asn Ser Ile Asn Tyr Glu Arg Gln Gln Ala Gln
580                 585                 590                 595

GCT CGA ATC CCC AGC CCT GAA ACA AGT GTC ACC AGC CTC TCC ACC AAC    2241
Ala Arg Ile Pro Ser Pro Glu Thr Ser Val Thr Ser Leu Ser Thr Asn
                600                 605                 610

ACA ACA ACC ACA AAC ACC ACA GGA CTC ACG CCA AGT ACT GGC ATG ACT    2289
Thr Thr Thr Thr Asn Thr Thr Gly Leu Thr Pro Ser Thr Gly Met Thr
            615                 620                 625

ACT ATA TCT GAG ATG CCA TAC CCA GAT GAA ACA AAT CTG CAT ACC ACA    2337
Thr Ile Ser Glu Met Pro Tyr Pro Asp Glu Thr Asn Leu His Thr Thr
            630                 635                 640

AAT GTT GCA CAG TCA ATT GGG CCA ACC CCT GTC TGC TTA CAG CTG ACA    2385
Asn Val Ala Gln Ser Ile Gly Pro Thr Pro Val Cys Leu Gln Leu Thr
            645                 650                 655

GAA GAA GAC TTG GAA ACC AAC AAG CTA GAC CCA AAA GAA GTT GAT AAG    2433
Glu Glu Asp Leu Glu Thr Asn Lys Leu Asp Pro Lys Glu Val Asp Lys
660                 665                 670                 675

AAC CTC AAG GAA AGC TCT GAT GAG AAT CTC ATG GAG CAC TCT CTT AAA    2481
Asn Leu Lys Glu Ser Ser Asp Glu Asn Leu Met Glu His Ser Leu Lys
                680                 685                 690

CAG TTC AGT GGC CCA GAC CCA CTG AGC AGT ACT AGT TCT AGC TTG CTT    2529
Gln Phe Ser Gly Pro Asp Pro Leu Ser Ser Thr Ser Ser Ser Leu Leu
            695                 700                 705

TAC CCA CTC ATA AAA CTT GCA GTA GAA GCA ACT GGA CAG CAG GAC TTC    2577
Tyr Pro Leu Ile Lys Leu Ala Val Glu Ala Thr Gly Gln Gln Asp Phe
            710                 715                 720

ACA CAG ACT GCA AAT GGC CAA GCA TGT TTG ATT CCT GAT GTT CTG CCT    2625
Thr Gln Thr Ala Asn Gly Gln Ala Cys Leu Ile Pro Asp Val Leu Pro
725                 730                 735

ACT CAG ATC TAT CCT CTC CCC AAG CAG CAG AAC CTT CCC AAG AGA CCT    2673
Thr Gln Ile Tyr Pro Leu Pro Lys Gln Gln Asn Leu Pro Lys Arg Pro
740                 745                 750                 755

ACT AGT TTG CCT TTG AAC ACC AAA AAT TCA ACA AAA GAG CCC CGG CTA    2721
Thr Ser Leu Pro Leu Asn Thr Lys Asn Ser Thr Lys Glu Pro Arg Leu
            760                 765                 770

AAA TTT GGC AGC AAG CAC AAA TCA AAC TTG AAA CAA GTC GAA ACT GGA    2769
Lys Phe Gly Ser Lys His Lys Ser Asn Leu Lys Gln Val Glu Thr Gly
            775                 780                 785

GTT GCC AAG ATG AAT ACA ATC AAT GCA GCA GAA CCT CAT GTG GTG ACA    2817
Val Ala Lys Met Asn Thr Ile Asn Ala Ala Glu Pro His Val Val Thr
            790                 795                 800

GTC ACC ATG AAT GGT GTG GCA GGT AGA AAC CAC AGT GTT AAC TCC CAT    2865
Val Thr Met Asn Gly Val Ala Gly Arg Asn His Ser Val Asn Ser His
805                 810                 815

GCT GCC ACA ACC CAA TAT GCC AAT GGG ACA GTA CTA TCT GGC CAA ACA    2913
Ala Ala Thr Thr Gln Tyr Ala Asn Gly Thr Val Leu Ser Gly Gln Thr
820                 825                 830                 835

ACC AAC ATA GTG ACA CAT AGG GCC CAA GAA ATG TTG CAG AAT CAG TTT    2961
Thr Asn Ile Val Thr His Arg Ala Gln Glu Met Leu Gln Asn Gln Phe
```

-continued

```
                840                 845                 850
ATT GGT GAG GAC ACC CGG CTG AAT ATT AAT TCC AGT CCT GAT GAG CAT       3009
Ile Gly Glu Asp Thr Arg Leu Asn Ile Asn Ser Ser Pro Asp Glu His
                855                 860                 865

GAG CCT TTA CTG AGA CGA GAG CAA CAA GCT GGC CAT GAT GAA GGT GTT       3057
Glu Pro Leu Leu Arg Arg Glu Gln Gln Ala Gly His Asp Glu Gly Val
            870                 875                 880

CTG GAT CGT CTT GTG GAC AGG AGG GAA CGG CCA CTA GAA GGT GGC CGA       3105
Leu Asp Arg Leu Val Asp Arg Arg Glu Arg Pro Leu Glu Gly Gly Arg
        885                 890                 895

ACT AAT TCC AAT AAC AAC AAC AGC AAT CCA TGT TCA GAA CAA GAT GTT       3153
Thr Asn Ser Asn Asn Asn Asn Ser Asn Pro Cys Ser Glu Gln Asp Val
900                 905                 910                 915

CTT GCA CAG GGT GTT CCA AGC ACA GCA GAT CCT GGG CCA TCA AAG           3201
Leu Ala Gln Gly Val Pro Ser Thr Ala Ala Asp Pro Gly Pro Ser Lys
                920                 925                 930

CCC AGA AGA GCA CAG AGG CCT AAT TCT CTG GAT CTT TCA GCC ACA AAT       3249
Pro Arg Arg Ala Gln Arg Pro Asn Ser Leu Asp Leu Ser Ala Thr Asn
            935                 940                 945

GTC CTG GAT GGC AGC AGT ATA CAG ATA GGT GAG TCA ACA CAA GAT GGC       3297
Val Leu Asp Gly Ser Ser Ile Gln Ile Gly Glu Ser Thr Gln Asp Gly
        950                 955                 960

AAA TCA GGA TCA GGT GAA AAG ATC AAG AAA CGT GTG AAA ACT CCC TAT       3345
Lys Ser Gly Ser Gly Glu Lys Ile Lys Lys Arg Val Lys Thr Pro Tyr
965                 970                 975

TCT CTT AAG CGG TGG CGC CCC TCC ACC TGG GTC ATC TCC ACT GAA TCG       3393
Ser Leu Lys Arg Trp Arg Pro Ser Thr Trp Val Ile Ser Thr Glu Ser
980                 985                 990                 995

CTG GAC TGT GAA GTC AAC AAT AAT GGC AGT AAC AGG GCA GTT CAT TCC       3441
Leu Asp Cys Glu Val Asn Asn Asn Gly Ser Asn Arg Ala Val His Ser
                1000                1005                1010

AAA TCC AGC ACT GCT GTT TAC CTT GCA GAA GGA GGC ACT GCT ACA ACC       3489
Lys Ser Ser Thr Ala Val Tyr Leu Ala Glu Gly Gly Thr Ala Thr Thr
            1015                1020                1025

ATG GTG TCT AAA GAT ATA GGA ATG AAC TGT CTG TGAAATGTTT TCAAGCCTAT     3542
Met Val Ser Lys Asp Ile Gly Met Asn Cys Leu
        1030                1035

GGAGTGAAAT TATTTTTTGC ATCATTTAAA CATGCAGAAG ATGTTAAAA AAAAAAAAA       3601

(2) INFORMATION FOR SEQ ID NO:2:

(i) SEQUENCE CHARACTERISTICS:
        (A) LENGTH: 1038 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
                20                  25                  30

Leu Cys Ala Phe Lys Asp Pro Tyr Gln Gln Asp Leu Gly Ile Gly Glu
            35                  40                  45

Ser Arg Ile Ser His Glu Asn Gly Thr Ile Leu Cys Ser Lys Gly Ser
        50                  55                  60

Thr Cys Tyr Gly Leu Trp Glu Lys Ser Leu Gly Asp Ile Asn Leu Val
65                  70                  75                  80
```

```
Lys Gln Gly Cys Trp Ser His Ile Gly Asp Pro Gln Glu Cys His Tyr
                85                  90                  95
Glu Glu Cys Val Val Thr Thr Pro Pro Ser Ile Gln Asn Gly Thr
            100                 105                 110
Tyr Arg Phe Cys Cys Cys Ser Thr Asp Leu Cys Asn Val Asn Phe Thr
            115                 120                 125
Glu Asn Phe Pro Pro Asp Thr Thr Pro Leu Ser Pro His Ser
130                 135                 140
Phe Asn Arg Asp Glu Thr Ile Ile Ala Leu Ala Ser Val Ser Val
145                 150                 155                 160
Leu Ala Val Leu Ile Val Ala Leu Cys Phe Gly Tyr Arg Met Leu Thr
                165                 170                 175
Gly Asp Arg Lys Gln Gly Leu His Ser Met Asn Met Met Glu Ala Ala
                180                 185                 190
Ala Ser Glu Pro Ser Leu Asp Leu Asp Asn Leu Lys Leu Leu Glu Leu
            195                 200                 205
Ile Gly Arg Gly Arg Tyr Gly Ala Val Tyr Lys Gly Ser Leu Asp Glu
            210                 215                 220
Arg Pro Val Ala Val Lys Val Phe Ser Phe Ala Asn Arg Gln Asn Phe
225                 230                 235                 240
Ile Asn Glu Lys Asn Ile Tyr Arg Val Pro Leu Met Glu His Asp Asn
                245                 250                 255
Ile Ala Arg Phe Ile Val Gly Asp Glu Arg Val Thr Ala Asp Gly Arg
                260                 265                 270
Met Glu Tyr Leu Leu Val Met Glu Tyr Tyr Pro Asn Gly Ser Leu Cys
                275                 280                 285
Lys Tyr Leu Ser Leu His Thr Ser Asp Trp Val Ser Ser Cys Arg Leu
                290                 295                 300
Ala His Ser Val Thr Arg Gly Leu Ala Tyr Leu His Thr Glu Leu Pro
305                 310                 315                 320
Arg Gly Asp His Tyr Lys Pro Ala Ile Ser His Arg Asp Leu Asn Ser
                325                 330                 335
Arg Asn Val Leu Val Lys Asn Asp Gly Thr Cys Val Ile Ser Asp Phe
                340                 345                 350
Gly Leu Ser Met Arg Leu Thr Gly Asn Arg Leu Val Arg Pro Gly Glu
            355                 360                 365
Glu Asp Asn Ala Ala Ile Ser Glu Val Gly Thr Ile Arg Tyr Met Ala
            370                 375                 380
Pro Glu Val Leu Glu Gly Ala Val Asn Leu Arg Asp Cys Glu Ser Ala
385                 390                 395                 400
Leu Lys Gln Val Asp Met Tyr Ala Leu Gly Leu Ile Tyr Trp Glu Ile
                405                 410                 415
Phe Met Arg Cys Thr Asp Leu Phe Pro Gly Glu Ser Val Pro Glu Tyr
                420                 425                 430
Gln Met Ala Phe Gln Thr Glu Val Gly Asn His Pro Thr Phe Glu Asp
            435                 440                 445
Met Gln Val Leu Val Ser Arg Glu Lys Gln Arg Pro Lys Phe Pro Glu
450                 455                 460
Ala Trp Lys Glu Asn Ser Leu Ala Val Arg Ser Leu Lys Glu Thr Ile
465                 470                 475                 480
Glu Asp Cys Trp Asp Gln Asp Ala Glu Ala Arg Leu Thr Ala Gln Cys
                485                 490                 495
Ala Glu Glu Arg Met Ala Glu Leu Met Met Ile Trp Glu Arg Asn Lys
```

-continued

```
                500                 505                 510
Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
    530                 535                 540

Asp Tyr Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
    610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
            660                 665                 670

Val Asp Lys Asn Leu Lys Glu Ser Ser Asp Glu Asn Leu Met Glu His
        675                 680                 685

Ser Leu Lys Gln Phe Ser Gly Pro Asp Pro Leu Ser Ser Thr Ser Ser
    690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
        755                 760                 765

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
            820                 825                 830

Gly Gln Thr Thr Asn Ile Val Thr His Arg Ala Gln Glu Met Leu Gln
        835                 840                 845

Asn Gln Phe Ile Gly Glu Asp Thr Arg Leu Asn Ile Asn Ser Ser Pro
    850                 855                 860

Asp Glu His Glu Pro Leu Leu Arg Arg Glu Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Ser Asn Pro Cys Ser Glu
            900                 905                 910

Gln Asp Val Leu Ala Gln Gly Val Pro Ser Thr Ala Ala Asp Pro Gly
        915                 920                 925
```

```
Pro Ser Lys Pro Arg Arg Ala Gln Arg Pro Asn Ser Leu Asp Leu Ser
    930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val Asn Asn Gly Ser Asn Arg Ala
        995                 1000                1005

Val His Ser Lys Ser Ser Thr Ala Val Tyr Leu Ala Glu Gly Gly Thr
    1010                1015                1020

Ala Thr Thr Met Val Ser Lys Asp Ile Gly Met Asn Cys Leu
1025                1030                1035

(2) INFORMATION FOR SEQ ID NO:3:

(i) SEQUENCE CHARACTERISTICS:
        (A) LENGTH: 2157 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: join(409..2154)

(xi) SEQUENCE DESCRIPTION: SEQ ID NO:3:

CGCCCCCCGA CCCCGGATCG AATCCCCGCC CTCCGCACCC TGGATATGTT TTCTCCCAGA      60

CCTGGATATT TTTTTGATAT CGTGAAACTA CGAGGGAAAT AATTTGGGGG ATTTCTTCTT    120

GGCTCCCTGC TTTCCCCACA GACATGCCTT CCGTTTGGAG GGCCGCGGCA CCCCGTCCGA    180

GGCGAAGGAA CCCCCCCAGC CGCGAGGGAG AGAAATGAAG GGAATTTCTG CAGCGGCATG    240

AAAGCTCTGC AGCTAGGTCC TCTCATCAGC CATTTGTCCT TCAAACTGT ATTGTGATAC     300

GGGCAGGATC AGTCCACGGG AGAGAAGACG AGCCTCCCGG CTGTTTCTCC GCCGGTCTAC    360

TTCCCATATT TCTTTTCTTT GCCCTCCTGA TTCTTGGCTG GCCCAGGG ATG ACT TCC     417
                                                    Met Thr Ser
                                                     1

TCG CTG CAG CGG CCC TGG CGG GTG CCC TGG CTA CCA TGG ACC ATC CTG     465
Ser Leu Gln Arg Pro Trp Arg Val Pro Trp Leu Pro Trp Thr Ile Leu
    5                   10                  15

CTG GTC AGC ACT GCG GCT GCT TCG CAG AAT CAA GAA CGG CTA TGT GCG     513
Leu Val Ser Thr Ala Ala Ala Ser Gln Asn Gln Glu Arg Leu Cys Ala
 20                  25                  30                  35

TTT AAA GAT CCG TAT CAG CAA GAC CTT GGG ATA GGT GAG AGT AGA ATC     561
Phe Lys Asp Pro Tyr Gln Gln Asp Leu Gly Ile Gly Glu Ser Arg Ile
                 40                  45                  50

TCT CAT GAA AAT GGG ACA ATA TTA TGC TCG AAA GGT AGC ACC TGC TAT     609
Ser His Glu Asn Gly Thr Ile Leu Cys Ser Lys Gly Ser Thr Cys Tyr
             55                  60                  65

GGC CTT TGG GAG AAA TCA AAA GGG GAC ATA AAT CTT GTA AAA CAA GGA     657
Gly Leu Trp Glu Lys Ser Lys Gly Asp Ile Asn Leu Val Lys Gln Gly
         70                  75                  80

TGT TGG TCT CAC ATT GGA GAT CCC CAA GAG TGT CAC TAT GAA GAA TGT     705
Cys Trp Ser His Ile Gly Asp Pro Gln Glu Cys His Tyr Glu Glu Cys
     85                  90                  95
```

```
                                                -continued

GTA GTA ACT ACC ACT CCT CCC TCA ATT CAG AAT GGA ACA TAC CGT TTC        753
Val Val Thr Thr Thr Pro Pro Ser Ile Gln Asn Gly Thr Tyr Arg Phe
100             105                 110                 115

TGC TGT TGT AGC ACA GAT TTA TGT AAT GTC AAC TTT ACT GAG AAT TTT        801
Cys Cys Cys Ser Thr Asp Leu Cys Asn Val Asn Phe Thr Glu Asn Phe
                120                 125                 130

CCA CCT CCT GAC ACA ACA CCA CTC AGT CCA CCT CAT TCA TTT AAC CGA        849
Pro Pro Pro Asp Thr Thr Pro Leu Ser Pro Pro His Ser Phe Asn Arg
                135                 140                 145

GAT GAG ACA ATA ATC ATT GCT TTG GCA TCA GTC TCT GTA TTA GCT GTT        897
Asp Glu Thr Ile Ile Ile Ala Leu Ala Ser Val Ser Val Leu Ala Val
            150                 155                 160

TTG ATA GTT GCC TTA TGC TTT GGA TAC AGA ATG TTG ACA GGA GAC CGT        945
Leu Ile Val Ala Leu Cys Phe Gly Tyr Arg Met Leu Thr Gly Asp Arg
165             170                 175

AAA CAA GGT CTT CAC AGT ATG AAC ATG ATG GAG GCA GCA GCA TCC GAA        993
Lys Gln Gly Leu His Ser Met Asn Met Met Glu Ala Ala Ala Ser Glu
180             185                 190                 195

CCC TCT CTT GAT CTA GAT AAT CTG AAA CTG TTG GAG CTG ATT GGC CGA       1041
Pro Ser Leu Asp Leu Asp Asn Leu Lys Leu Leu Glu Leu Ile Gly Arg
                200                 205                 210

GGT CGA TAT GGA GCA GTA TAT AAA GGC TCC TTG GAT GAG CGT CCA GTT       1089
Gly Arg Tyr Gly Ala Val Tyr Lys Gly Ser Leu Asp Glu Arg Pro Val
                215                 220                 225

GCT GTA AAA GTG TTT TCC TTT GCA AAC CGT CAG AAT TTT ATC AAC GAA       1137
Ala Val Lys Val Phe Ser Phe Ala Asn Arg Gln Asn Phe Ile Asn Glu
                230                 235                 240

AAG AAC ATT TAC AGA GTG CCT TTG ATG GAA CAT GAC AAC ATT GCC CGC       1185
Lys Asn Ile Tyr Arg Val Pro Leu Met Glu His Asp Asn Ile Ala Arg
                245                 250                 255

TTT ATA GTT GGA GAT GAG AGA GTC ACT GCA GAT GGA CGC ATG GAA TAT       1233
Phe Ile Val Gly Asp Glu Arg Val Thr Ala Asp Gly Arg Met Glu Tyr
260             265                 270                 275

TTG CTT GTG ATG GAG TAC TAT CCC AAT GGA TCT TTA TGC AAG TAT TTA       1281
Leu Leu Val Met Glu Tyr Tyr Pro Asn Gly Ser Leu Cys Lys Tyr Leu
                280                 285                 290

AGT CTC CAC ACA AGT GAC TGG GTA AGC TCT TGC CGT CTT GCT CAT TCT       1329
Ser Leu His Thr Ser Asp Trp Val Ser Ser Cys Arg Leu Ala His Ser
                295                 300                 305

GTT ACT AGA GGA CTG GCT TAT CTT CAC ACA GAA TTA CCA CGA GGA GAT       1377
Val Thr Arg Gly Leu Ala Tyr Leu His Thr Glu Leu Pro Arg Gly Asp
                310                 315                 320

CAT TAT AAA CCT GCA ATT TCC CAT CGA GAT TTA AAC AGC AGA AAT GTC       1425
His Tyr Lys Pro Ala Ile Ser His Arg Asp Leu Asn Ser Arg Asn Val
325             330                 335

CTA GTG AAA AAT GAT GGA ACC TGT GTT ATT AGT GAC TTT GGA CTG TCC       1473
Leu Val Lys Asn Asp Gly Thr Cys Val Ile Ser Asp Phe Gly Leu Ser
340             345                 350                 355

ATG AGG CTG ACT GGA AAT AGA CTG GTG CGC CCA GGG GAG GAA GAT AAT       1521
Met Arg Leu Thr Gly Asn Arg Leu Val Arg Pro Gly Glu Glu Asp Asn
                360                 365                 370

GCA GCC ATA AGC GAG GTT GGC ACT ATC AGA TAT ATG GCA CCA GAA GTG       1569
Ala Ala Ile Ser Glu Val Gly Thr Ile Arg Tyr Met Ala Pro Glu Val
                375                 380                 385

CTA GAA GGA GCT GTG AAC TTG AGG GAC TGT GAA TCA GCT TTG AAA CAA       1617
Leu Glu Gly Ala Val Asn Leu Arg Asp Cys Glu Ser Ala Leu Lys Gln
                390                 395                 400

GTA GAC ATG TAT GCT CTT GGA CTA ATC TAT TGG GAG ATA TTT ATG AGA       1665
Val Asp Met Tyr Ala Leu Gly Leu Ile Tyr Trp Glu Ile Phe Met Arg
                405                 410                 415
```

```
TGT ACA GAC CTC TTC CCA GGG GAA TCC GTA CCA GAG TAC CAG ATG GCT    1713
Cys Thr Asp Leu Phe Pro Gly Glu Ser Val Pro Glu Tyr Gln Met Ala
420                 425                 430                 435

TTT CAG ACA GAG GTT GGA AAC CAT CCC ACT TTT GAG GAT ATG CAG GTT    1761
Phe Gln Thr Glu Val Gly Asn His Pro Thr Phe Glu Asp Met Gln Val
            440                 445                 450

CTC GTG TCT AGG GAA AAA CAG AGA CCC AAG TTC CCA GAA GCC TGG AAA    1809
Leu Val Ser Arg Glu Lys Gln Arg Pro Lys Phe Pro Glu Ala Trp Lys
        455                 460                 465

GAA AAT AGC CTG GCA GTG AGG TCA CTC AAG GAG ACA ATC GAA GAC TGT    1857
Glu Asn Ser Leu Ala Val Arg Ser Leu Lys Glu Thr Ile Glu Asp Cys
    470                 475                 480

TGG GAC CAG GAT GCA GAG GCT CGG CTT ACT GCA CAG TGT GCT GAG GAA    1905
Trp Asp Gln Asp Ala Glu Ala Arg Leu Thr Ala Gln Cys Ala Glu Glu
485                 490                 495

AGG ATG GCT GAA CTT ATG ATG ATT TGG GAA AGA AAC AAA TCT GTG AGC    1953
Arg Met Ala Glu Leu Met Met Ile Trp Glu Arg Asn Lys Ser Val Ser
500                 505                 510                 515

CCA ACA GTC AAT CCA ATG TCT ACT GCT ATG CAG AAT GAA CGC AAC CTG    2001
Pro Thr Val Asn Pro Met Ser Thr Ala Met Gln Asn Glu Arg Asn Leu
            520                 525                 530

TCA CAT AAT AGG CGT GTG CCA AAA ATT GGT CCT TAT CCA GAT TAT TCT    2049
Ser His Asn Arg Arg Val Pro Lys Ile Gly Pro Tyr Pro Asp Tyr Ser
        535                 540                 545

TCC TCC TCA TAC ATT GAA GAC TCT ATC CAT CAT ACT GAC AGC ATC GTG    2097
Ser Ser Ser Tyr Ile Glu Asp Ser Ile His His Thr Asp Ser Ile Val
    550                 555                 560

AAG AAT ATT TCC TCT GAG CAT TCT ATG TCC AGC ACA CCT TTG ACT ATA    2145
Lys Asn Ile Ser Ser Glu His Ser Met Ser Ser Thr Pro Leu Thr Ile
565                 570                 575

GGG GAA AAA TAA                                                    2157
Gly Glu Lys
580
```

(2) INFORMATION FOR SEQ ID NO:4:

(i) SEQUENCE CHARACTERISTICS:
        (A) LENGTH: 582 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
            85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
```

-continued

```
            115                 120                 125
Glu Asn Phe Pro Pro Asp Thr Thr Pro Leu Ser Pro His Ser
        130                 135                 140

Phe Asn Arg Asp Glu Thr Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
            195                 200                 205

Ile Gly Arg Gly Arg Tyr Gly Ala Val Tyr Lys Gly Ser Leu Asp Glu
210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
            275                 280                 285

Lys Tyr Leu Ser Leu His Thr Ser Asp Trp Val Ser Ser Cys Arg Leu
            290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
            325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
            355                 360                 365

Glu Asp Asn Ala Ala Ile Ser Glu Val Gly Thr Ile Arg Tyr Met Ala
            370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
            435                 440                 445

Met Gln Val Leu Val Ser Arg Glu Lys Gln Arg Pro Lys Phe Pro Glu
450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
            485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
            515                 520                 525

Arg Asn Leu Ser His Asn Arg Arg Val Pro Lys Ile Gly Pro Tyr Pro
            530                 535                 540
```

```
Asp Tyr Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys
            580
```

(2) INFORMATION FOR SEQ ID NO:5:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: join(19..468)

(xi) SEQUENCE DESCRIPTION: SEQ ID NO:5:

```
TTCTTGGCTG GCCCAGGG ATG ACT TCC TCG CTG CAG CGG CCC TGG CGG GTG        51
                   Met Thr Ser Ser Leu Gln Arg Pro Trp Arg Val
                    1               5                       10

CCC TGG CTA CCA TGG ACC ATC CTG CTG GTC AGC ACT GCG GCT GCT TCG        99
Pro Trp Leu Pro Trp Thr Ile Leu Leu Val Ser Thr Ala Ala Ala Ser
            15                  20                  25

CAG AAT CAA GAA CGG CTA TGT GCG TTT AAA GAT CCG TAT CAG CAA GAC       147
Gln Asn Gln Glu Arg Leu Cys Ala Phe Lys Asp Pro Tyr Gln Gln Asp
        30                  35                  40

CTT GGG ATA GGT GAG AGT AGA ATC TCT CAT GAA AAT GGG ACA ATA TTA       195
Leu Gly Ile Gly Glu Ser Arg Ile Ser His Glu Asn Gly Thr Ile Leu
    45                  50                  55

TGC TCG AAA GGT AGC ACC TGC TAT GGC CTT TGG GAG AAA TCA AAA GGG       243
Cys Ser Lys Gly Ser Thr Cys Tyr Gly Leu Trp Glu Lys Ser Lys Gly
60                  65                  70                  75

GAC ATA AAT CTT GTA AAA CAA GGA TGT TGG TCT CAC ATT GGA GAT CCC       291
Asp Ile Asn Leu Val Lys Gln Gly Cys Trp Ser His Ile Gly Asp Pro
                80                  85                  90

CAA GAG TGT CAC TAT GAA GAA TGT GTA GTA ACT ACC ACT CCT CCC TCA       339
Gln Glu Cys His Tyr Glu Glu Cys Val Val Thr Thr Thr Pro Pro Ser
            95                  100                 105

ATT CAG AAT GGA ACA TAC CGT TTC TGC TGT TGT AGC ACA GAT TTA TGT       387
Ile Gln Asn Gly Thr Tyr Arg Phe Cys Cys Cys Ser Thr Asp Leu Cys
        110                 115                 120

AAT GTC AAC TTT ACT GAG AAT TTT CCA CCT CCT GAC ACA ACA CCA CTC       435
Asn Val Asn Phe Thr Glu Asn Phe Pro Pro Pro Asp Thr Thr Pro Leu
    125                 130                 135

AGT CCA CCT CAT TCA TTT AAC CGA GAT GAG ACA TGA                       471
Ser Pro Pro His Ser Phe Asn Arg Asp Glu Thr
140                 145                 150
```

(2) INFORMATION FOR SEQ ID NO:6:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:6:

```
Met Thr Ser Ser Leu Gln Arg Pro Trp Arg Val Pro Trp Leu Pro Trp
 1               5                  10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr
145             150

(2) INFORMATION FOR SEQ ID NO:7:

(i) SEQUENCE CHARACTERISTICS:
        (A) LENGTH: 3508 base pairs
        (B) TYPE: nucleic acid
        (C) STRANDEDNESS: double
        (D) TOPOLOGY: linear (ii) MOLECULE TYPE: cDNA (ix) FEATURE:
         (A) NAME/KEY: CDS
         (B) LOCATION: join(17..3130)

(xi) SEQUENCE DESCRIPTION: SEQ ID NO:7:

CTTTGCTGGC CCAGGG ATG ACT TCC TCG CTG CAT CGG CCC TTT CGG GTG           49
               Met Thr Ser Ser Leu His Arg Pro Phe Arg Val
                 1               5                  10

CCC TGG CTG CTA TGG GCC GTC CTG CTG GTC AGC ACT ACG GCT GCT TCT         97
Pro Trp Leu Leu Trp Ala Val Leu Leu Val Ser Thr Thr Ala Ala Ser
            15                  20                  25

CAG AAT CAA GAA CGG CTG TGT GCA TTT AAA GAT CCA TAT CAA CAA GAT        145
Gln Asn Gln Glu Arg Leu Cys Ala Phe Lys Asp Pro Tyr Gln Gln Asp
        30                  35                  40

CTT GGG ATA GGT GAG AGT CGA ATC TCT CAT GAA AAT GGG ACA ATA TTA        193
Leu Gly Ile Gly Glu Ser Arg Ile Ser His Glu Asn Gly Thr Ile Leu
    45                  50                  55

TGT TCC AAA GGG AGC ACG TGT TAT GGT CTG TGG GAG AAA TCA AAA GGG        241
Cys Ser Lys Gly Ser Thr Cys Tyr Gly Leu Trp Glu Lys Ser Lys Gly
60                  65                  70                  75

GAC ATC AAT CTT GTG AAA CAA GGA TGT TGG TCT CAC ATC GGT GAT CCC        289
Asp Ile Asn Leu Val Lys Gln Gly Cys Trp Ser His Ile Gly Asp Pro
                80                  85                  90

CAA GAG TGC CAC TAT GAA GAG TGT GTA GTA ACT ACC ACC CCA CCC TCA        337
Gln Glu Cys His Tyr Glu Glu Cys Val Val Thr Thr Thr Pro Pro Ser
            95                  100                 105

ATT CAG AAT GGA ACG TAC CGC TTT TGC TGC TGT AGT ACA GAT TTA TGT        385
Ile Gln Asn Gly Thr Tyr Arg Phe Cys Cys Cys Ser Thr Asp Leu Cys
        110                 115                 120
```

-continued

| | | |
|---|---|---|
| AAT GTC AAC TTT ACT GAG AAC TTT CCA CCC CCT GAC ACA ACA CCA CTC<br>Asn Val Asn Phe Thr Glu Asn Phe Pro Pro Pro Asp Thr Thr Pro Leu<br>125                            130                       135 | | 433 |
| AGT CCA CCT CAT TCA TTT AAT CGA GAT GAA ACG ATA ATC ATT GCT TTG<br>Ser Pro Pro His Ser Phe Asn Arg Asp Glu Thr Ile Ile Ile Ala Leu<br>140                       145                     150                     155 | | 481 |
| GCA TCA GTT TCT GTG TTA GCT GTT TTG ATA GTC GCC TTA TGT TTT GGA<br>Ala Ser Val Ser Val Leu Ala Val Leu Ile Val Ala Leu Cys Phe Gly<br>                 160                     165                     170 | | 529 |
| TAC AGA ATG TTG ACA GGA GAC CGG AAA CAG GGT CTT CAC AGC ATG AAC<br>Tyr Arg Met Leu Thr Gly Asp Arg Lys Gln Gly Leu His Ser Met Asn<br>            175                     180                     185 | | 577 |
| ATG ATG GAG GCG GCA GCA GCA GAG CCC TCC CTT GAC CTG GAT AAC CTG<br>Met Met Glu Ala Ala Ala Ala Glu Pro Ser Leu Asp Leu Asp Asn Leu<br>190                            195                     200 | | 625 |
| AAG CTG CTG GAG CTG ATT GGA CGG GGT CGA TAC GGA GCA GTA TAT AAA<br>Lys Leu Leu Glu Leu Ile Gly Arg Gly Arg Tyr Gly Ala Val Tyr Lys<br>           205                     210                     215 | | 673 |
| GGT TCC TTG GAT GAG CGT CCA GTT GCT GTA AAA GTA TTT TCT TTT GCA<br>Gly Ser Leu Asp Glu Arg Pro Val Ala Val Lys Val Phe Ser Phe Ala<br>220                            225                     230                   235 | | 721 |
| AAC CGT CAG AAT TTT ATA AAT GAA AAA AAC ATT TAC AGA GTG CCT TTG<br>Asn Arg Gln Asn Phe Ile Asn Glu Lys Asn Ile Tyr Arg Val Pro Leu<br>                 240                     245                     250 | | 769 |
| ATG GAA CAT GAC AAC ATT GCT CGC TTC ATA GTT GGA GAC GAG AGG CTC<br>Met Glu His Asp Asn Ile Ala Arg Phe Ile Val Gly Asp Glu Arg Leu<br>           255                     260                     265 | | 817 |
| ACT GCA GAC GGC CGC ATG GAG TAT TTG CTT GTG ATG GAG TAT TAT CCC<br>Thr Ala Asp Gly Arg Met Glu Tyr Leu Leu Val Met Glu Tyr Tyr Pro<br>           270                     275                     280 | | 865 |
| AAT GGA TCT CTG TGC AAA TAT CTG AGT CTC CAC ACA AGT GAT TGG GTA<br>Asn Gly Ser Leu Cys Lys Tyr Leu Ser Leu His Thr Ser Asp Trp Val<br>285                            290                     295 | | 913 |
| AGC TCT TGC CGT CTG GCT CAT TCT GTG ACT AGA GGA CTG GCT TAT CTT<br>Ser Ser Cys Arg Leu Ala His Ser Val Thr Arg Gly Leu Ala Tyr Leu<br>300                            305                     310                   315 | | 961 |
| CAC ACA GAA TTA CCA CGA GGA GAT CAT TAT AAA CCC GCA ATC TCC CAC<br>His Thr Glu Leu Pro Arg Gly Asp His Tyr Lys Pro Ala Ile Ser His<br>                 320                     325                     330 | | 1009 |
| CGA GAT TTA AAC AGC AGG AAT GTC CTG GTA AAG AAT GAC GGC GCG TGT<br>Arg Asp Leu Asn Ser Arg Asn Val Leu Val Lys Asn Asp Gly Ala Cys<br>                 335                     340                     345 | | 1057 |
| GTT ATC AGT GAC TTT GGT TTA TCC ATG AGG CTA ACT GGA AAT CGG CTG<br>Val Ile Ser Asp Phe Gly Leu Ser Met Arg Leu Thr Gly Asn Arg Leu<br>           350                     355                     360 | | 1105 |
| GTG CGC CCA GGG GAA GAA GAT AAT GCG GCT ATA AGT GAG GTT GGC ACA<br>Val Arg Pro Gly Glu Glu Asp Asn Ala Ala Ile Ser Glu Val Gly Thr<br>365                            370                     375 | | 1153 |
| ATT CGC TAT ATG GCA CCA GAA GTG CTA GAA GGA GCT GTG AAC CTG AGG<br>Ile Arg Tyr Met Ala Pro Glu Val Leu Glu Gly Ala Val Asn Leu Arg<br>380                            385                     390                   395 | | 1201 |
| GAC TGT GAG TCA GCT CTG AAG CAA GTG GAC ATG TAT GCG CTT GGA CTC<br>Asp Cys Glu Ser Ala Leu Lys Gln Val Asp Met Tyr Ala Leu Gly Leu<br>                 400                     405                     410 | | 1249 |
| ATC TAC TGG GAG GTG TTT ATG AGG TGT ACA GAC CTC TTC CCA GGT GAA<br>Ile Tyr Trp Glu Val Phe Met Arg Cys Thr Asp Leu Phe Pro Gly Glu<br>           415                     420                     425 | | 1297 |
| TCT GTA CCA GAT TAC CAG ATG GCT TTT CAG ACA GAA GTT GGA AAC CAT<br>Ser Val Pro Asp Tyr Gln Met Ala Phe Gln Thr Glu Val Gly Asn His<br>430                            435                     440 | | 1345 |

-continued

```
CCC ACA TTT GAG GAT ATG CAG GTT CTT GTG TCC AGA GAG AAG CAG AGA         1393
Pro Thr Phe Glu Asp Met Gln Val Leu Val Ser Arg Glu Lys Gln Arg
    445                 450                 455

CCC AAG TTC CCA GAA GCC TGG AAA GAA AAT AGC CTG GCA GTG AGG TCA         1441
Pro Lys Phe Pro Glu Ala Trp Lys Glu Asn Ser Leu Ala Val Arg Ser
460                 465                 470                 475

CTC AAG GAA ACA ATT GAA GAC TGC TGG GAC CAG GAT GCA GAG GCT CGG         1489
Leu Lys Glu Thr Ile Glu Asp Cys Trp Asp Gln Asp Ala Glu Ala Arg
                480                 485                 490

CTC ACT GCA CAG TGT GCT GAG GAG AGG ATG GCT GAA CTC ATG ATG ATA         1537
Leu Thr Ala Gln Cys Ala Glu Glu Arg Met Ala Glu Leu Met Met Ile
            495                 500                 505

TGG GAG AGA AAC AAG TCT GTG AGC CCA ACG GTC AAC CCA ATG TCA ACT         1585
Trp Glu Arg Asn Lys Ser Val Ser Pro Thr Val Asn Pro Met Ser Thr
        510                 515                 520

GCT ATG CAG AAT GAA CGC AAC CTG TCA CAT AAT AGG CGT GTG CCA AAA         1633
Ala Met Gln Asn Glu Arg Asn Leu Ser His Asn Arg Arg Val Pro Lys
    525                 530                 535

ATC GGG CCT TAC CCA GAT TAT TCC TCT TCC TCA TAT ATT GAA GAC TCT         1681
Ile Gly Pro Tyr Pro Asp Tyr Ser Ser Ser Ser Tyr Ile Glu Asp Ser
540                 545                 550                 555

ATC CAT CAT ACT GAC AGC ATT GTG AAG AAT ATT TCC TCT GAG CAT TCG         1729
Ile His His Thr Asp Ser Ile Val Lys Asn Ile Ser Ser Glu His Ser
                560                 565                 570

ATG TCC AGC ACA CCA TTG ACA ATA GGA GAA AAG AAT CGA AAT TCA ATT         1777
Met Ser Ser Thr Pro Leu Thr Ile Gly Glu Lys Asn Arg Asn Ser Ile
            575                 580                 585

AAT TAT GAA CGA CAG CAA GCA CAA GCT CGA ATC CCT AGC CCA GAA ACA         1825
Asn Tyr Glu Arg Gln Gln Ala Gln Ala Arg Ile Pro Ser Pro Glu Thr
        590                 595                 600

AGC GTC ACA AGC CTG TCC ACA AAC ACA ACC ACC ACA AAC ACC ACC GGC         1873
Ser Val Thr Ser Leu Ser Thr Asn Thr Thr Thr Thr Asn Thr Thr Gly
    605                 610                 615

CTC ACT CCA AGT ACT GGC ATG ACC ACT ATA TCT GAG ATG CCA TAC CCA         1921
Leu Thr Pro Ser Thr Gly Met Thr Thr Ile Ser Glu Met Pro Tyr Pro
620                 625                 630                 635

GAT GAG ACA CAT TTG CAC GCC ACA AAT GTT GCA CAG TCA ATC GGG CCA         1969
Asp Glu Thr His Leu His Ala Thr Asn Val Ala Gln Ser Ile Gly Pro
                640                 645                 650

ACC CCT GTC TGC TTA CAG CTG ACA GAA GAA GAC TTG GAG ACT AAT AAG         2017
Thr Pro Val Cys Leu Gln Leu Thr Glu Glu Asp Leu Glu Thr Asn Lys
            655                 660                 665

CTA GAT CCA AAA GAA GTT GAT AAG AAC CTC AAG GAA AGC TCT GAT GAG         2065
Leu Asp Pro Lys Glu Val Asp Lys Asn Leu Lys Glu Ser Ser Asp Glu
        670                 675                 680

AAT CTC ATG GAG CAT TCT CTG AAG CAG TTC AGT GGG CCA GAC CCA TTG         2113
Asn Leu Met Glu His Ser Leu Lys Gln Phe Ser Gly Pro Asp Pro Leu
    685                 690                 695

AGC AGT ACC AGT TCT AGC TTG CTT TAT CCA CTC ATA AAG CTC GCA GTG         2161
Ser Ser Thr Ser Ser Leu Leu Tyr Pro Leu Ile Lys Leu Ala Val
700                 705                 710                 715

GAA GTG ACT GGA CAA CAG GAC TTC ACA CAG GCT GCA AAT GGG CAA GCA         2209
Glu Val Thr Gly Gln Gln Asp Phe Thr Gln Ala Ala Asn Gly Gln Ala
                720                 725                 730

TGT TTA ATT CCT GAT GTT CCA CCT GCT CAG ATC TAT CCT CTC CCT AAG         2257
Cys Leu Ile Pro Asp Val Pro Pro Ala Gln Ile Tyr Pro Leu Pro Lys
            735                 740                 745

CAA CAG AAC CTT CCT AAG AGA CCT ACT AGT TTG CCT TTG AAC ACC AAA         2305
Gln Gln Asn Leu Pro Lys Arg Pro Thr Ser Leu Pro Leu Asn Thr Lys
```

```
                750                    755                     760
AAT TCA ACA AAA GAA CCC CGG CTA AAA TTT GGC AAC AAG CAC AAA TCA    2353
Asn Ser Thr Lys Glu Pro Arg Leu Lys Phe Gly Asn Lys His Lys Ser
    765                    770                     775

AAC TTG AAA CAA GTA GAA ACT GGA GTT GCC AAG ATG AAT ACA ATC AAT    2401
Asn Leu Lys Gln Val Glu Thr Gly Val Ala Lys Met Asn Thr Ile Asn
780                     785                     790                     795

GCA GCA GAG CCT CAT GTG GTG ACA GTA ACT ATG AAT GGT GTG GCA GGT    2449
Ala Ala Glu Pro His Val Val Thr Val Thr Met Asn Gly Val Ala Gly
                    800                     805                     810

AGA AGC CAC AAT GTT AAT TCT CAT GCT GCC ACA ACC CAG TAT GCC AAT    2497
Arg Ser His Asn Val Asn Ser His Ala Ala Thr Thr Gln Tyr Ala Asn
            815                     820                     825

GGC GCA GTG CCA GCT GGC CAG GCA GCC AAC ATA GTG GCA CAT AGG TCC    2545
Gly Ala Val Pro Ala Gly Gln Ala Ala Asn Ile Val Ala His Arg Ser
        830                     835                     840

CAA GAA ATG CTG CAG AAT CAA TTT ATT GGT GAG GAT ACC AGG CTG AAT    2593
Gln Glu Met Leu Gln Asn Gln Phe Ile Gly Glu Asp Thr Arg Leu Asn
    845                     850                     855

ATC AAT TCC AGT CCT GAT GAG CAT GAA CCT TTA CTG AGA CGA GAG CAA    2641
Ile Asn Ser Ser Pro Asp Glu His Glu Pro Leu Leu Arg Arg Glu Gln
860                     865                     870                     875

CAG GCT GGC CAT GAT GAA GGG GTT CTG GAT CGT TTG GTA GAT AGG AGG    2689
Gln Ala Gly His Asp Glu Gly Val Leu Asp Arg Leu Val Asp Arg Arg
                    880                     885                     890

GAA CGG CCA TTA GAA GGT GGC CGA ACA AAT TCC AAT AAC AAC AAC AGC    2737
Glu Arg Pro Leu Glu Gly Gly Arg Thr Asn Ser Asn Asn Asn Asn Ser
            895                     900                     905

AAT CCA TGT TCA GAA CAA GAT ATC CTT ACA CAA GGT GTT ACA AGC ACA    2785
Asn Pro Cys Ser Glu Gln Asp Ile Leu Thr Gln Gly Val Thr Ser Thr
        910                     915                     920

GCT GCA GAT CCT GGG CCA TCA AAG CCC AGA AGA GCA CAG AGG CCC AAT    2833
Ala Ala Asp Pro Gly Pro Ser Lys Pro Arg Arg Ala Gln Arg Pro Asn
    925                     930                     935

TCT CTG GAT CTT TCA GCC ACA AAT ATC CTG GAT GGC AGC AGT ATA CAG    2881
Ser Leu Asp Leu Ser Ala Thr Asn Ile Leu Asp Gly Ser Ser Ile Gln
940                     945                     950                     955

ATA GGT GAG TCA ACA CAA GAT GGC AAA TCA GGA TCA GGT GAA AAG ATC    2929
Ile Gly Glu Ser Thr Gln Asp Gly Lys Ser Gly Ser Gly Glu Lys Ile
                    960                     965                     970

AAG AGA CGT GTG AAA ACT CCA TAC TCT CTT AAG CGG TGG CGC CCG TCC    2977
Lys Arg Arg Val Lys Thr Pro Tyr Ser Leu Lys Arg Trp Arg Pro Ser
            975                     980                     985

ACC TGG GTC ATC TCC ACC GAG CCG CTG GAC TGT GAG GTC AAC AAC AAT    3025
Thr Trp Val Ile Ser Thr Glu Pro Leu Asp Cys Glu Val Asn Asn Asn
        990                     995                     1000

GGC AGT GAC AGG GCA GTC CAT TCT AAA TCT AGC ACT GCT GTG TAC CTT    3073
Gly Ser Asp Arg Ala Val His Ser Lys Ser Ser Thr Ala Val Tyr Leu
    1005                    1010                    1015

GCA GAG GGA GGC ACT GCC ACG ACC ACA GTG TCT AAA GAT ATA GGA ATG    3121
Ala Glu Gly Gly Thr Ala Thr Thr Thr Val Ser Lys Asp Ile Gly Met
1020                    1025                    1030                    1035

AAT TGT CTG TGAGATGTTT TCAAGCTTAT GGAGTGAAAT TATTTTTTG             3170
Asn Cys Leu

CATCATTTAA ACATGCAGAA GACATTTAAA AAAAAAACTG CTTTAACCTC CTGTCAGCAC    3230

CCCTTCCCAC CCCTGCAGCA AGGACTTGCT TTAAATAGAT TTCAGCTATG CAGAAAATTT    3290

TAGCTTATGC TTCCATAATT TTTAATTTTG TTTTTTAAGT TTTGCACTTT TGTTTAGTCT    3350
```

-continued

```
TGCTAAAGTT ATATTTGTCT GTTATGACCA CATTATATGT GTGCTTATCC AAAGTGGTCT      3410

CCAAATATTT TTTTAAGAAA AAAGCCCAAA CAATGGATTG CTGATAATCA GTTTGGACCA      3470

TTTTCTAAAG GTCATTAAAA CAGAAGCAAA TTCAGACC                              3508
```

(2) INFORMATION FOR SEQ ID NO:8:

(i) SEQUENCE CHARACTERISTICS:
        (A) LENGTH: 1038 amino acids
        (B) TYPE: amino acid
        (D) TOPOLOGY: linear (ii) MOLECULE TYPE: protein (xi) SEQUENCE DESCRIPTION: SEQ ID NO:8:

```
Met Thr Ser Ser Leu His Arg Pro Phe Arg Val Pro Trp Leu Leu Trp
 1               5                  10                  15

Ala Val Leu Leu Val Ser Thr Thr Ala Ala Ser Gln Asn Gln Glu Arg
             20                  25                  30

Leu Cys Ala Phe Lys Asp Pro Tyr Gln Gln Asp Leu Gly Ile Gly Glu
         35                  40                  45

Ser Arg Ile Ser His Glu Asn Gly Thr Ile Leu Cys Ser Lys Gly Ser
     50                  55                  60

Thr Cys Tyr Gly Leu Trp Glu Lys Ser Lys Gly Asp Ile Asn Leu Val
 65                  70                  75                  80

Lys Gln Gly Cys Trp Ser His Ile Gly Asp Pro Gln Glu Cys His Tyr
                 85                  90                  95

Glu Glu Cys Val Val Thr Thr Pro Pro Ser Ile Gln Asn Gly Thr
            100                 105                 110

Tyr Arg Phe Cys Cys Cys Ser Thr Asp Leu Cys Asn Val Asn Phe Thr
            115                 120                 125

Glu Asn Phe Pro Pro Pro Asp Thr Thr Pro Leu Ser Pro Pro His Ser
        130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ala Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Leu Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
```

-continued

```
                    325                 330                 335
        Arg Asn Val Leu Val Lys Asn Asp Gly Ala Cys Val Ile Ser Asp Phe
                        340                 345                 350
        Gly Leu Ser Met Arg Leu Thr Gly Asn Arg Leu Val Arg Pro Gly Glu
                        355                 360                 365
        Glu Asp Asn Ala Ala Ile Ser Glu Val Gly Thr Ile Arg Tyr Met Ala
                        370                 375                 380
        Pro Glu Val Leu Glu Gly Ala Val Asn Leu Arg Asp Cys Glu Ser Ala
        385                 390                 395                 400
        Leu Lys Gln Val Asp Met Tyr Ala Leu Gly Leu Ile Tyr Trp Glu Val
                        405                 410                 415
        Phe Met Arg Cys Thr Asp Leu Phe Pro Gly Glu Ser Val Pro Asp Tyr
                        420                 425                 430
        Gln Met Ala Phe Gln Thr Glu Val Gly Asn His Pro Thr Phe Glu Asp
                        435                 440                 445
        Met Gln Val Leu Val Ser Arg Glu Lys Gln Arg Pro Lys Phe Pro Glu
                        450                 455                 460
        Ala Trp Lys Glu Asn Ser Leu Ala Val Arg Ser Leu Lys Glu Thr Ile
        465                 470                 475                 480
        Glu Asp Cys Trp Asp Gln Asp Ala Glu Ala Arg Leu Thr Ala Gln Cys
                        485                 490                 495
        Ala Glu Glu Arg Met Ala Glu Leu Met Met Ile Trp Glu Arg Asn Lys
                        500                 505                 510
        Ser Val Ser Pro Thr Val Asn Pro Met Ser Thr Ala Met Gln Asn Glu
                        515                 520                 525
        Arg Asn Leu Ser His Asn Arg Arg Val Pro Lys Ile Gly Pro Tyr Pro
                        530                 535                 540
        Asp Tyr Ser Ser Ser Tyr Ile Glu Asp Ser Ile His His Thr Asp
        545                 550                 555                 560
        Ser Ile Val Lys Asn Ile Ser Ser Glu His Ser Met Ser Ser Thr Pro
                        565                 570                 575
        Leu Thr Ile Gly Glu Lys Asn Arg Asn Ser Ile Asn Tyr Glu Arg Gln
                        580                 585                 590
        Gln Ala Gln Ala Arg Ile Pro Ser Pro Glu Thr Ser Val Thr Ser Leu
                        595                 600                 605
        Ser Thr Asn Thr Thr Thr Thr Asn Thr Thr Gly Leu Thr Pro Ser Thr
                        610                 615                 620
        Gly Met Thr Thr Ile Ser Glu Met Pro Tyr Pro Asp Glu Thr His Leu
        625                 630                 635                 640
        His Ala Thr Asn Val Ala Gln Ser Ile Gly Pro Thr Pro Val Cys Leu
                        645                 650                 655
        Gln Leu Thr Glu Glu Asp Leu Glu Thr Asn Lys Leu Asp Pro Lys Glu
                        660                 665                 670
        Val Asp Lys Asn Leu Lys Glu Ser Asp Glu Asn Leu Met Glu His
                        675                 680                 685
        Ser Leu Lys Gln Phe Ser Gly Pro Asp Pro Leu Ser Ser Thr Ser Ser
                        690                 695                 700
        Ser Leu Leu Tyr Pro Leu Ile Lys Leu Ala Val Glu Val Thr Gly Gln
        705                 710                 715                 720
        Gln Asp Phe Thr Gln Ala Ala Asn Gly Gln Ala Cys Leu Ile Pro Asp
                        725                 730                 735
        Val Pro Pro Ala Gln Ile Tyr Pro Leu Pro Lys Gln Gln Asn Leu Pro
                        740                 745                 750
```

-continued

```
Lys Arg Pro Thr Ser Leu Pro Leu Asn Thr Lys Asn Ser Thr Lys Glu
        755                 760                 765
Pro Arg Leu Lys Phe Gly Asn Lys His Lys Ser Asn Leu Lys Gln Val
        770                 775                 780
Glu Thr Gly Val Ala Lys Met Asn Thr Ile Asn Ala Ala Glu Pro His
785                 790                 795                 800
Val Val Thr Val Thr Met Asn Gly Val Ala Gly Arg Ser His Asn Val
                805                 810                 815
Asn Ser His Ala Ala Thr Thr Gln Tyr Ala Asn Gly Ala Val Pro Ala
        820                 825                 830
Gly Gln Ala Ala Asn Ile Val Ala His Arg Ser Gln Glu Met Leu Gln
        835                 840                 845
Asn Gln Phe Ile Gly Glu Asp Thr Arg Leu Asn Ile Asn Ser Ser Pro
850                 855                 860
Asp Glu His Glu Pro Leu Leu Arg Arg Glu Gln Gln Ala Gly His Asp
865                 870                 875                 880
Glu Gly Val Leu Asp Arg Leu Val Asp Arg Arg Glu Arg Pro Leu Glu
                885                 890                 895
Gly Gly Arg Thr Asn Ser Asn Asn Asn Ser Asn Pro Cys Ser Glu
        900                 905                 910
Gln Asp Ile Leu Thr Gln Gly Val Thr Ser Thr Ala Ala Asp Pro Gly
        915                 920                 925
Pro Ser Lys Pro Arg Arg Ala Gln Arg Pro Asn Ser Leu Asp Leu Ser
        930                 935                 940
Ala Thr Asn Ile Leu Asp Gly Ser Ser Ile Gln Ile Gly Glu Ser Thr
945                 950                 955                 960
Gln Asp Gly Lys Ser Gly Ser Gly Glu Lys Ile Lys Arg Arg Val Lys
                965                 970                 975
Thr Pro Tyr Ser Leu Lys Arg Trp Arg Pro Ser Thr Trp Val Ile Ser
                980                 985                 990
Thr Glu Pro Leu Asp Cys Glu Val Asn Asn Asn Gly Ser Asp Arg Ala
        995                 1000                1005
Val His Ser Lys Ser Ser Thr Ala Val Tyr Leu Ala Glu Gly Gly Thr
        1010                1015                1020
Ala Thr Thr Thr Val Ser Lys Asp Ile Gly Met Asn Cys Leu
1025                1030                1035

(2) INFORMATION FOR SEQ ID NO:9:

(i) SEQUENCE CHARACTERISTICS:
        (A) LENGTH: 469 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: join(17..466)

(xi) SEQUENCE DESCRIPTION: SEQ ID NO:9:

CTTTGCTGGC CCAGGG ATG ACT TCC TCG CTG CAT CGG CCC TTT CGG GTG          49
               Met Thr Ser Ser Leu His Arg Pro Phe Arg Val
                 1               5                  10

CCC TGG CTG CTA TGG GCC GTC CTG CTG GTC AGC ACT ACG GCT GCT TCT        97
Pro Trp Leu Leu Trp Ala Val Leu Leu Val Ser Thr Thr Ala Ala Ser
            15                  20                  25
```

```
CAG AAT CAA GAA CGG CTG TGT GCA TTT AAA GAT CCA TAT CAA CAA GAT    145
Gln Asn Gln Glu Arg Leu Cys Ala Phe Lys Asp Pro Tyr Gln Gln Asp
         30                  35                  40

CTT GGG ATA GGT GAG AGT CGA ATC TCT CAT GAA AAT GGG ACA ATA TTA    193
Leu Gly Ile Gly Glu Ser Arg Ile Ser His Glu Asn Gly Thr Ile Leu
             45                  50                  55

TGT TCC AAA GGG AGC ACG TGT TAT GGT CTG TGG GAG AAA TCA AAA GGG    241
Cys Ser Lys Gly Ser Thr Cys Tyr Gly Leu Trp Glu Lys Ser Lys Gly
 60                  65                  70                  75

GAC ATC AAT CTT GTG AAA CAA GGA TGT TGG TCT CAC ATC GGT GAT CCC    289
Asp Ile Asn Leu Val Lys Gln Gly Cys Trp Ser His Ile Gly Asp Pro
                 80                  85                  90

CAA GAG TGC CAC TAT GAA GAG TGT GTA GTA ACT ACC ACC CCA CCC TCA    337
Gln Glu Cys His Tyr Glu Glu Cys Val Val Thr Thr Thr Pro Pro Ser
                     95                 100                 105

ATT CAG AAT GGA ACG TAC CGC TTT TGC TGC TGT AGT ACA GAT TTA TGT    385
Ile Gln Asn Gly Thr Tyr Arg Phe Cys Cys Cys Ser Thr Asp Leu Cys
                         110                 115                 120

AAT GTC AAC TTT ACT GAG AAC TTT CCA CCC CCT GAC ACA ACA CCA CTC    433
Asn Val Asn Phe Thr Glu Asn Phe Pro Pro Pro Asp Thr Thr Pro Leu
                             125                 130                 135

AGT CCA CCT CAT TCA TTT AAT CGA GAT GAA ACG TGA                   469
Ser Pro Pro His Ser Phe Asn Arg Asp Glu Thr
140                 145                 150

(2) INFORMATION FOR SEQ ID NO:10:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:10:

Met Thr Ser Ser Leu His Arg Pro Phe Arg Val Pro Trp Leu Leu Trp
 1               5                  10                  15

Ala Val Leu Leu Val Ser Thr Thr Ala Ala Ser Gln Asn Gln Glu Arg
             20                  25                  30

Leu Cys Ala Phe Lys Asp Pro Tyr Gln Gln Asp Leu Gly Ile Gly Glu
         35                  40                  45

Ser Arg Ile Ser His Glu Asn Gly Thr Ile Leu Cys Ser Lys Gly Ser
     50                  55                  60

Thr Cys Tyr Gly Leu Trp Glu Lys Ser Lys Gly Asp Ile Asn Leu Val
 65                  70                  75                  80

Lys Gln Gly Cys Trp Ser His Ile Gly Asp Pro Gln Glu Cys His Tyr
             85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
            115                 120                 125

Glu Asn Phe Pro Pro Pro Asp Thr Thr Pro Leu Ser Pro Pro His Ser
        130                 135                 140

Phe Asn Arg Asp Glu Thr
145                 150

(2) INFORMATION FOR SEQ ID NO:11:

(i) SEQUENCE CHARACTERISTICS:
```

-continued

```
        (A) LENGTH: 2402 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: join(11..1606)

(xi) SEQUENCE DESCRIPTION: SEQ ID NO:11:

GAATCAGACA ATG ACT CAG CTA TAC ACT TAC ATC AGA TTA CTG GGA GCC         49
           Met Thr Gln Leu Tyr Thr Tyr Ile Arg Leu Leu Gly Ala
             1               5                  10

TGT CTG TTC ATC ATT TCT CAT GTT CAA GGG CAG AAT CTA GAT AGT ATG         97
Cys Leu Phe Ile Ile Ser His Val Gln Gly Gln Asn Leu Asp Ser Met
 15              20                  25

CTC CAT GGC ACT GGT ATG AAA TCA GAC TTG GAC CAG AAG AAG CCA GAA        145
Leu His Gly Thr Gly Met Lys Ser Asp Leu Asp Gln Lys Lys Pro Glu
 30              35                  40                  45

AAT GGA GTG ACT TTA GCA CCA GAG GAT ACC TTG CCT TTC TTA AAG TGC        193
Asn Gly Val Thr Leu Ala Pro Glu Asp Thr Leu Pro Phe Leu Lys Cys
                 50                  55                  60

TAT TGC TCA GGA CAC TGC CCA GAT GAT GCT ATT AAT AAC ACA TGC ATA        241
Tyr Cys Ser Gly His Cys Pro Asp Asp Ala Ile Asn Asn Thr Cys Ile
             65                  70                  75

ACT AAT GGC CAT TGC TTT GCC ATT ATA GAA GAA GAT GAT CAG GGA GAA        289
Thr Asn Gly His Cys Phe Ala Ile Ile Glu Glu Asp Asp Gln Gly Glu
         80                  85                  90

ACC ACA TTA ACT TCT GGG TGT ATG AAG TAT GAA GGC TCT GAT TTT CAA        337
Thr Thr Leu Thr Ser Gly Cys Met Lys Tyr Glu Gly Ser Asp Phe Gln
     95                 100                 105

TGC AAG GAT TCA CCG AAA GCC CAG CTA CGC AGG ACA ATA GAA TGT TGT        385
Cys Lys Asp Ser Pro Lys Ala Gln Leu Arg Arg Thr Ile Glu Cys Cys
110             115                 120                 125

CGG ACC AAT TTG TGC AAC CAG TAT TTG CAG CCT ACA CTG CCC CCT GTT        433
Arg Thr Asn Leu Cys Asn Gln Tyr Leu Gln Pro Thr Leu Pro Pro Val
                130                 135                 140

GTT ATA GGT CCG TTC TTT GAT GGC AGC ATC CGA TGG CTG GTT GTG CTC        481
Val Ile Gly Pro Phe Phe Asp Gly Ser Ile Arg Trp Leu Val Val Leu
            145                 150                 155

ATT TCC ATG GCT GTC TGT ATA GTT GCT ATG ATC ATC TTC TCC AGC TGC        529
Ile Ser Met Ala Val Cys Ile Val Ala Met Ile Ile Phe Ser Ser Cys
        160                 165                 170

TTT TGC TAT AAG CAT TAT TGT AAG AGT ATC TCA AGC AGG GGT CGT TAC        577
Phe Cys Tyr Lys His Tyr Cys Lys Ser Ile Ser Ser Arg Gly Arg Tyr
    175                 180                 185

AAC CGT GAT TTG GAA CAG GAT GAA GCA TTT ATT CCA GTA GGA GAA TCA        625
Asn Arg Asp Leu Glu Gln Asp Glu Ala Phe Ile Pro Val Gly Glu Ser
190                 195                 200                 205

TTG AAA GAC CTG ATT GAC CAG TCC CAA AGC TCT GGG AGT GGA TCT GGA        673
Leu Lys Asp Leu Ile Asp Gln Ser Gln Ser Ser Gly Ser Gly Ser Gly
                210                 215                 220

TTG CCT TTA TTG GTT CAG CGA ACT ATT GCC AAA CAG ATT CAG ATG GTT        721
Leu Pro Leu Leu Val Gln Arg Thr Ile Ala Lys Gln Ile Gln Met Val
            225                 230                 235

CGG CAG GTT GGT AAA GGC CGC TAT GGA GAA GTA TGG ATG GGT AAA TGG        769
Arg Gln Val Gly Lys Gly Arg Tyr Gly Glu Val Trp Met Gly Lys Trp
        240                 245                 250

CGT GGT GAA AAA GTG GCT GTC AAA GTG TTT TTT ACC ACT GAA GAA GCT        817
Arg Gly Glu Lys Val Ala Val Lys Val Phe Phe Thr Thr Glu Glu Ala
```

```
                255                    260                     265
AGC TGG TTT AGA GAA ACA GAA ATC TAC CAG ACG GTG TTA ATG CGT CAT        865
Ser Trp Phe Arg Glu Thr Glu Ile Tyr Gln Thr Val Leu Met Arg His
270             275                 280                 285

GAA AAT ATA CTT GGT TTT ATA GCT GCA GAC ATT AAA GGC ACT GGT TCC        913
Glu Asn Ile Leu Gly Phe Ile Ala Ala Asp Ile Lys Gly Thr Gly Ser
                    290                 295                 300

TGG ACT CAG CTG TAT TTG ATT ACT GAT TAC CAT GAA AAT GGA TCT CTC        961
Trp Thr Gln Leu Tyr Leu Ile Thr Asp Tyr His Glu Asn Gly Ser Leu
                305                 310                 315

TAT GAC TTC CTG AAA TGT GCC ACA CTA GAC ACC AGA GCC CTA CTC AAG       1009
Tyr Asp Phe Leu Lys Cys Ala Thr Leu Asp Thr Arg Ala Leu Leu Lys
            320                 325                 330

TTA GCT TAT TCT GCT GCT TGT GGT CTG TGC CAC CTC CAC ACA GAA ATT       1057
Leu Ala Tyr Ser Ala Ala Cys Gly Leu Cys His Leu His Thr Glu Ile
335             340                 345

TAT GGT ACC CAA GGG AAG CCT GCA ATT GCT CAT CGA GAC CTG AAG AGC       1105
Tyr Gly Thr Gln Gly Lys Pro Ala Ile Ala His Arg Asp Leu Lys Ser
350             355                 360                 365

AAA AAC ATC CTT ATT AAG AAA AAT GGA AGT TGC TGT ATT GCT GAC CTG       1153
Lys Asn Ile Leu Ile Lys Lys Asn Gly Ser Cys Cys Ile Ala Asp Leu
                370                 375                 380

GGC CTA GCT GTT AAA TTC AAC AGT GAT ACA AAT GAA GTT GAC ATA CCC       1201
Gly Leu Ala Val Lys Phe Asn Ser Asp Thr Asn Glu Val Asp Ile Pro
            385                 390                 395

TTG AAT ACC AGG GTG GGC ACC AAG CGG TAC ATG GCT CCA GAA GTG CTG       1249
Leu Asn Thr Arg Val Gly Thr Lys Arg Tyr Met Ala Pro Glu Val Leu
        400                 405                 410

GAT GAA AGC CTG AAT AAA AAC CAT TTC CAG CCC TAC ATC ATG GCT GAC       1297
Asp Glu Ser Leu Asn Lys Asn His Phe Gln Pro Tyr Ile Met Ala Asp
415                 420                 425

ATC TAT AGC TTT GGT TTG ATC ATT TGG GAA ATG GCT CGT CGT TGT ATT       1345
Ile Tyr Ser Phe Gly Leu Ile Ile Trp Glu Met Ala Arg Arg Cys Ile
430             435                 440                 445

ACA GGA GGA ATC GTG GAG GAA TAT CAA TTA CCA TAT TAC AAC ATG GTG       1393
Thr Gly Gly Ile Val Glu Glu Tyr Gln Leu Pro Tyr Tyr Asn Met Val
                450                 455                 460

CCC AGT GAC CCA TCC TAT GAG GAC ATG CGT GAG GTT GTG TGT GTG AAA       1441
Pro Ser Asp Pro Ser Tyr Glu Asp Met Arg Glu Val Val Cys Val Lys
            465                 470                 475

CGC TTG CGG CCA ATC GTG TCT AAC CGC TGG AAC AGC GAT GAA TGT CTT       1489
Arg Leu Arg Pro Ile Val Ser Asn Arg Trp Asn Ser Asp Glu Cys Leu
        480                 485                 490

CGA GCA GTT TTG AAG CTA ATG TCA GAA TGT TGG GCC CAT AAT CCA GCC       1537
Arg Ala Val Leu Lys Leu Met Ser Glu Cys Trp Ala His Asn Pro Ala
495                 500                 505

TCC AGA CTC ACA GCT TTG AGA ATC AAG AAG ACA CTT GCA AAA ATG GTT       1585
Ser Arg Leu Thr Ala Leu Arg Ile Lys Lys Thr Leu Ala Lys Met Val
510             515                 520                 525

GAA TCC CAG GAT GTA AAG ATT TGACAATTAA ACAATTTTGA GGGAGAATTT          1636
Glu Ser Gln Asp Val Lys Ile
                530

AGACTGCAAG AACTTCTTCA CCCAAGGAAT GGGTGGGATT AGCATGGAAT AGGATGTTGA     1696

CTTGGTTTCC AGACTCCTTC CTCTACATCT TCACAGGCTG CTAACAGTAA ACCTTACCGC     1756

ACTCTACAGA ATACAAGATT GGAACTTGGA ACTTGGAACT TCAAACATGT CATTCTTTAT     1816

ATATGGACAG CTGTGTTTTA AATGTGGGGT TTTTGTGTTT TGCTTTCTTT GTTTTGTTTT     1876

GGTTTTGATG CTTTTTTGGT TTTTATGAAC TGCATCAAGA CTCCAATCCT GATAAGAAGT     1936
```

```
CTCTGGTCAA CCTCTGGGTA CTCACTATCC TGTCCATAAA GTGGTGCTTT CTGTGAAAGC      1996

CTTAAGAAAA TTAATGAGCT CAGCAGAGAT GGAAAAAGGC ATATTTGGCT TCTACCAGAG      2056

AAAACATCTG TCTGTGTTCT GTCTTTGTAA ACAGCCTATA GATTATGATC TCTTTGGGAT      2116

ACTGCCTGGC TTATGATGGT GCACCATACC TTTGATATAC ATACCAGAAT TCTCTCCTGC      2176

CCTAGGGCTA AGAAGACAAG AATGTAGAGG TTGCACAGGA GGTATTTTGT GACCAGTGGT      2236

TTAAATTGCA ATATCTAGTT GGCAATCGCC AATTTCATAA AAGCCATCCA CCTTGTAGCT      2296

GTAGTAACTT CTCCACTGAC TTTATTTTTA GCATAATAGT TGTGAAGGCC AAACTCCATG      2356

TAAAGTGTCC ATAGACTTGG ACTGTTTTCC CCCAGCTCTG ATTACC                     2402
```

(2) INFORMATION FOR SEQ ID NO:12:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO:12:

```
Met Thr Gln Leu Tyr Thr Tyr Ile Arg Leu Leu Gly Ala Cys Leu Phe
 1               5                  10                  15

Ile Ile Ser His Val Gln Gly Gln Asn Leu Asp Ser Met Leu His Gly
                20                  25                  30

Thr Gly Met Lys Ser Asp Leu Asp Gln Lys Lys Pro Glu Asn Gly Val
            35                  40                  45

Thr Leu Ala Pro Glu Asp Thr Leu Pro Phe Leu Lys Cys Tyr Cys Ser
        50                  55                  60

Gly His Cys Pro Asp Asp Ala Ile Asn Asn Thr Cys Ile Thr Asn Gly
 65                  70                  75                  80

His Cys Phe Ala Ile Ile Glu Glu Asp Asp Gln Gly Glu Thr Thr Leu
                85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Ile Arg Trp Leu Val Val Leu Ile Ser Met
145                 150                 155                 160

Ala Val Cys Ile Val Ala Met Ile Ile Phe Ser Ser Cys Phe Cys Tyr
                165                 170                 175

Lys His Tyr Cys Lys Ser Ile Ser Ser Arg Gly Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270
```

```
Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
        290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
                340                 345                 350

Gln Gly Lys Pro Ala Ile Ala His Arg Asp Leu Lys Ser Lys Asn Ile
        355                 360                 365

Leu Ile Lys Lys Asn Gly Ser Cys Cys Ile Ala Asp Leu Gly Leu Ala
        370                 375                 380

Val Lys Phe Asn Ser Asp Thr Asn Glu Val Asp Ile Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
                420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
        450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
        500                 505                 510

Thr Ala Leu Arg Ile Lys Lys Thr Leu Ala Lys Met Val Glu Ser Gln
        515                 520                 525

Asp Val Lys Ile
    530

(2) INFORMATION FOR SEQ ID NO:13:

(i) SEQUENCE CHARACTERISTICS:
        (A) LENGTH: 2252 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat_peptide
        (B) LOCATION: join(355..1860)

(ix) FEATURE:
        (A) NAME/KEY: CDS
        (B) LOCATION: join(355..1860)

(xi) SEQUENCE DESCRIPTION: SEQ ID NO:13:

GTTTTCCAGC AGACTGATGC TATAAATGCT CCACAACATG GAGAATGGTT TGGGTTGGAA      60

GTAGACTTAA AGACCATCTA TGTGTGGGGA TACCTCCCAC TAGATCAGGC TGCTCAGGGC     120

CCCATTCACC ACCTCCAGGG ACGGGGTAGC CACTGCTTCT CTGAGCAACC TGAGCAACTT     180
```

```
CCTCACAGTG AAGAGTTCCT CCTGTATCCG AGGGTGGAGT TCATTTCTTT TGTCCTTGGA        240

AGTTGAATAG CAGAAAGGGA CATTTCAGCT TTTCTTGATA AAGGTTACAT CCATTTTACT        300

TAGACTACAA GACGAAGATT TCTGAAAATT GAGATCTTTA GTTTTCTGGA CAAG ATG          357
                                                              Met
                                                               1

CCC TTG CTT AGC TCC AGC AAG TTG AGC ATG GAG AGC AGA AAA GAA GAT          405
Pro Leu Leu Ser Ser Ser Lys Leu Ser Met Glu Ser Arg Lys Glu Asp
            5                  10                  15

AGT GAG GGC ACA GCA CCT GCC CCT CCA CAG AAG AAG CTG TCA TGT CAG          453
Ser Glu Gly Thr Ala Pro Ala Pro Pro Gln Lys Lys Leu Ser Cys Gln
            20                  25                  30

TGC CAC CAC CAT TGT CCT GAG GAC TCA GTC AAC AGC ACC TGC AGC ACT          501
Cys His His His Cys Pro Glu Asp Ser Val Asn Ser Thr Cys Ser Thr
        35                  40                  45

GAT GGC TAC TGC TTC ACC ATA ATA GAA GAA GAT GAT TCT GGT GGA CAT          549
Asp Gly Tyr Cys Phe Thr Ile Ile Glu Glu Asp Asp Ser Gly Gly His
50                  55                  60                  65

TTG GTC ACC AAA GGA TGT CTA GGA TTA GAG GGC TCG GAC TTC CAG TGT          597
Leu Val Thr Lys Gly Cys Leu Gly Leu Glu Gly Ser Asp Phe Gln Cys
                70                  75                  80

CGG GAC ACT CCT ATT CCA CAC CAA AGA AGA TCT ATT GAA TGC TGC ACA          645
Arg Asp Thr Pro Ile Pro His Gln Arg Arg Ser Ile Glu Cys Cys Thr
                85                  90                  95

GGC CAA GAT TAC TGT AAC AAA CAT CTT CAC CCA ACG CTG CCA CCA CTG          693
Gly Gln Asp Tyr Cys Asn Lys His Leu His Pro Thr Leu Pro Pro Leu
            100                 105                 110

AAA AAT CGA GAC TTT GCT GAA GGA AAC ATT CAC CAT AAG GCC CTG CTG          741
Lys Asn Arg Asp Phe Ala Glu Gly Asn Ile His His Lys Ala Leu Leu
        115                 120                 125

ATC TCG GTG ACT GTC TGT AGT ATA CTA CTG GTG CTT ATC ATC ATA TTC          789
Ile Ser Val Thr Val Cys Ser Ile Leu Leu Val Leu Ile Ile Ile Phe
130                 135                 140                 145

TGC TAC TTC AGG TAC AAG CGG CAA GAA GCC AGG CCC CGC TAC AGC ATC          837
Cys Tyr Phe Arg Tyr Lys Arg Gln Glu Ala Arg Pro Arg Tyr Ser Ile
                150                 155                 160

GGG CTG GAG CAG GAC GAG ACC TAC ATT CCC CCT GGA GAA TCC CTG AAG          885
Gly Leu Glu Gln Asp Glu Thr Tyr Ile Pro Pro Gly Glu Ser Leu Lys
            165                 170                 175

GAT CTG ATC GAG CAG TCC CAG AGC TCA GGC AGC GGC TCC GGG CTC CCT          933
Asp Leu Ile Glu Gln Ser Gln Ser Ser Gly Ser Gly Ser Gly Leu Pro
        180                 185                 190

CTC CTG GTT CAA AGG ACC ATA GCA AAA CAG ATT CAG ATG GTA AAA CAG          981
Leu Leu Val Gln Arg Thr Ile Ala Lys Gln Ile Gln Met Val Lys Gln
        195                 200                 205

ATT GGA AAA GGT CGC TAT GGG GAA GTC TGG ATG GGA AAG TGG CGT GGC         1029
Ile Gly Lys Gly Arg Tyr Gly Glu Val Trp Met Gly Lys Trp Arg Gly
210                 215                 220                 225

GAA AAG GTA GCT GTC AAA GTG TTT TTT ACC ACG GAG GAG GCC AGC TGG         1077
Glu Lys Val Ala Val Lys Val Phe Phe Thr Thr Glu Glu Ala Ser Trp
                230                 235                 240

TTC AGA GAA ACA GAA ATC TAC CAA ACT GTC CTG ATG AGG CAT GAA AAT         1125
Phe Arg Glu Thr Glu Ile Tyr Gln Thr Val Leu Met Arg His Glu Asn
            245                 250                 255

ATT CTC GGA TTC ATT GCG GCA GAC ATT AAA GGC ACA GGC TCT TGG ACC         1173
Ile Leu Gly Phe Ile Ala Ala Asp Ile Lys Gly Thr Gly Ser Trp Thr
        260                 265                 270

CAA CTG TAT CTC ATC ACT GAC TAT CAT GAG AAT GGC TCC CTT TAC GAT         1221
Gln Leu Tyr Leu Ile Thr Asp Tyr His Glu Asn Gly Ser Leu Tyr Asp
    275                 280                 285
```

```
TAC CTA AAA TCC ACC ACC CTG GAC ACA AAA GGC ATG CTA AAA TTG GCT    1269
Tyr Leu Lys Ser Thr Thr Leu Asp Thr Lys Gly Met Leu Lys Leu Ala
290             295                 300                 305

TAC TCC TCT GTT AGT GGC TTG TGC CAC CTA CAT ACA GGG ATC TTC AGT    1317
Tyr Ser Ser Val Ser Gly Leu Cys His Leu His Thr Gly Ile Phe Ser
                310                 315                 320

ACC CAA GGC AAA CCG GCT ATT GCC CAC CGT GAT CTA AAA AGT AAG AAC    1365
Thr Gln Gly Lys Pro Ala Ile Ala His Arg Asp Leu Lys Ser Lys Asn
            325                 330                 335

ATC CTG GTG AAA AAG AAC GGA ACC TGC TGT ATA GCA GAT TTG GGC TTG    1413
Ile Leu Val Lys Lys Asn Gly Thr Cys Cys Ile Ala Asp Leu Gly Leu
        340                 345                 350

GCT GTT AAA TTT ATT AGT GAT ACA AAT GAG GTA GAC ATC CCT CCA AAC    1461
Ala Val Lys Phe Ile Ser Asp Thr Asn Glu Val Asp Ile Pro Pro Asn
    355                 360                 365

ACC CGC GTA GGA ACA AAA CGC TAT ATG CCT CCT GAG GTG CTG GAT GAA    1509
Thr Arg Val Gly Thr Lys Arg Tyr Met Pro Pro Glu Val Leu Asp Glu
370                 375                 380                 385

AGC TTG AAC AGA AAT CAC TTT CAG TCG TAC ATC ATG GCT GAT ATG TAC    1557
Ser Leu Asn Arg Asn His Phe Gln Ser Tyr Ile Met Ala Asp Met Tyr
                390                 395                 400

AGC TTT GGA CTC ATC CTT TGG GAG ATA GCC AGG AGA TGT GTG TCA GGA    1605
Ser Phe Gly Leu Ile Leu Trp Glu Ile Ala Arg Arg Cys Val Ser Gly
            405                 410                 415

GGA ATA GTG GAA GAA TAC CAG CTC CCA TAT CAC GAC CTT GTC CCC AGT    1653
Gly Ile Val Glu Glu Tyr Gln Leu Pro Tyr His Asp Leu Val Pro Ser
        420                 425                 430

GAC CCC TCC TAC GAG GAC ATG AGG GAG ATT GTG TGC ATC AAA AGG CTA    1701
Asp Pro Ser Tyr Glu Asp Met Arg Glu Ile Val Cys Ile Lys Arg Leu
    435                 440                 445

CGT CCT TCA TTC CCC AAC AGA TGG AGC AGC GAT GAG TGC CTG CGG CAG    1749
Arg Pro Ser Phe Pro Asn Arg Trp Ser Ser Asp Glu Cys Leu Arg Gln
450                 455                 460                 465

ATG GGG AAG CTC ATG ATG GAG TGC TGG GCC CAT AAC CCT GCA TCC CGG    1797
Met Gly Lys Leu Met Met Glu Cys Trp Ala His Asn Pro Ala Ser Arg
                470                 475                 480

CTC ACA GCC CTA CGA GTC AAA AAA ACA CTT GCC AAA ATG TCA GAG TCG    1845
Leu Thr Ala Leu Arg Val Lys Lys Thr Leu Ala Lys Met Ser Glu Ser
            485                 490                 495

CAG GAC ATT AAG CTC TGATGGAGCA AAAACAGCTC CTTCTCGTGA AGACCCATGG   1900
Gln Asp Ile Lys Leu
            500

AAACAGACTT TCTCTTGCAG GCAGAAGTCA TGGAGAGGTG CTGATAAGTA CCCTGAGTGC    1960

AGTCATATTT AAGAGCAACT GTTTGTTTGA CAGCTTTGAG GAGACTGTTC TTGGCAAAAT    2020

CAGCTGAATT TTGGCATGCA AGGTTGGGAG AGGCTTATCT GCCCTTGTTT ACACAGGGAT    2080

ATACAGTTTT AGTAACTGGT TTAAGGTTAT GCATGTTGCT TTCCGTGAAA GCCACTTATT    2140

ATTTTATTAT TATTGTTATT ATTATTATTT TGATTGTTTT AAAAGATACT GCTTTAAATT    2200

TTATGAAAAT AAAACCCTTT GGTTAGAAGA AAAAAAGATG TATATTGTTA CA           2252
```

(2) INFORMATION FOR SEQ ID NO:14:

(i) SEQUENCE CHARACTERISTICS:
        (A) LENGTH: 502 amino acids
        (B) TYPE: amino acid
        (D) TOPOLOGY: linear (ii) MOLECULE TYPE: protein -continued (xi) SEQUENCE DESCRIPTION: SEQ ID NO:14:

```
Met Pro Leu Leu Ser Ser Lys Leu Ser Met Glu Ser Arg Lys Glu
  1               5                  10                  15

Asp Ser Glu Gly Thr Ala Pro Ala Pro Gln Lys Lys Leu Ser Cys
              20                  25                  30

Gln Cys His His His Cys Pro Glu Asp Ser Val Asn Ser Thr Cys Ser
              35                  40                  45

Thr Asp Gly Tyr Cys Phe Thr Ile Ile Glu Glu Asp Ser Gly Gly
         50              55                  60

His Leu Val Thr Lys Gly Cys Leu Gly Leu Glu Gly Ser Asp Phe Gln
 65              70                  75                  80

Cys Arg Asp Thr Pro Ile Pro His Gln Arg Arg Ser Ile Glu Cys Cys
                  85                  90                  95

Thr Gly Gln Asp Tyr Cys Asn Lys His Leu His Pro Thr Leu Pro Pro
             100                 105                 110

Leu Lys Asn Arg Asp Phe Ala Glu Gly Asn Ile His His Lys Ala Leu
             115                 120                 125

Leu Ile Ser Val Thr Val Cys Ser Ile Leu Leu Val Leu Ile Ile Ile
     130                 135                 140

Phe Cys Tyr Phe Arg Tyr Lys Arg Gln Glu Ala Arg Pro Arg Tyr Ser
145                 150                 155                 160

Ile Gly Leu Glu Gln Asp Glu Thr Tyr Ile Pro Pro Gly Glu Ser Leu
                 165                 170                 175

Lys Asp Leu Ile Glu Gln Ser Gln Ser Ser Gly Ser Gly Ser Gly Leu
                 180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                 245                 250                 255

Asn Ile Leu Gly Phe Ile Ala Ala Asp Ile Lys Gly Thr Gly Ser Trp
                 260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Thr Lys Gly Met Leu Lys Leu
290                 295                 300

Ala Tyr Ser Ser Val Ser Gly Leu Cys His Leu His Thr Gly Ile Phe
305                 310                 315                 320

Ser Thr Gln Gly Lys Pro Ala Ile Ala His Arg Asp Leu Lys Ser Lys
                 325                 330                 335

Asn Ile Leu Val Lys Lys Asn Gly Thr Cys Cys Ile Ala Asp Leu Gly
                 340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
    370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Ile Ala Arg Arg Cys Val Ser
                 405                 410                 415
```

-continued

```
Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Ile Lys Arg
        435                 440                 445

Leu Arg Pro Ser Phe Pro Asn Arg Trp Ser Ser Asp Glu Cys Leu Arg
    450                 455                 460

Gln Met Gly Lys Leu Met Met Glu Cys Trp Ala His Asn Pro Ala Ser
465                 470                 475                 480

Arg Leu Thr Ala Leu Arg Val Lys Lys Thr Leu Ala Lys Met Ser Glu
            485                 490                 495

Ser Gln Asp Ile Lys Leu
            500
```